United States Patent
Tipler et al.

(10) Patent No.: US 10,024,829 B2
(45) Date of Patent: Jul. 17, 2018

(54) MANIFOLDS AND METHODS OF USING THEM TO CONTROL FLUID FLOWS

(71) Applicant: PERKINELMER HEALTH SCIENCES, INC., Waltham, MA (US)

(72) Inventors: Andrew Tipler, Trumbull, CT (US); John Irion, Seymour, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 339 days.

(21) Appl. No.: 14/499,383

(22) Filed: Sep. 29, 2014

(65) Prior Publication Data
US 2015/0089998 A1    Apr. 2, 2015

Related U.S. Application Data

(60) Provisional application No. 61/883,534, filed on Sep. 27, 2013.

(51) Int. Cl.
*G01N 33/66* (2006.01)
*G01N 30/66* (2006.01)
(Continued)

(52) U.S. Cl.
CPC ............ *G01N 30/66* (2013.01); *B01D 15/08* (2013.01); *B01D 15/1842* (2013.01); *B01D 15/265* (2013.01); *B01D 35/00* (2013.01); *B01D 53/0407* (2013.01); *B01D 63/00* (2013.01); *B01D 2259/40* (2013.01); *B01L 3/50273* (2013.01); *B01L 3/502715* (2013.01); *B01L 2300/0861* (2013.01);
(Continued)

(58) Field of Classification Search
CPC ......... G01N 30/6095; G01N 2030/025; G01N 2030/8881; G01N 30/66; G01N 30/02; G01N 2030/20; G01N 2030/28; G01N 30/62; G01N 25/00; B01L 3/502715; B01L 3/50273; B01L 2300/0877; B01L 2300/0861; Y10T 137/0396; B01D 63/00; B01D 15/08; B01D 15/1842; B01D 15/265; B01D 2259/40; B01D 53/0407; B01D 35/00
USPC ......................................................... 73/137
See application file for complete search history.

(56) References Cited

U.S. PATENT DOCUMENTS 3,603,134 A    9/1971  Norem
4,215,564 A *  8/1980  Lawson ................. G01N 25/18
                                                    73/25.03
(Continued)

FOREIGN PATENT DOCUMENTS

WO    2013070954    5/2013

OTHER PUBLICATIONS

ISR/WO for PCT/US14/57959 dated Mar. 11, 2015.

*Primary Examiner* — Manish S Shah
*Assistant Examiner* — Timothy Graves
(74) *Attorney, Agent, or Firm* — Rhodes IP PLC; Christopher R Rhodes

(57) ABSTRACT

Certain embodiments described herein are directed to devices that can be used to control fluid flow through one or more detectors. In some configurations, the device can be configured as a manifold that can receive a positive pressure to decouple the flow of fluid through a chromatography column from fluid flow through a detector. In certain configurations, sample flow can be accelerated into a detector cell comprising one or more filaments.

10 Claims, 73 Drawing Sheets

(51) Int. Cl.
*G01N 30/02* (2006.01)
*G01N 30/88* (2006.01)
*G01N 30/60* (2006.01)
*B01L 3/00* (2006.01)
*B01D 63/00* (2006.01)
*G01N 25/00* (2006.01)
*B01D 35/00* (2006.01)
*B01D 15/18* (2006.01)
*B01D 53/04* (2006.01)
*B01D 15/08* (2006.01)
*B01D 15/26* (2006.01)
*G01N 30/62* (2006.01)

(52) U.S. Cl.
CPC ...... *B01L 2300/0877* (2013.01); *G01N 25/00* (2013.01); *G01N 30/02* (2013.01); *G01N 30/6095* (2013.01); *G01N 2030/025* (2013.01); *G01N 2030/625* (2013.01); *G01N 2030/8881* (2013.01); *Y10T 137/0396* (2015.04)

(56) References Cited

U.S. PATENT DOCUMENTS

| | | | | |
|---|---|---|---|---|
| 4,935,040 | A * | 6/1990 | Goedert | G01N 30/20 |
| | | | | 210/198.3 |
| 6,119,710 | A * | 9/2000 | Brown | G01F 1/50 |
| | | | | 137/14 |
| 8,303,694 | B2 | 6/2012 | Tipler | |
| 2004/0250601 | A1 * | 12/2004 | Lin | G01N 30/66 |
| | | | | 73/25.03 |
| 2007/0204702 | A1 * | 9/2007 | Melcer | G01F 15/043 |
| | | | | 73/861 |
| 2012/0125083 | A1 * | 5/2012 | Hoogerwerf | G01N 30/32 |
| | | | | 73/23.42 |

* cited by examiner

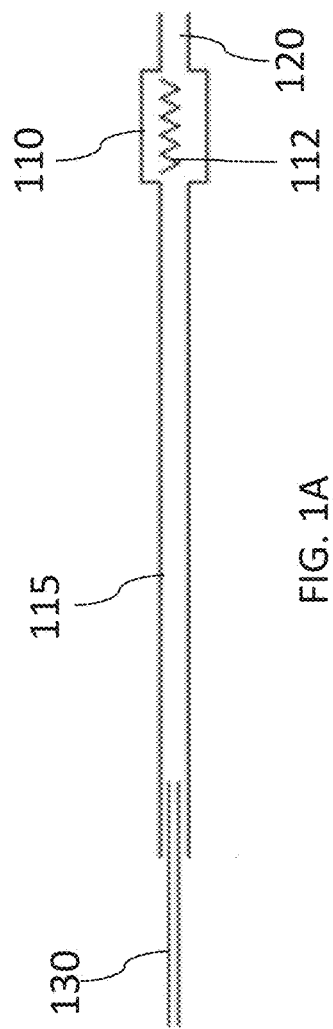
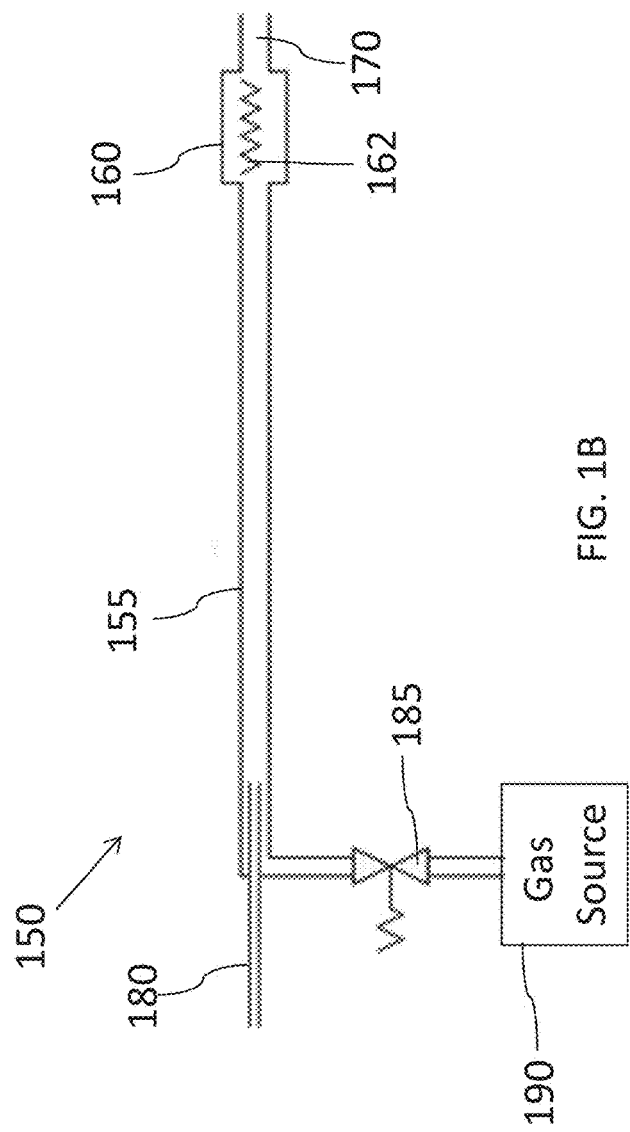

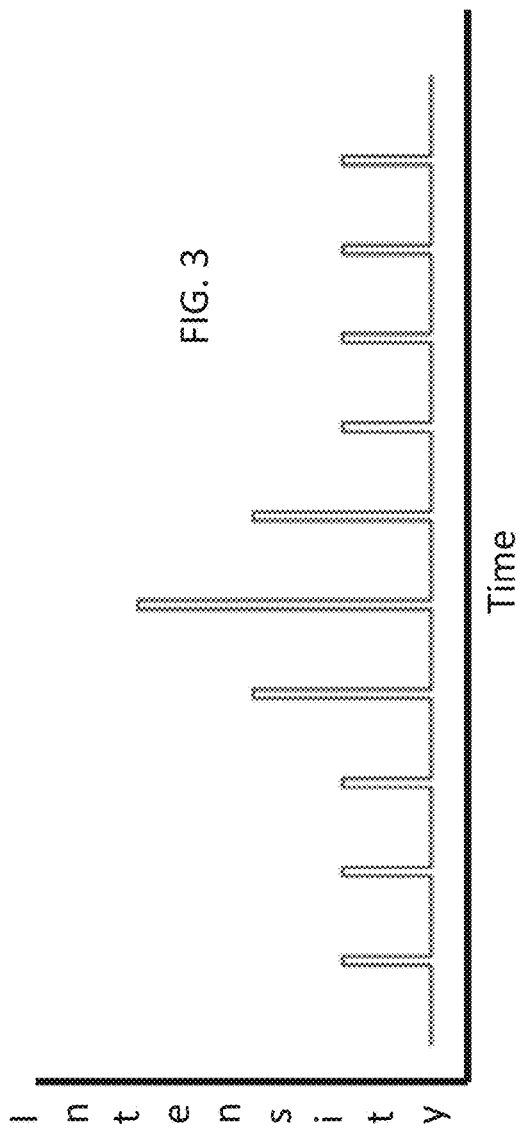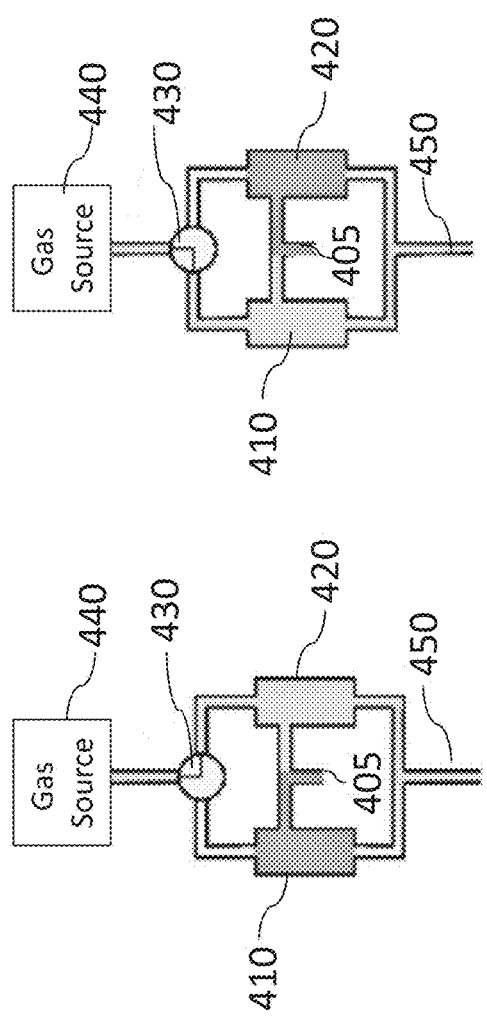

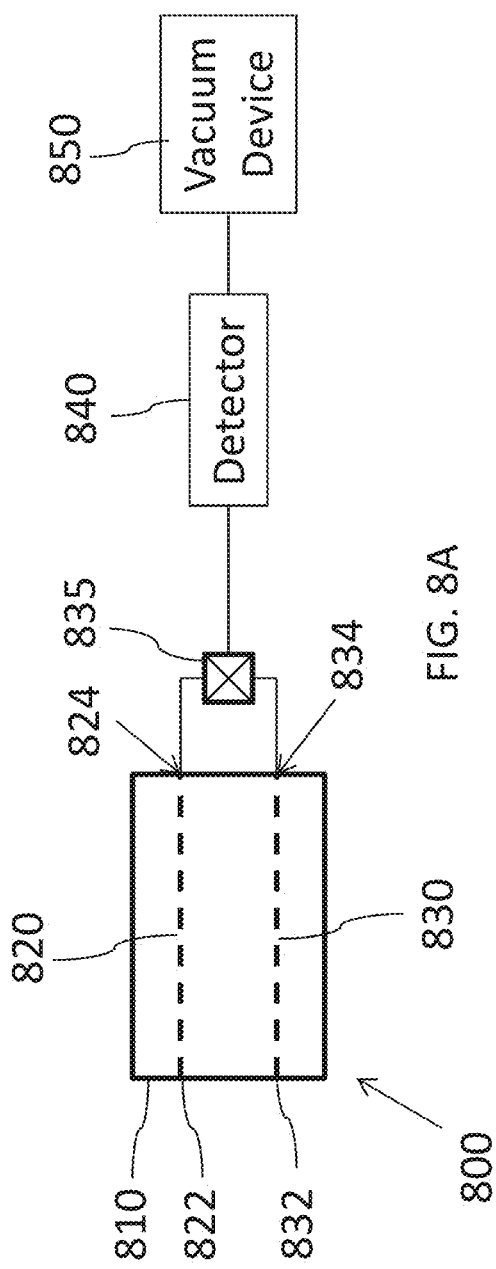
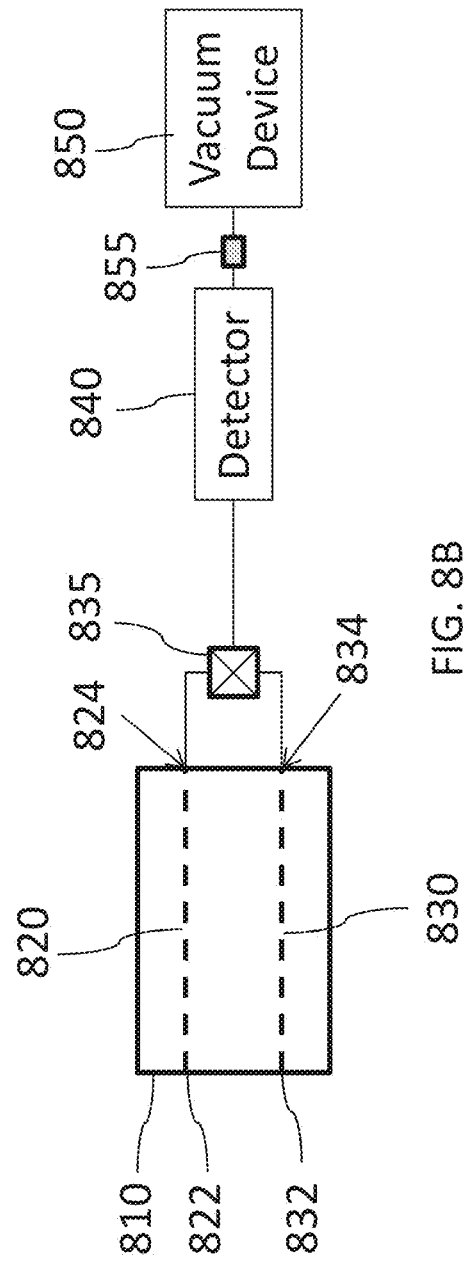

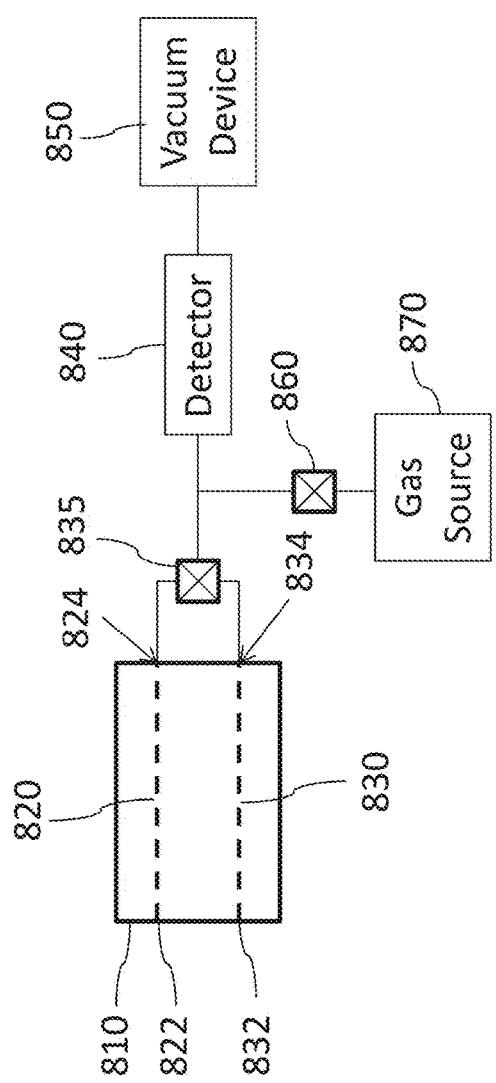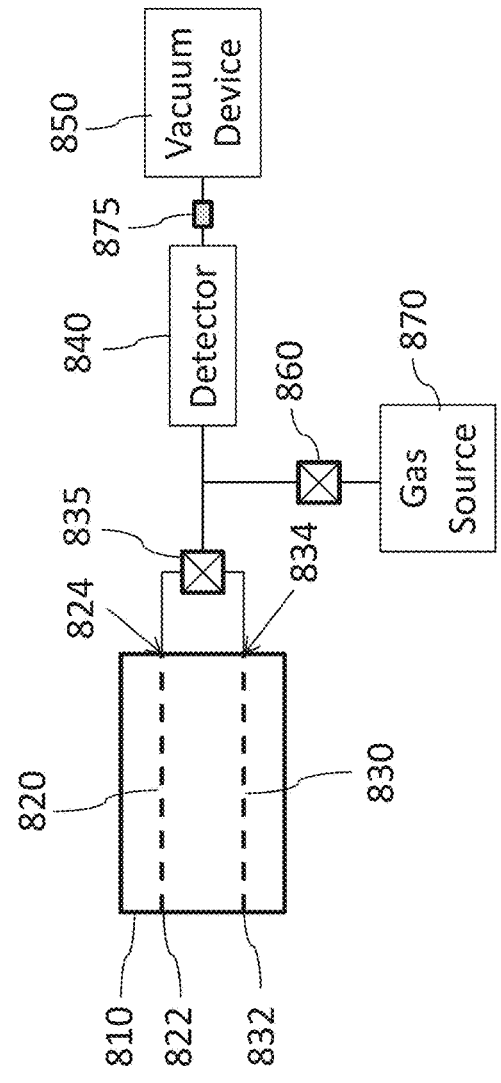

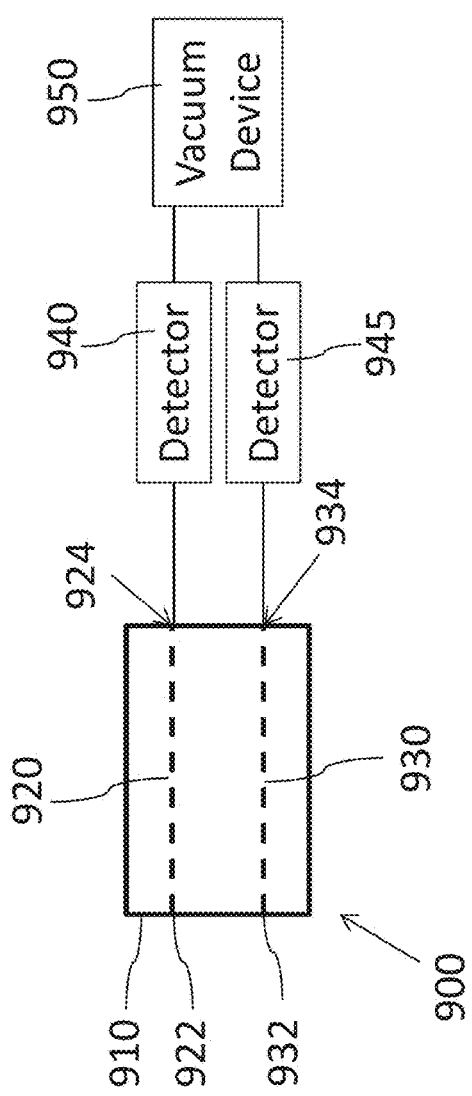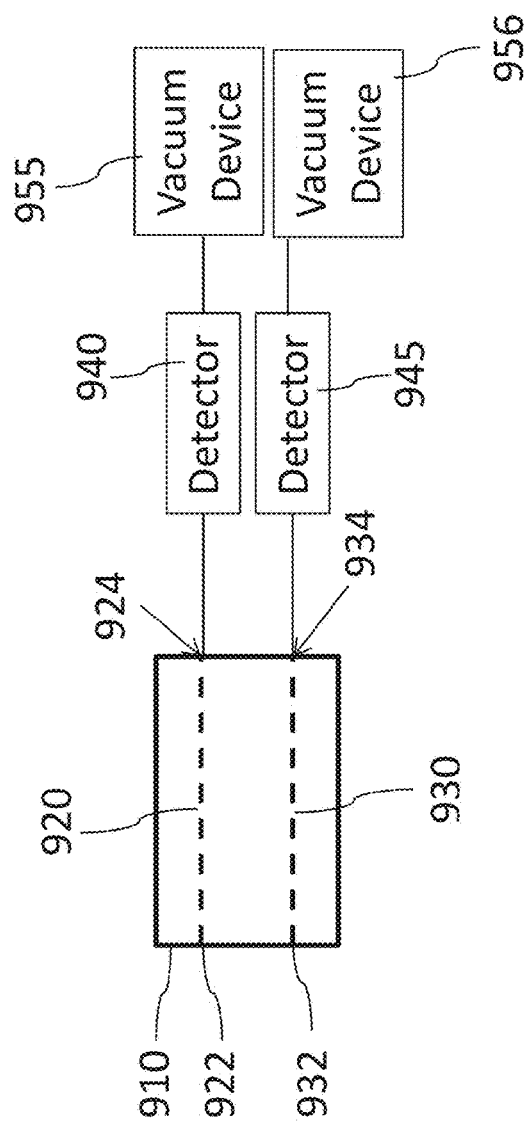

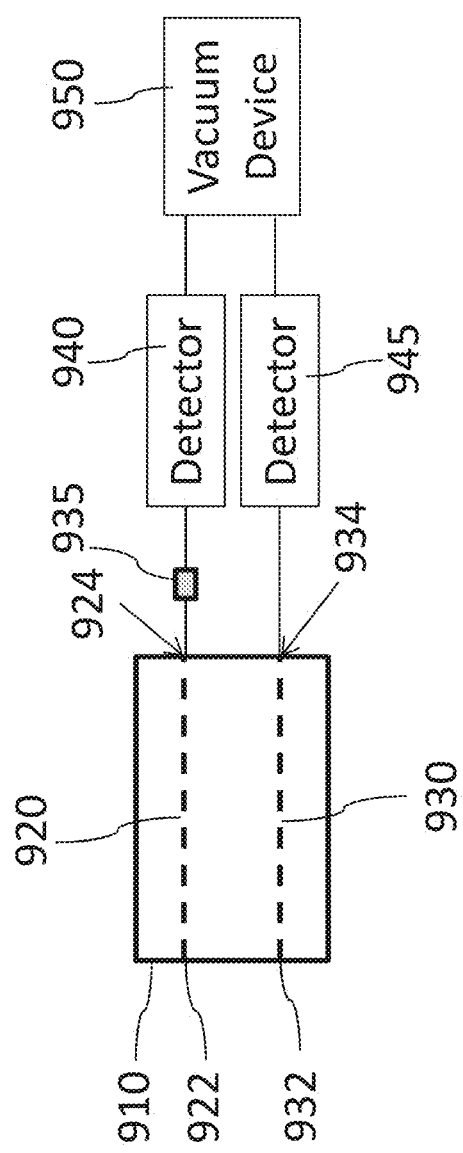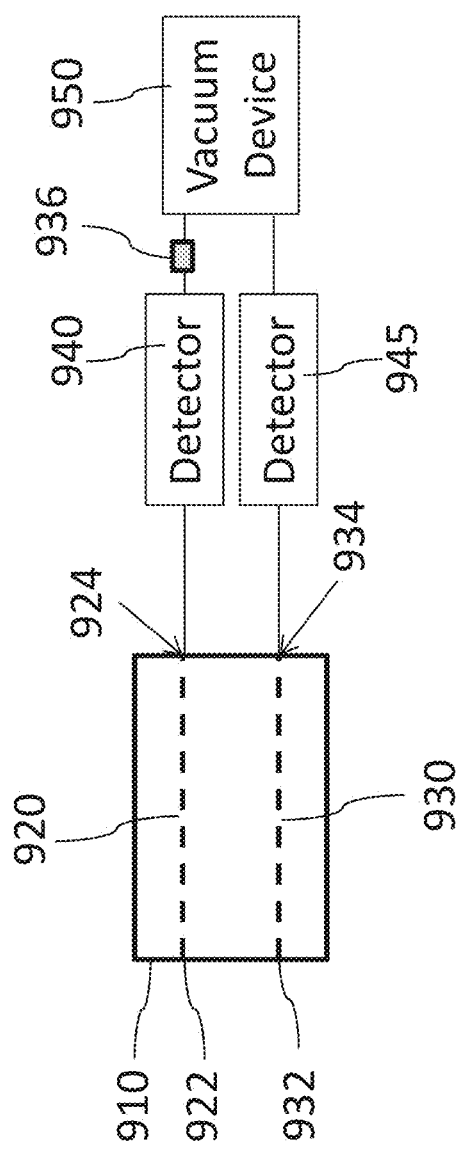

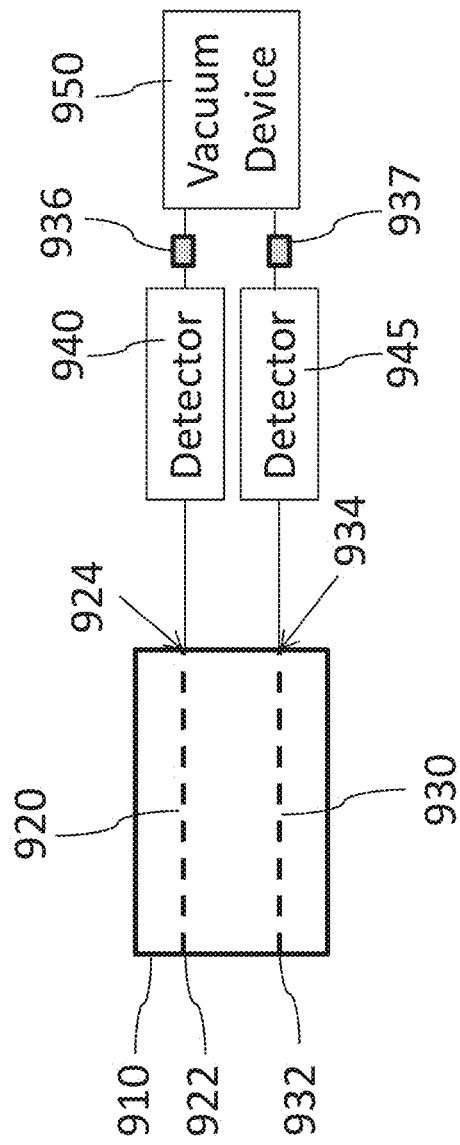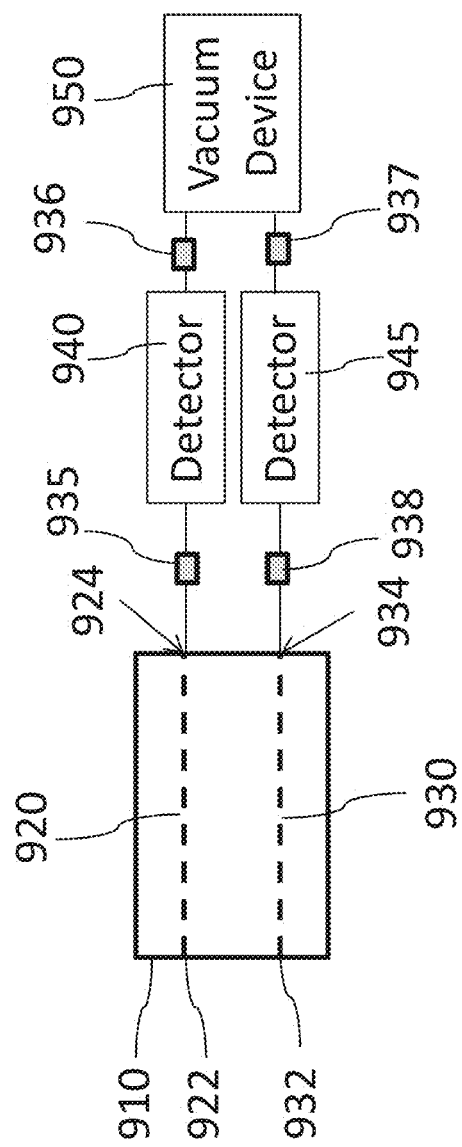

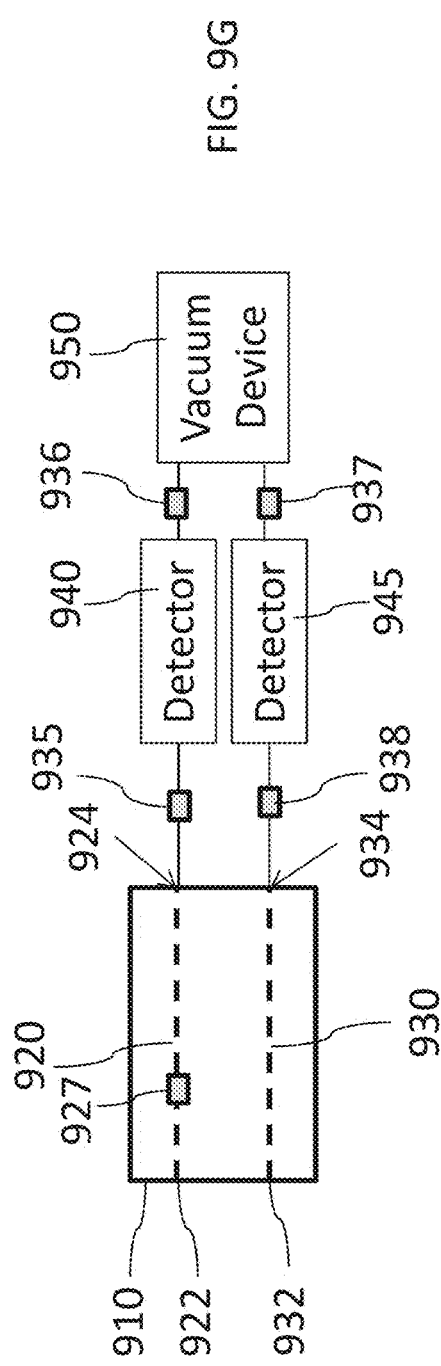
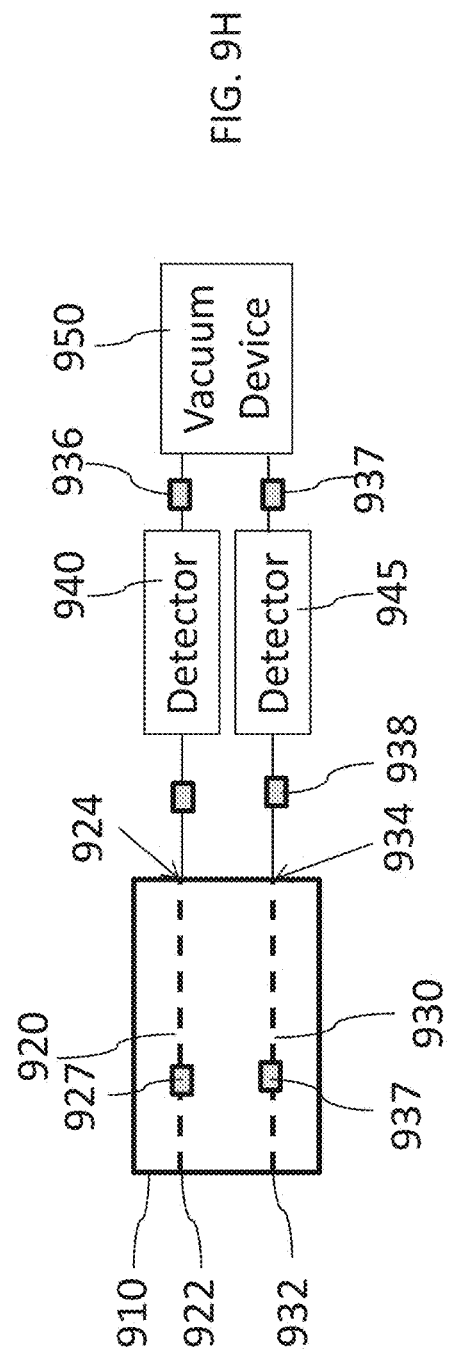

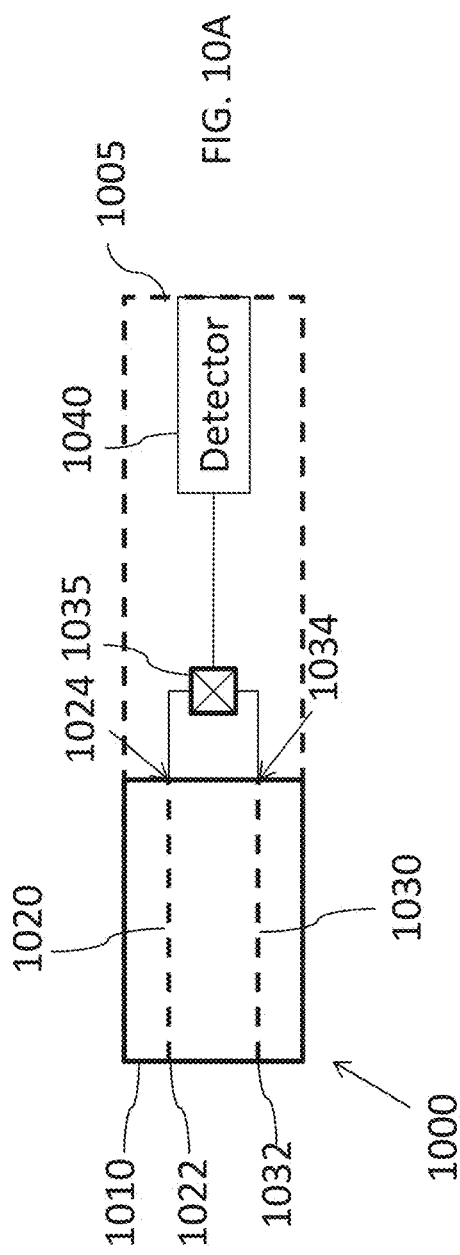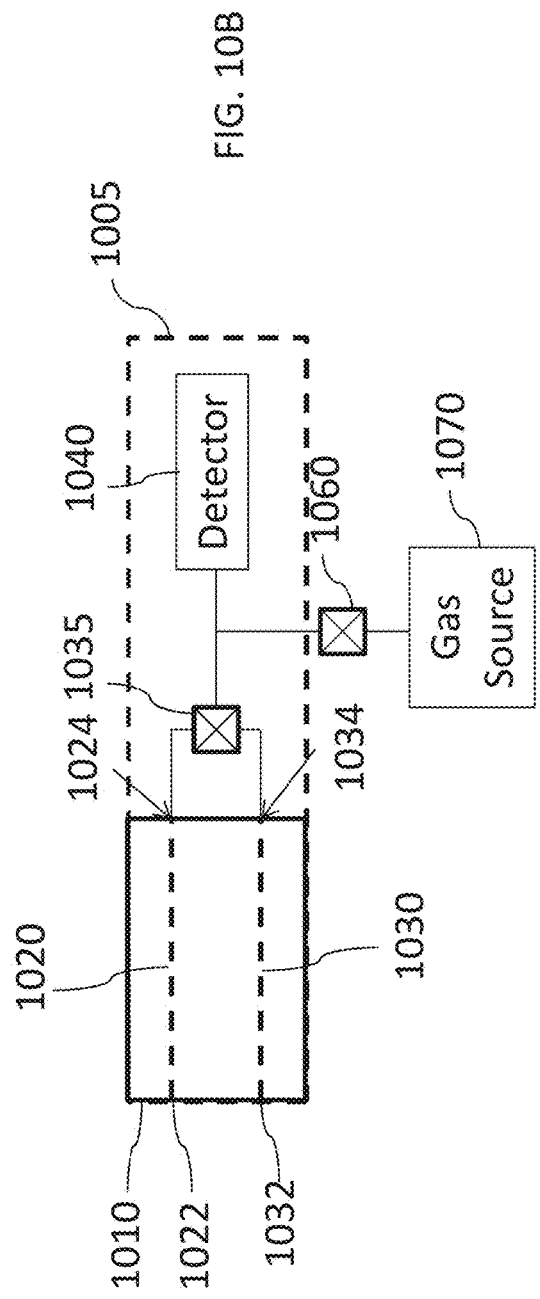

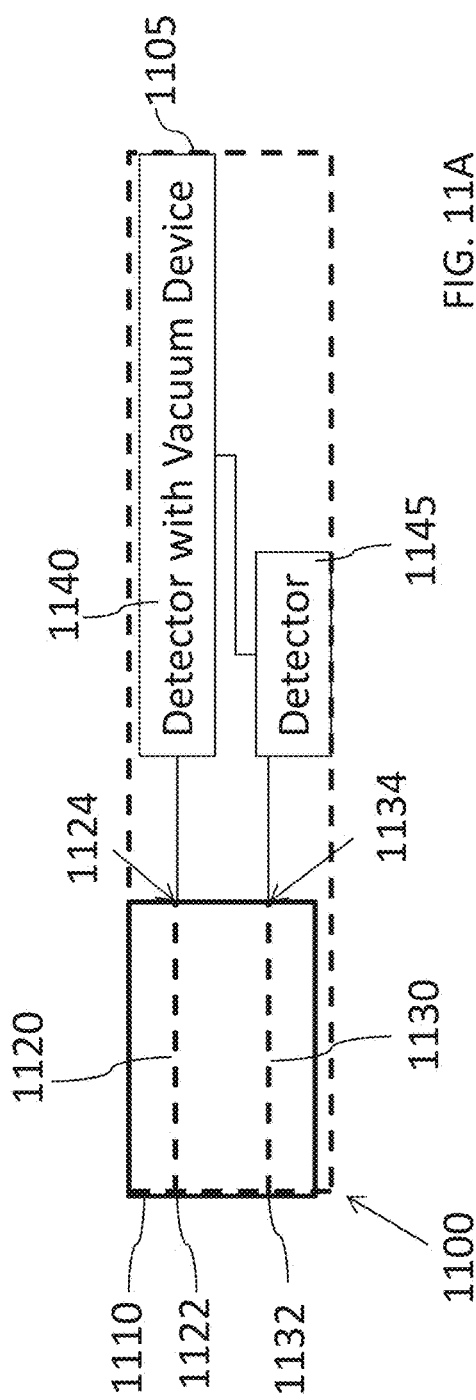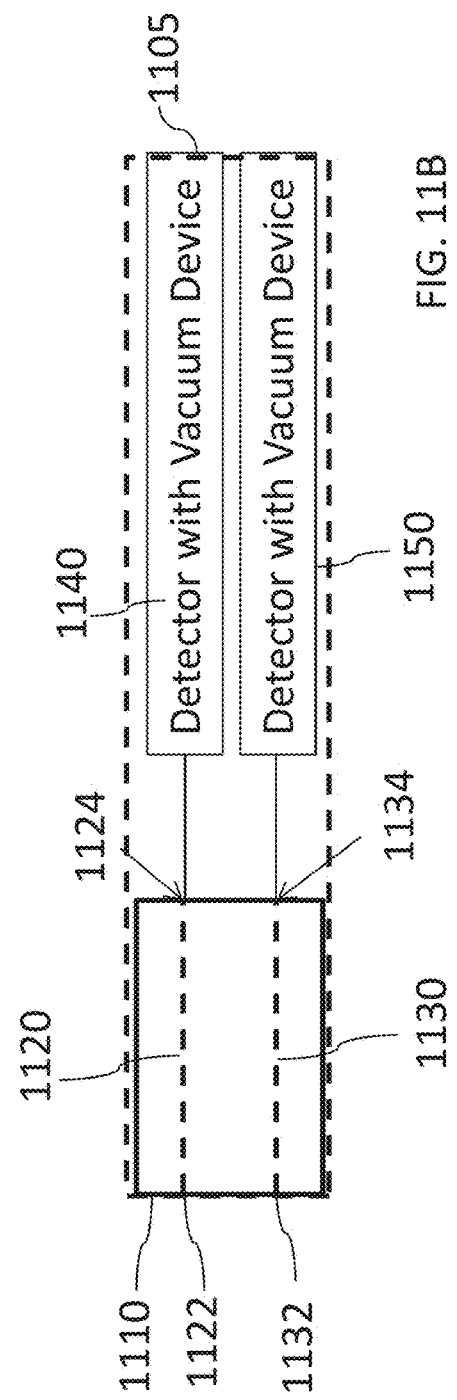

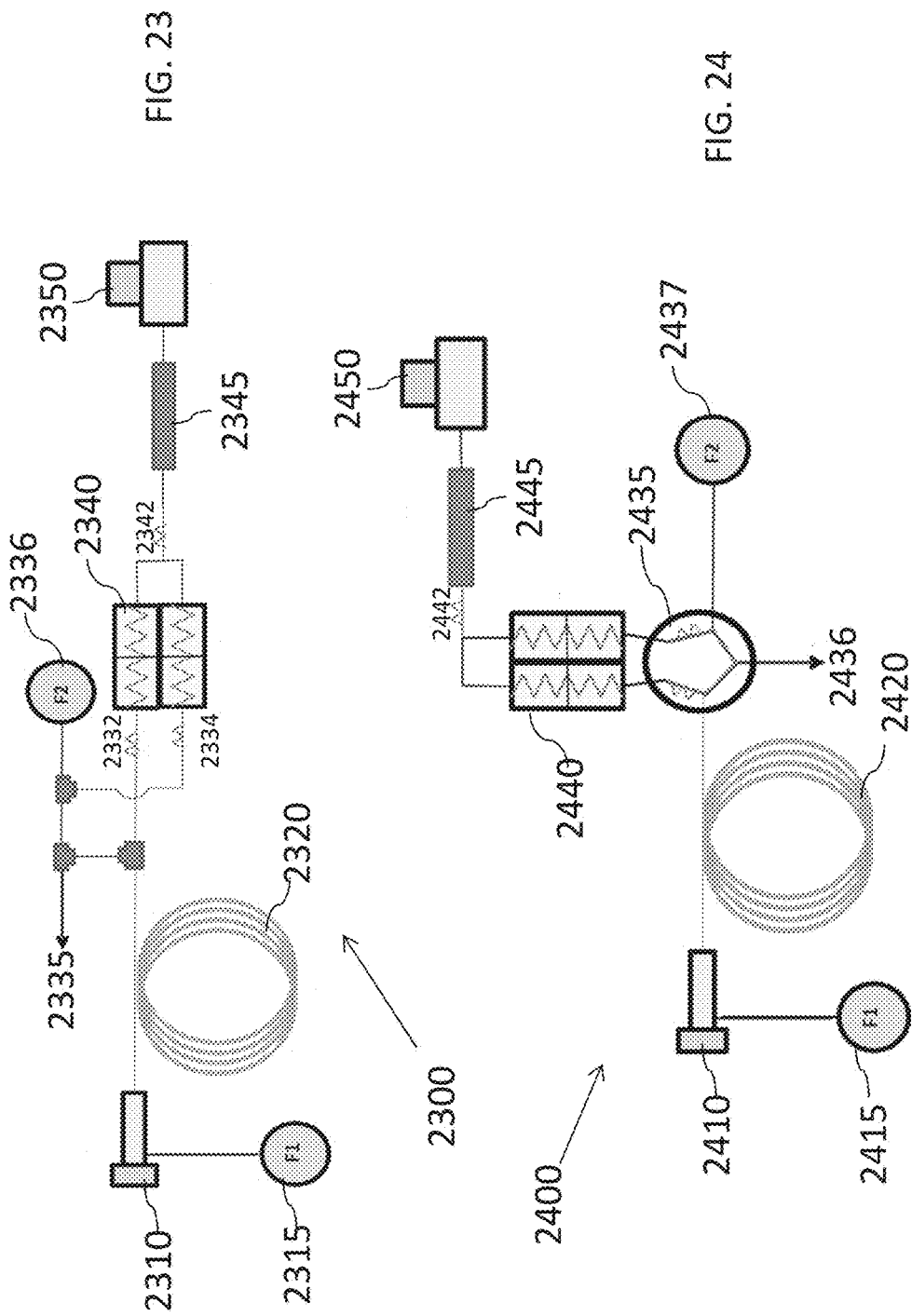

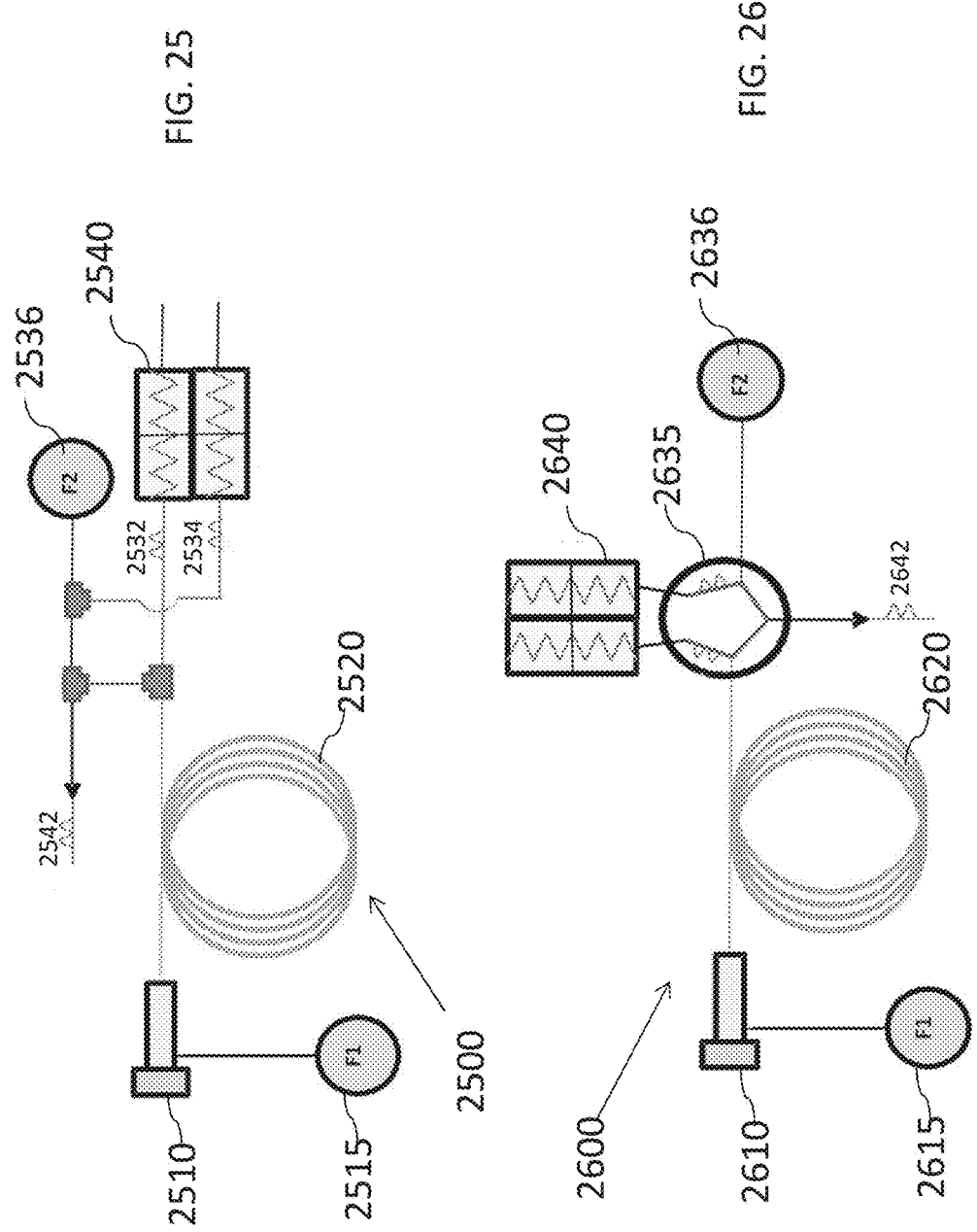

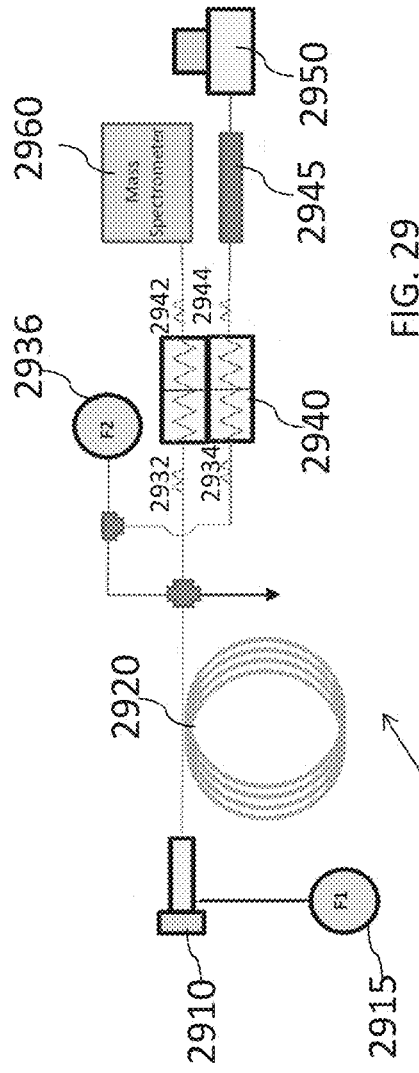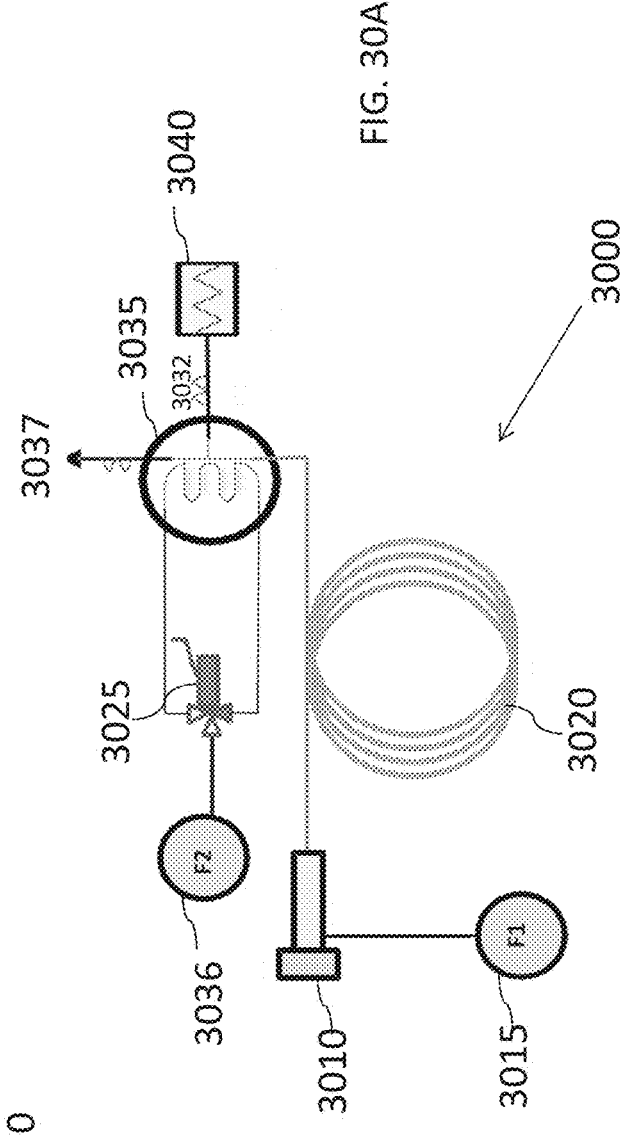

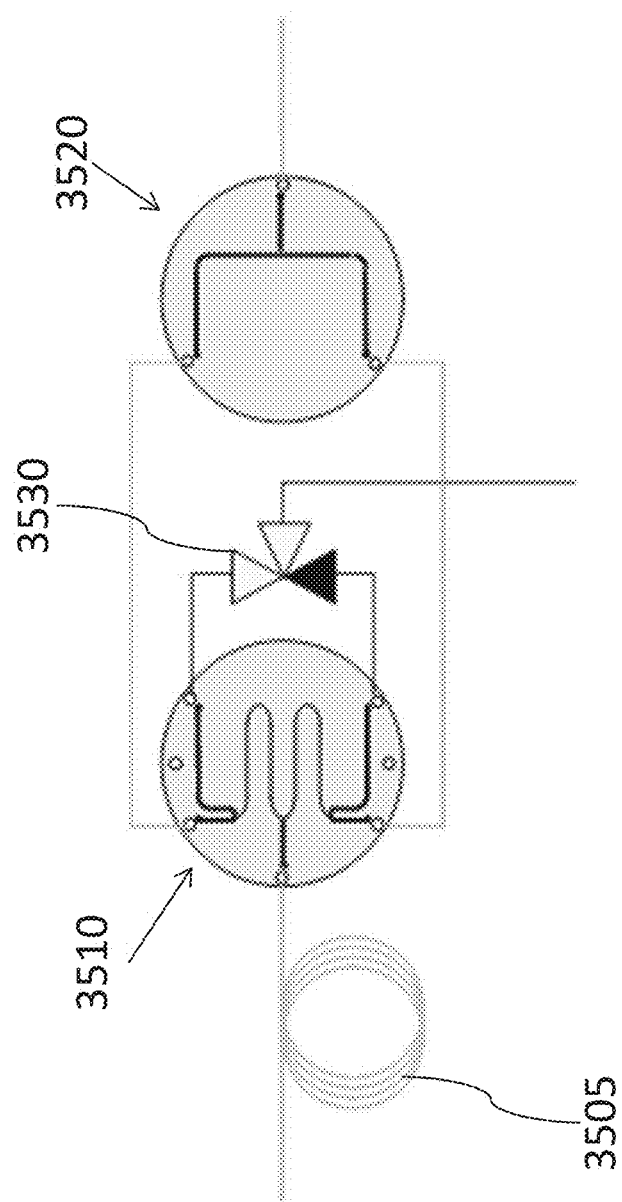

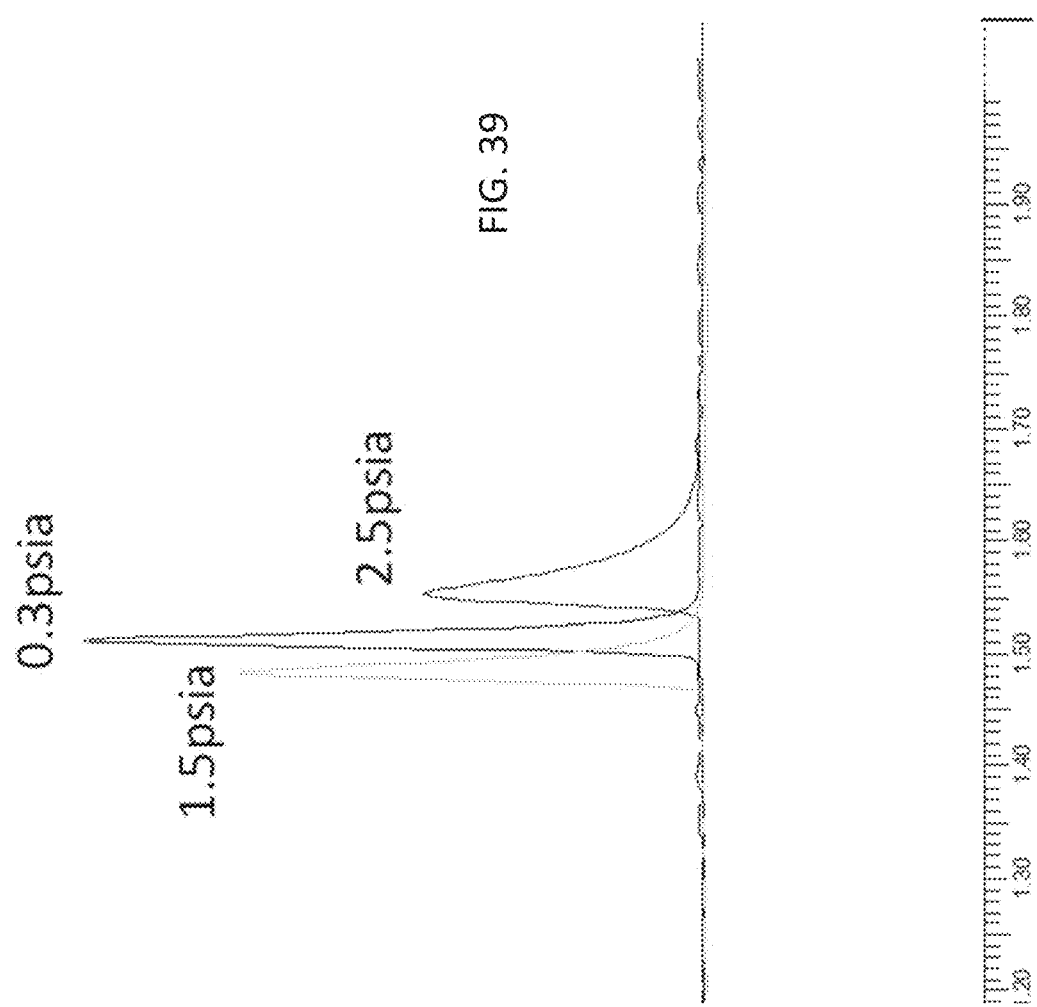

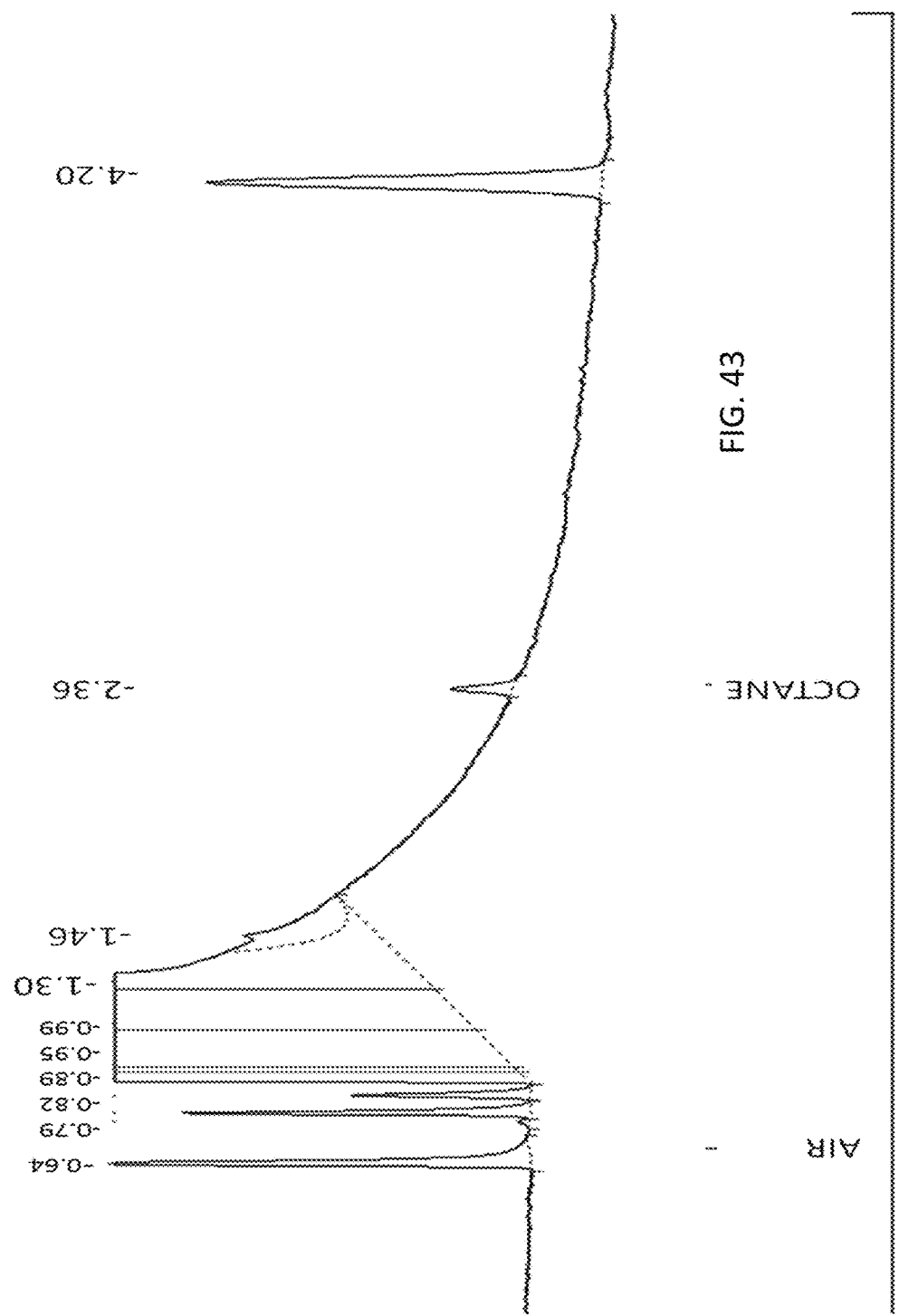

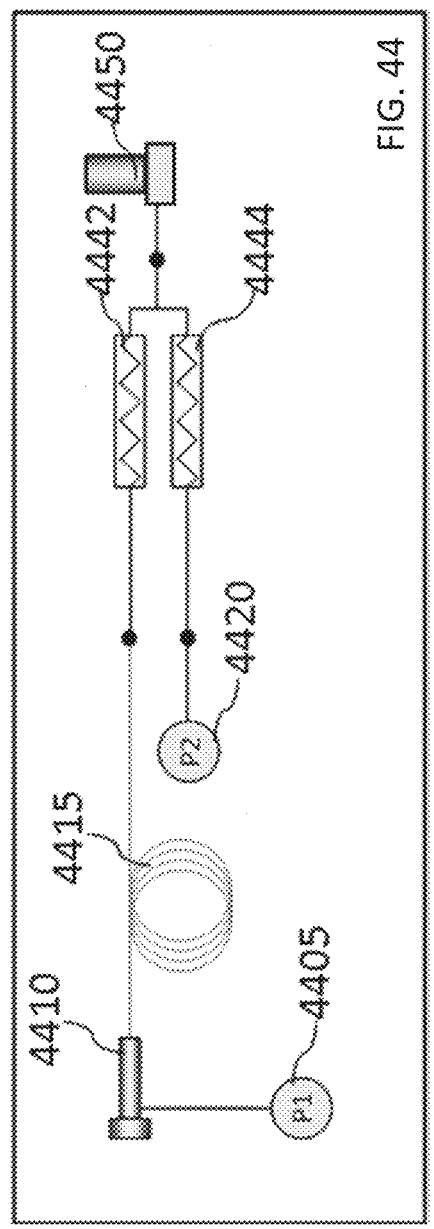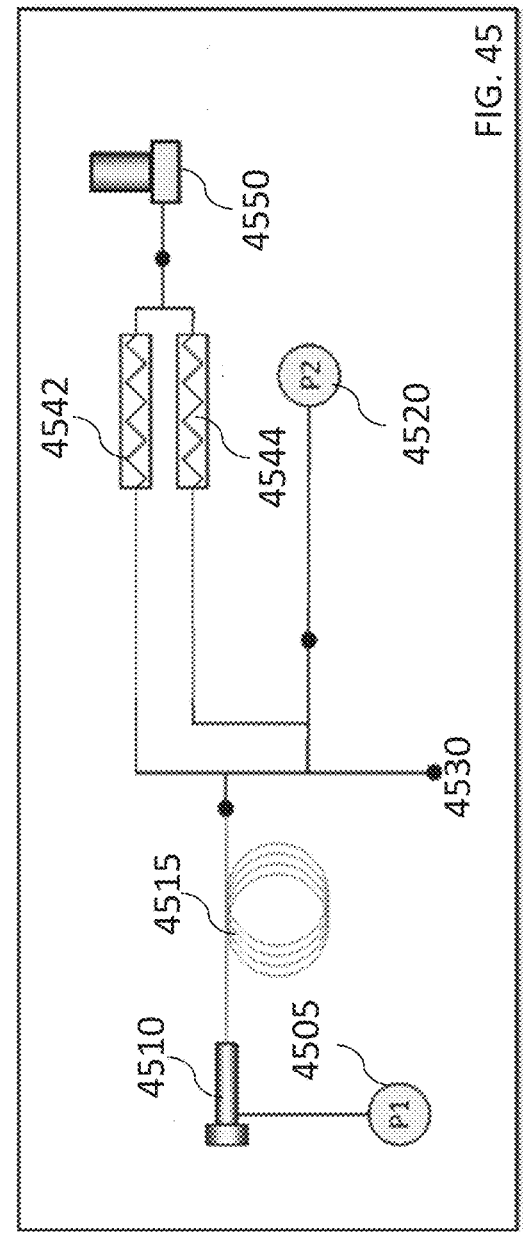

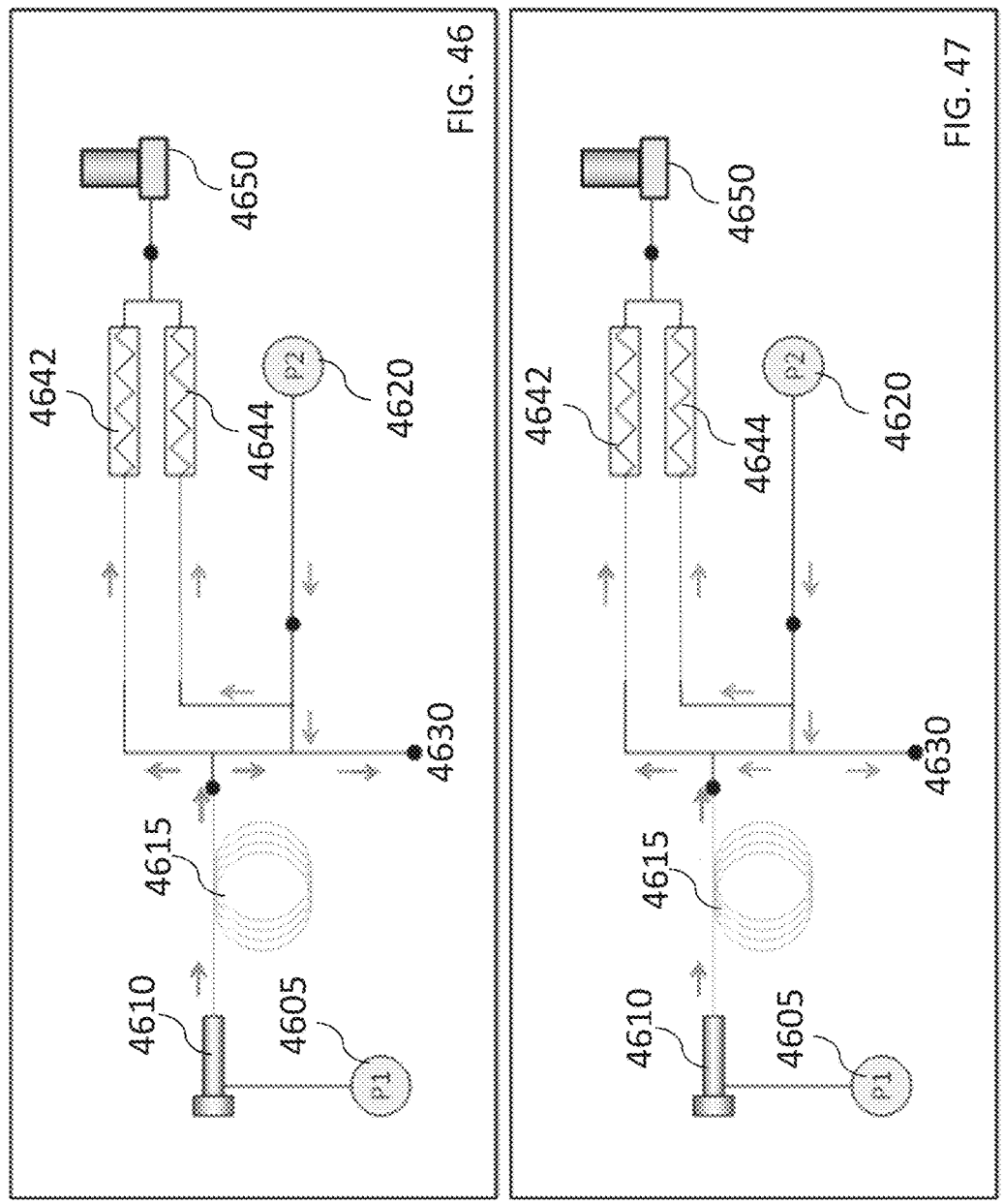

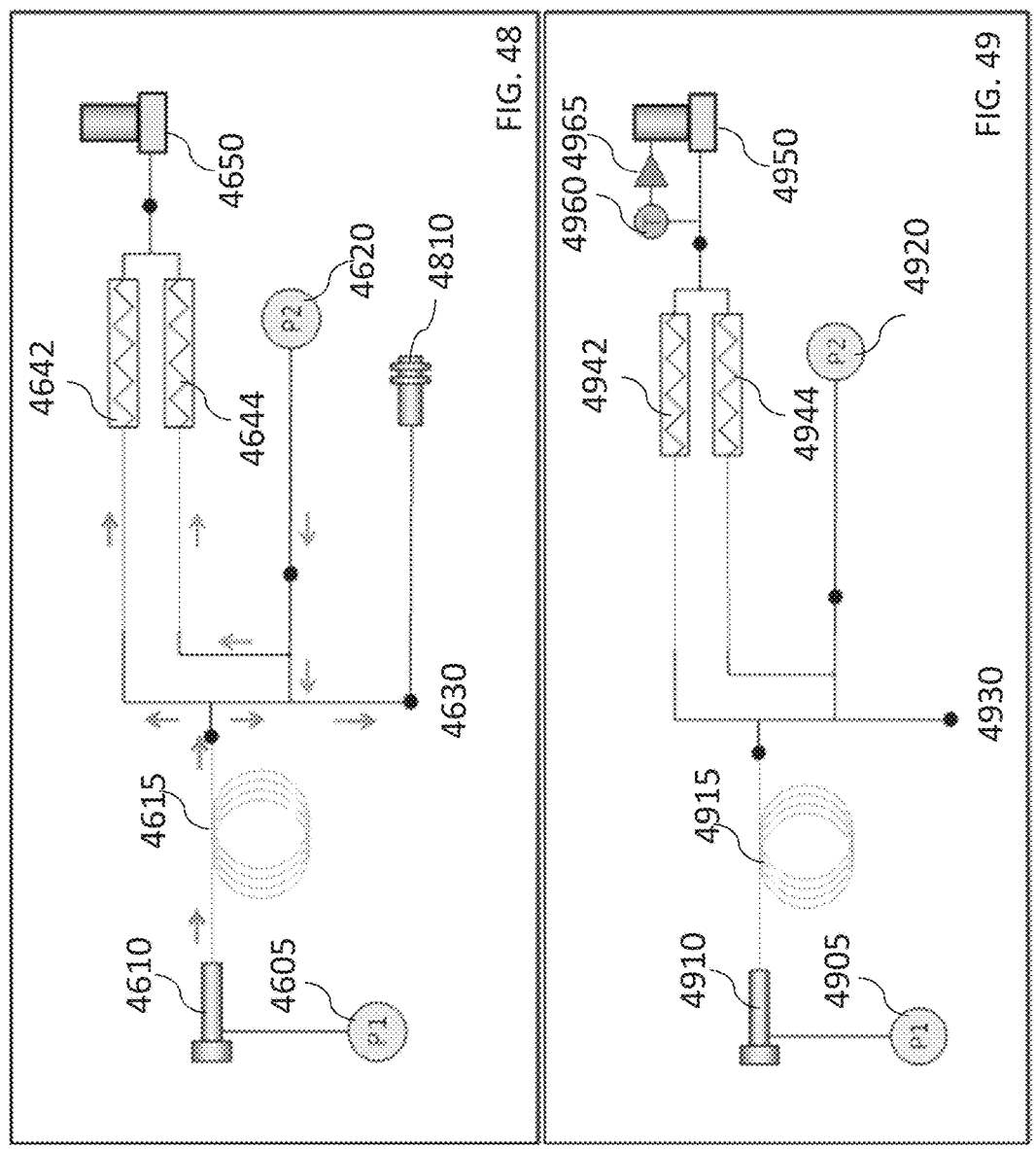

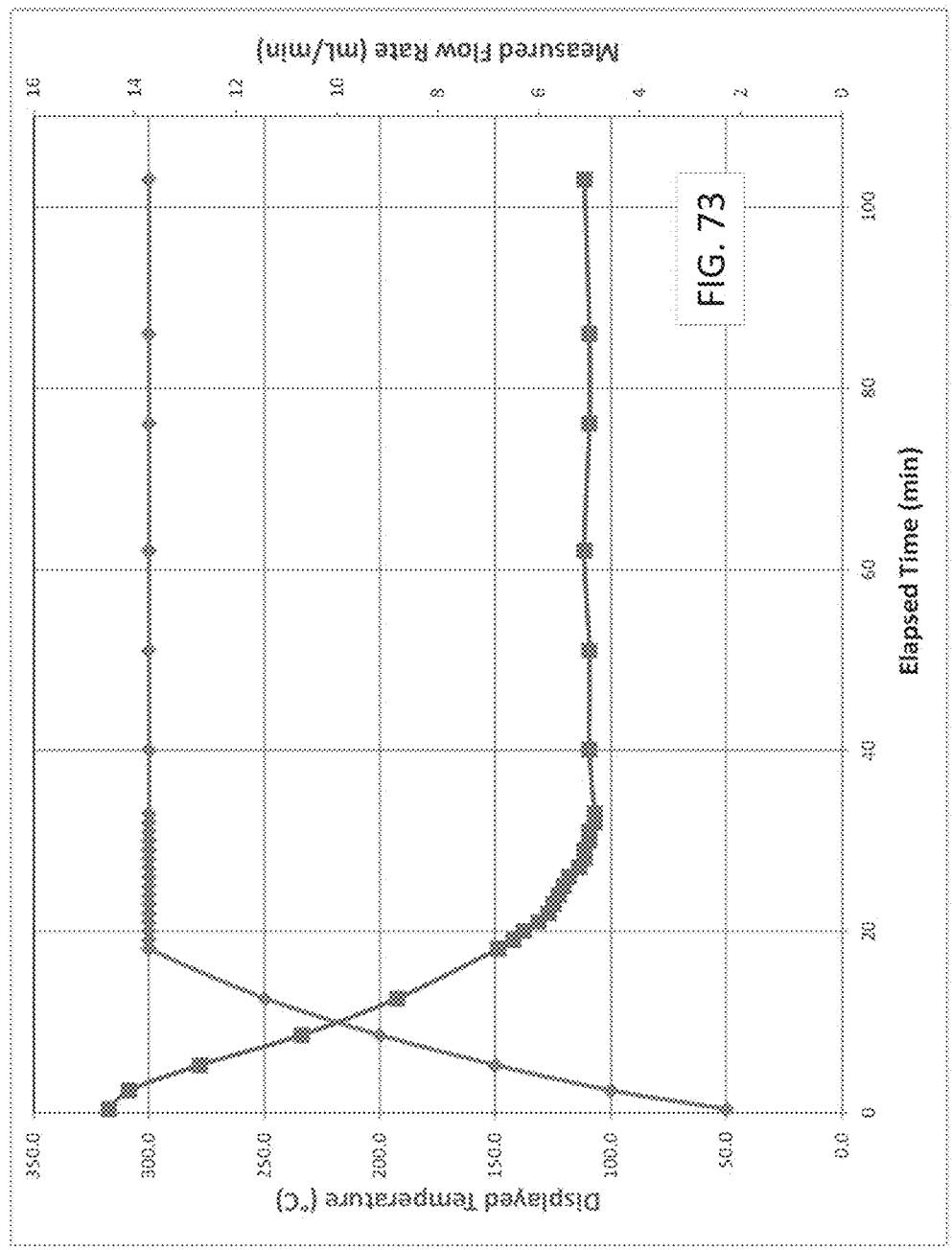

MANIFOLDS AND METHODS OF USING THEM TO CONTROL FLUID FLOWS

PRIORITY APPLICATION

This application is related to, and claims priority to, U.S. Provisional Application No. 61/883,534 filed on Sep. 27, 2013, the entire disclosure of which is hereby incorporated herein by reference for all purposes.

TECHNOLOGICAL FIELD

This application is related to manifolds and detectors. More particularly, certain embodiments described herein are directed to manifolds configured to permit decoupling of fluid flows through various portions of a chromatography system.

BACKGROUND

Chromatography separates species based on their differential solubilities in a mobile phase and a stationary phase.

SUMMARY

Certain features, aspects and embodiments described herein are directed to devices, systems and methods that comprise one or more detectors. In some configurations, the detector may be fluidically coupled to a device to provide for pressurized control of fluid flow into and/or out of the detector. In certain configurations, the detector may take the form of an integral restrictor manifold comprising one or more filaments that can be used for detection of analytes.

In one aspect, a manifold comprising a sample inlet port configured to receive effluent from a chromatography column, a vent port configured to permit exit of fluid in the manifold, and a make-up gas port configured to receive gas from a gas source is provided. In certain instances, the manifold may also comprise an analytical flow cell within the manifold and fluidically coupled to the sample inlet port through a first restrictor, a reference flow cell within the manifold and fluidically coupled to the make-up gas port through a second restrictor, wherein each of the analytical flow cell and the reference flow cell is fluidically coupled to the vent port to permit exit of fluid in the manifold, and wherein the manifold is configured to decouple fluid flow through the analytical flow cell and the reference flow cell from fluid flow through the chromatography column fluidically coupled to the sample inlet port of the manifold.

In certain configurations, each of the analytical flow cell and the reference flow cell is configured as a filament detector cell. In other instances, each of the analytical flow cell and the reference flow cell comprises two filaments. In some embodiments, each of the first restrictor and the second restrictor comprise the same internal dimensions. In additional instances, the first restrictor and the second restrictor comprise different internal dimensions. In some embodiments, each of the analytical flow cell and the reference flow cell comprises a total volume of at least 10 microliters or at least 20 microliters. In other configurations, the manifold may comprise at least one electrical connector configured to electrically couple the analytical cell and the reference cell to a processor. In other embodiments, the manifold may comprise a vacuum device fluidically coupled to the exit port. In further instances, the manifold may comprise a vent port fluidically coupled to the make-up gas port. In some embodiments, the manifold comprises an internal restrictor between the vent port and the make-up gas port, in which the internal restrictor is fluidically coupled to each of the vent port and the make-up gas port.

In another aspect, a manifold comprising first and second internal filament detectors within an integral housing is provided. In some embodiments, the manifold comprises a sample inlet port fluidically coupled to the first filament detector cell. In other configurations, the manifold further comprises a make-up gas port fluidically coupled to the second filament detector cell. In additional configurations, the manifold further comprises an exit port fluidically coupled to each of the first and second filament detector cells.

In certain examples, each of the first and second filament detectors comprises two filaments. In other examples, the manifold comprises a vent port fluidically coupled to the make-up gas port. In additional examples, the manifold comprises a first internal restrictor between the sample inlet port and the first filament detector, the first internal restrictor fluidically coupled to each of the sample inlet port and the first filament detector. In some embodiments, the manifold comprises a second internal restrictor between the make-up gas port and the second filament detector, the second internal restrictor fluidically coupled to each of the make-up gas port and the second filament detector. In certain examples, the manifold comprises a third internal restrictor between the vent port and the make-up gas port, in which the third internal restrictor is fluidically coupled to each of the vent port and the make-up gas port. In some configurations, the manifold comprises a flow controller fluidically coupled to the make-up gas port. In other instances, the manifold comprises at least one restrictor between the exit port and the first detector cell or at least one restrictor between the exit port and the second detector cell. In additional examples, each of the first detector cell and the second detector cell comprises a total volume of at least 10 microliters or at least 20 microliters. In some configurations, the manifold comprises at least one electrical connector configured to electrically couple the first detector cell and the second detector cell to a processor.

In an additional aspect, a system comprising a manifold comprising first and second internal filament detectors within an integral housing, the manifold comprising a sample inlet port fluidically coupled to the first filament detector cell through a first internal restrictor, the manifold further comprising a make-up gas port fluidically coupled to the second filament detector cell through a second internal restrictor, and the manifold further comprising an exit port fluidically coupled to each of the first and second filament detector cells, and a pressure regulator fluidically coupled to the make-up gas port is provided.

In certain configurations, the system comprises a gas source fluidically coupled to the make-up gas port through the pressure regulator. In other configurations, each of the first and second filament detectors comprises two filaments. In additional configurations, the manifold of the system further comprises a vent port fluidically coupled to the make-up gas port. In some embodiments, the manifold of the system comprises a third internal restrictor between the vent port and the make-up gas port, in which the third internal restrictor is fluidically coupled to each of the vent port and the make-up gas port. In certain examples, the system comprises a vacuum device fluidically coupled to the exit port. In other embodiments, the manifold comprises at least one restrictor between the exit port and the first detector cell or at least one restrictor between the exit port and the second detector cell. In additional configurations, each of the first detector cell and the second detector cell comprises a total volume of about 10 microliters. In other configurations, each of the first detector cell and the second detector cell comprises a total volume greater than or equal to 20 microliters. In some embodiments, the manifold further comprises at least one electrical connector configured to electrically couple the first detector cell and the second detector cell to a processor.

In another aspect, a chromatography system comprising an oven configured to receive a column to provide temperature control to the column, and a manifold configured to be placed in the oven is provided. In certain embodiments, the manifold can be fluidically coupled to the column in the oven, the manifold comprising first and second internal filament detectors within an integral housing, the manifold comprising a sample inlet port fluidically coupled to the first filament detector cell through a first internal restrictor, the manifold further comprising a make-up gas port fluidically coupled to the second filament detector cell through a second internal restrictor, and the manifold further comprising an exit port fluidically coupled to each of the first and second filament detector cells.

In certain examples, the system comprises an injector fluidically coupled to the sample inlet port of the manifold through the chromatography column. In other examples, the manifold of the system comprises a vent port fluidically coupled to the make-up gas port. In some embodiments, the manifold further comprises a third internal restrictor between the vent port and the make-up gas port, in which the third internal restrictor is fluidically coupled to each of the vent port and the make-up gas port. In some examples, the first detector cell is configured as a thermal conductivity detector cell. In other embodiments, the second detector is configured as a thermal conductivity detector. In some examples, the first detector cell is configured as a two filament detector. In other embodiments, the second detector cell is configured as a two filament detector. In further instances, the system may comprise an additional detector fluidically coupled to the exit port of the manifold. In other instances, the additional detector comprises a mass spectrometer.

In another aspect, a method of analyzing an analyte in a chromatography system comprising a separation column and a detector is provided. In some examples, the method comprises fluidically decoupling analyte fluid flow through the separation column of the chromatography system and analyte fluid flow through the detector of the chromatography system using a manifold comprising the detector, and controlling analyte fluid flow into the detector of the manifold.

In some embodiments, the method comprises controlling analyte fluid flow into the detector by applying a negative pressure to an outlet of the manifold using a vacuum device. In other embodiments, the method comprises controlling analyte fluid flow into the detector by applying a positive pressure to an inlet of the manifold. In further instances, the method comprises configuring the manifold with a sample inlet port configured to receive effluent from the separation column, a make-up gas port configured to receive a make-up gas to apply a positive pressure within the manifold and with a vent port configured to permit exit of effluent from the manifold. In certain examples, the method comprises configuring the manifold to comprise a first restrictor between the sample inlet port and an analytical cell comprising a filament detector. In additional embodiments, the method comprises configuring the manifold to comprise a second restrictor between the make-up gas port and a reference cell comprising a filament detector. In some examples, each of the analytical cell and the reference cell is a configured as a two filament detector. In certain embodiments, the method comprises regulating pressure in the manifold by fluidically coupling a pressure regulator to the make-up gas port of the manifold. In some embodiments, the method comprises applying the positive pressure in pulses. In certain examples, the method comprises applying the positive pressure continuously.

In another aspect, a method of analyzing an analyte in a chromatography system comprising a separation column and a detector, the method comprising fluidically decoupling analyte fluid flow through the separation column of the chromatography system and analyte fluid flow through a manifold comprising a filament detector cell, and controlling analyte fluid flow into the filament detector cell by applying a positive pressure to the manifold using a make-up gas fluidically coupled to the manifold is provided.

In certain embodiments, the method comprises applying the positive pressure using pulses of make-up gas. In other embodiments, the method comprises applying the positive pressure continuously. In some configurations, the method comprises coupling the manifold to the separation column through a sample inlet port on the manifold, in which the sample inlet port is fluidically coupled to an analytical filament cell within the manifold through a first internal restrictor. In further embodiments, the method comprises coupling the manifold to the make-up gas through a make-up gas port of the manifold, in which the make-up gas port is fluidically coupled to a reference filament cell within the manifold through a second internal restrictor. In other embodiments, the method comprises venting fluid in the manifold through an exit port in the manifold, in which the exit port is fluidically coupled to the analytical filament cell and the reference filament cell. In some examples, the method comprises configuring the manifold with an analytical filament cell detector and a reference filament cell detector. In additional instances, the method comprises accelerating flow of fluid into the filament detector by fluidically coupling a vacuum device to the manifold. In other examples, the method comprises configuring the filament detector is a thermal conductivity detector. In further examples, the method comprises configuring the filament detector as a two filament detector.

In an additional aspect, a method of decoupling sample fluid flow through a column and through a flow cell detector of a chromatography system, the method comprising providing a manifold comprising first and second internal filament detectors within an integral housing, the manifold comprising a sample inlet port fluidically coupled to the first filament detector cell through a first internal restrictor, the manifold further comprising a make-up gas port fluidically coupled to the second filament detector cell through a second internal restrictor, and the manifold further comprising an exit port fluidically coupled to each of the first and second filament detector cells is described. In some instances, the method comprises providing instructions for using the manifold with a gas chromatography device.

In certain embodiments, the method comprises providing a vacuum device. In other instances, the method comprises providing a pressure regulator. In further embodiments, the method comprises providing an injector. In additional embodiments, the method comprises providing the gas chromatography device. In some embodiments, the method comprises providing a separation column.

In another aspect, a system comprising an interface or manifold comprising a first fluid input port, a first fluid outlet port and a first fluid flow path between the first fluid input port and the first fluid output port, and a second fluid input port, a second fluid outlet port and a second fluid flow path between the second fluid input port and the second fluid output port, a detector and a vacuum device is provided. In some configurations, the detector is fluidically coupled to the first fluid flow path and the second fluid flow path through a switching valve. For example, the switching valve can be configured to permit fluid flow from the first fluid flow path into the detector in a first position and to permit fluid flow from the second fluid flow path into the detector in a second position. In some instances, the vacuum device is fluidically coupled to the detector to accelerate flow of fluid from the interface into the detector.

In certain examples, the manifold is fluidically coupled to a device configured to accelerate flow of sample into the detector. In some embodiments, the device may be between the interface and the detector. For example, the device may be fluidically coupled to a fluid flow path between the switching valve and the detector and is configured to modulate between at least two positions, e.g., the device may be a valve such as a solenoid valve. In some configurations, the device is fluidically coupled to a gas source, in which actuation of the modulating device to a first position fluidically couples the gas source to the detector and in which actuation of the device to a second position fluidically decouples the gas source and the detector. In some instances, one or more restrictors may be present in the system. For examples, a restrictor may be present between the detector and the vacuum device, between the switching valve and the detector or between other components. The restrictor may be a fixed inner diameter restrictor or may be adjustable, e.g., may be a needle valve. In some instances, the detector may comprise an internal restrictor. As described herein, the interface can be configured as a microfluidic device, in which each of the first flow path and the second fluid flow path is configured as an internal microchannel within the microfluidic device. A microfluidic device generally comprises microchannels and/or charging chambers within the microfluidic device and may be constructed from a plurality of wafers which are laminated together. Illustrative methods of producing microfluidic devices are described, for example, in commonly owned U.S. Pat. No. 8,303,694, the entire disclosure of which is hereby incorporated herein by reference. In some instances, at least one of the first and second fluid flow paths comprises a restrictor. The detector of the system can vary and in some configurations the detector comprises at least one filament.

In an additional aspect, a device or system comprising an interface or manifold comprising a first fluid flow path between a first fluid input port and a first fluid outlet port and a second fluid flow path between a second fluid input port and a second fluid outlet port is provided. In some configurations, the system further comprises a first detector fluidically coupled to the first fluid flow path, a second detector fluidically coupled to the second fluid flow path, and a vacuum device fluidically coupled to the first detector and the second detector to accelerate flow of fluid from the interface into the first detector and into the second detector.

In some configurations, the device or system may comprise a first modulating device configured to fluidically couple to the first detector, in which the first modulating device is configured to accelerate flow of sample into the first detector. In some instances, the first modulating device is configured as a 3-way solenoid valve. In other instances, the system may comprise a second modulating device configured to fluidically couple to the second detector, in which the second modulating device is configured to accelerate flow of sample into the second detector. In some examples, the second modulating device is configured as a 3-way solenoid valve. If desired, one or more restrictors may be present. For example, a restrictor between the first detector and the vacuum device, between the second detector and the vacuum device, between the first fluid flow path and the first detector, between the second fluid flow path and the second detector or in other places. In some configurations, at least one of the first detector and the second detector comprises an internal restrictor. If desired, the system can be configured as a microfluidic device, in which each of the first flow path and the second fluid flow path is configured as an internal microchannel within the microfluidic device. In some embodiments, at least one of the first and second fluid flow paths in the microfluidic device comprises a restrictor. The detector of the system can vary and in some configurations the detector comprises at least one filament.

In another aspect, a device comprising an interface or manifold comprising a first fluid flow path between a first fluid input port and a first fluid outlet port and second fluid flow path between a second fluid input port and a second fluid outlet port is provided. In some examples, the device further includes a detector fluidically coupled to the first fluid flow path and the second fluid flow path through a switching valve, the switching valve configured to permit fluid flow from the first fluid flow path into the detector in a first position and to permit fluid flow from the second fluid flow path into the detector in a second position, in which the detector comprises a vacuum device configured to permit operation of the detector at a pressure less than atmospheric pressure, in which the vacuum device is fluidically coupled to the interface to accelerate flow of fluid from the interface into the detector.

In certain embodiments, the interface or manifold is fluidically coupled to a modulating device configured to accelerate flow of sample into the detector. The modulating device can be positioned in many different places, e.g., may be between the interface and the detector or between other components. In some configurations, the modulating device is configured to modulate between at least two positions, e.g., is a valve such as, for example, a solenoid valve.

In some instances, one or more restrictors may be present, e.g., a restrictor may be present between the detector and the vacuum device of the detector, between the switching valve and the detector, in at least one of the first fluid flow path and the second fluid flow path, in the detector or other positions. In some examples, the interface is configured as a microfluidic device, in which each of the first flow path and the second fluid flow path is configured as an internal microchannel within the microfluidic device. If desired, at least one the first and second fluid flow paths of the microfluidic device comprises a restrictor. Many different types of detectors may be present, e.g., a detector comprising a filament may be present.

In an additional aspect, a system or device comprising an interface or manifold comprising a first fluid flow path between a first fluid input port and a first fluid outlet port and second fluid flow path between a second fluid input port and a second fluid outlet port, a first detector fluidically coupled to the first fluid flow path, and a second detector fluidically coupled to the second fluid flow path, in which the second detector comprises a vacuum device configured to permit operation of the second detector at a pressure less than atmospheric pressure, in which the vacuum device is fluidically coupled to the first detector and the second detector to accelerate flow of fluid from the interface into the first detector and into the second detector is provided.

In certain embodiments, the device may comprise a first modulating device configured to fluidically couple to the first detector, in which the first modulating device is configured to accelerate flow of sample into the first detector. In other examples, a second modulating device configured to fluidically couple to the second detector, in which the second modulating device is configured to accelerate flow of sample into the second detector may be present. In some instances, one or both of the first and second modulating devices can be configured as a solenoid valve. In some examples, one or more restrictors may be present, e.g., a restrictor may be present between a flow cell of the second detector and the vacuum device of the first detector, between a flow cell of the first detector and the vacuum device of the second detector, between the first fluid flow path and the first detector, between the second fluid flow path and the second detector, in one or both of the detectors or in other positions and/or combinations of these positions. In some examples, the interface is configured as a microfluidic device, in which each of the first flow path and the second fluid flow path is configured as an internal microchannel within the microfluidic device. If desired, at least one the first and second fluid flow paths of the microfluidic device comprises a restrictor. Many different types of detectors may be present, e.g., a detector comprising a filament may be present. In some instances, the first detector and the second detector may be the same, whereas in other instances, the first detector and the second detector may be different.

In another aspect, a system comprising a microfluidic device comprising an internal microchannel comprising a first charging chamber and a second charging chamber, the first charging chamber and the second charging chamber each fluidically coupled to an inlet port and an outlet port of the microfluidic device, and a switching valve fluidically coupled to the first and second charging chambers and the outlet port, the switching valve configured to permit flow of fluid from the first charging chamber in a first position and to permit flow from the second charging chamber in a second position, a detector fluidically coupled to the outlet port of the microfluidic device, and a vacuum device fluidically coupled to the detector to accelerate flow of fluid from the outlet port of the microfluidic device into the detector is provided.

In certain examples, the system is fluidically coupled to a modulating device configured to accelerate flow of sample into the detector. In some configurations, the system may comprise a modulating device between the interface and the detector. In other configurations, the modulating device is fluidically coupled to a fluid flow path between the switching valve and the detector and is configured to modulate between at least two positions. In some examples, the modulating device is configured as a solenoid valve. In certain configurations, the system may comprise a restrictor between the detector and the vacuum device. In some embodiments, the restrictor comprises a needle valve or a restrictor whose inner diameter may be adjusted. In some examples, the system may include a modulating device between the interface and the detector, e.g., the modulating device is fluidically coupled to a fluid flow path between the switching valve and the detector and is configured to modulate between at least two positions. In some embodiments, the modulating device may be a solenoid valve. In other examples, the modulating device is fluidically coupled to a gas source, in which actuation of the modulating device to a first position fluidically couples the gas source to the detector and in which actuation of the modulating device to a second position fluidically decouples the gas source and the detector. In some instances, one or more restrictors may be present, e.g., a restrictor may be present between the switching valve and the detector, in at least one of the first fluid flow path and the second fluid flow path, in the detector, between the first fluid outlet port and the switching valve, between the second fluid outlet port and the switching valve or in other positions. In some embodiments, the microfluidic device is configured as a plurality of wafers which are laminated to each other to provide the internal microchannel and the first and second charging chambers. If desired, one or more restrictors may be present in the internal microchannel. Numerous different types of detectors may be present, e.g., a detector comprising a filament may be present.

In an additional aspect, a system comprising a microfluidic device comprising an internal microchannel comprising a first charging chamber and a second charging chamber, the first charging chamber and the second charging chamber each fluidically coupled to an inlet port of the microfluidic device, the first charging chamber fluidically coupled to a first outlet port and the second charging chamber fluidically coupled to a second outlet port, a first detector fluidically coupled to the first outlet port of the microfluidic device, a second detector fluidically coupled to the second outlet port of the microfluidic device, and a vacuum device fluidically coupled to the first detector and the second detector and configured to accelerate flow of fluid from the microfluidic device into the first detector and into the second detector is disclosed.

In certain embodiments, the system comprises a first modulating device, e.g., a solenoid valve, configured to fluidically couple to the first detector, in which the first modulating device is configured to accelerate flow of sample into the first detector. In other embodiments, the system comprises a second modulating device, e.g., a solenoid valve, configured to fluidically couple to the second detector, in which the second modulating device is configured to accelerate flow of sample into the second detector. The system may comprise one or more restrictors, e.g., a restrictor may be present between a flow cell of the second detector and the vacuum device of the first detector, between a flow cell of the first detector and the vacuum device of the second detector, between the first fluid flow path and the first detector, or between the second fluid flow path and the second detector or other places. In some configurations, a flow stabilizer can be present between the vacuum device and the detector. Numerous different types of detectors may be present, e.g., a detector comprising a filament may be present.

In another aspect, a system comprising a microfluidic device comprising a first internal microchannel comprising a first input port fluidically coupled to a first charging chamber and a second microchannel comprising a second input port fluidically coupled to a second charging chamber, the first charging chamber and the second charging chamber each fluidically coupled to an outlet port of the microfluidic device, and a switching valve fluidically coupled to the first charging chamber and the second charging chamber, the switching valve configured to permit flow of fluid from the first charging chamber in a first position and to permit flow from the second charging chamber in a second position, a detector fluidically coupled to the outlet port of the microfluidic device, and a vacuum device fluidically coupled to the detector to accelerate flow of fluid from the outlet port of the microfluidic device into the detector.

In some embodiments, the system may comprise a modulating device, e.g., a solenoid valve, configured to fluidically couple to the detector, in which the modulating device is configured to accelerate flow of sample into the detector. In other examples, the system may comprise an additional detector fluidically coupled to the detector. In further embodiments, the system may comprise a restrictor between a flow cell of the detector and the vacuum device, between the first fluid flow path and the detector, or between the second fluid flow path and the detector. In some instances, the inner diameter of the restrictor is fixed. In some embodiments, a flow stabilizer can be present between the vacuum device and the detector. If desired, a restrictor may be present between the detector and the flow stabilizer. In some examples, the microfluidic device further comprises an additional outlet port. Numerous different types of detectors may be present, e.g., a detector comprising a filament may be present.

In another aspect, a system comprising a microfluidic device comprising a first internal microchannel comprising a first input port fluidically coupled to a first charging chamber and a first output port fluidically coupled to the first charging chamber, and a second microchannel comprising a second input port fluidically coupled to a second charging chamber and a second output port fluidically coupled to the second charging chamber, a first detector fluidically coupled to the first outlet port of the microfluidic device, a second detector fluidically coupled to the second outlet port of the microfluidic device, and a vacuum device fluidically coupled to the first detector and to the second detector to accelerate flow of fluid from the microfluidic device into the first detector and into the second detector is described.

In certain embodiments, the system may comprise a modulating device configured to fluidically couple to the first detector or the second detector, in which the modulating device is configured to accelerate flow of sample into at least one of the first and second detectors. In other embodiments, the modulating device is configured as a solenoid valve. In further examples, the system may comprise an additional detector fluidically coupled to the first detector. In some instances, the system may include a restrictor, e.g., between a flow cell of the second detector and the vacuum device, between a flow cell of the first detector and the vacuum device, between the first fluid flow path and the first detector, or between the second fluid flow path and the second detector. The restrictor may have a fixed inner diameter or a variable inner diameter, e.g., the restrictor may take the form of a needle valve or other device whose inner diameter can be adjusted. In some examples, a flow stabilizer can be present between the vacuum device and the first detector. In other instances, a restrictor is present between the first detector and the flow stabilizer. In some examples, the microfluidic device further comprises an additional outlet port. Many different types of detectors may be present, e.g., a detector comprising a filament may be present.

In an additional aspect, a system comprising a microfluidic device comprising a first internal microchannel comprising a first input port fluidically coupled to a first charging chamber and a second microchannel comprising a second input port fluidically coupled to a second charging chamber, the first charging chamber and the second charging chamber each fluidically coupled to an outlet port of the microfluidic device, a switching valve fluidically coupled to the first charging chamber and the second charging chamber, the switching valve configured to permit flow of fluid from the first charging chamber in a first position and to permit flow from the second charging chamber in a second position, and a detector fluidically coupled to the outlet port of the microfluidic device, the detector comprising a vacuum device configured to permit operation of the detector at a pressure less than atmospheric pressure, the detector further comprising an additional fluid flow path between the inlet of the detector and the vacuum device to accelerate flow of fluid from the outlet port of the microfluidic device into the detector is disclosed.

In certain examples, the system may comprise a modulating device, e.g., a solenoid valve, configured to fluidically couple to the detector, in which the modulating device is configured to accelerate flow of sample into the detector. In other embodiments, an additional detector fluidically coupled to the detector may be present. In some instances one or more restrictors may be present, e.g., a restrictor between a flow cell of the detector and the vacuum device, between the first fluid flow path and the detector, or between the second fluid flow path and the detector. The restrictor may have a fixed inner diameter or a variable inner diameter, e.g., the restrictor may take the form of a needle valve or other device whose inner diameter can be adjusted. In some configurations, the system can include a flow stabilizer between the vacuum device of the detector and a flow cell of the detector. In other examples, the system can include a restrictor between the detector and the flow stabilizer. In further embodiments, the microfluidic device further comprises an additional outlet port. In other instances, the detector comprises at least one filament. Many different types of detectors may be present, e.g., a detector comprising a filament may be present.

In another aspect, a system comprising a microfluidic device comprising a first internal microchannel comprising a first input port fluidically coupled to a first charging chamber and a first output port fluidically coupled to the first charging chamber, and a second microchannel comprising a second input port fluidically coupled to a second charging chamber and a second output port fluidically coupled to the second charging chamber, a first detector fluidically coupled to the first outlet port of the microfluidic device, and a second detector fluidically coupled to the second outlet port of the microfluidic device, in which the second detector comprises a vacuum device that is fluidically coupled to the first detector and the second detector to accelerate flow of fluid from the microfluidic device into the first detector and into the second detector is disclosed.

In certain embodiments, the system comprises a modulating device, e.g., a solenoid valve, configured to fluidically couple to the first detector or the second detector, in which the modulating device is configured to accelerate flow of sample into at least one of the first and second detectors. In other embodiments, the system comprises an additional detector fluidically coupled to the first detector. In certain instances, the system comprises a restrictor between a flow cell of the second detector and the vacuum device of the second detector, between a flow cell of the first detector and the vacuum device of the second detector, between the first fluid flow path and the first detector, or between the second fluid flow path and the second detector. The restrictor may have a fixed inner diameter or a variable inner diameter, e.g., the restrictor may take the form of a needle valve or other device whose inner diameter can be adjusted. In some configurations, the system can include a flow stabilizer between the vacuum device of the detector and a flow cell of the detector. In other examples, the system can include a restrictor between one or both detectors and the flow stabilizer. In further embodiments, the microfluidic device further comprises an additional outlet port. In other instances, the detector comprises at least one filament. Many different types of detectors may be present, e.g., a detector comprising a filament may be present.

In an additional aspect, a microfluidic device comprising an internal microchannel comprising a first charging chamber and a second charging chamber, the first charging chamber and the second charging chamber each fluidically coupled to an inlet port and an outlet port of the microfluidic device, and a switching valve fluidically coupled to the internal microchannel of the microfluidic device and configured to permit flow of a fluid from the first charging chamber in a first position and to permit flow of fluid from the second charging chamber in a second position, and a detector in the microfluidic device and fluidically coupled to each of the first charging chamber and the second charging chamber through the switching valve and fluidically coupled to the outlet port of the microfluidic device to permit exit of fluid from the microfluidic device is provided.

In certain embodiments, the device further comprises a vacuum device fluidically coupled to outlet port of the microfluidic device, in which the vacuum device is configured to accelerate flow of fluid into the detector. In some examples, a restrictor is present between the microfluidic device and the vacuum device. In further examples, a restrictor is present in the microfluidic device. In some embodiments, the restrictor is between the switching valve and the detector, between the first charging chamber and the switching valve, between the second charging chamber and the switching valve or between the detector and the outlet port of the microfluidic device. The restrictor may have a fixed inner diameter or a variable inner diameter, e.g., the restrictor may take the form of a needle valve or other device whose inner diameter can be adjusted. In some instances, a flow stabilizer is present in the microfluidic device and between the detector and the outlet port of the microfluidic device. In other embodiments, the microfluidic device further comprises an additional outlet port. In certain examples, the system comprises a modulating device, e.g., a solenoid valve, fluidically coupled to the microfluidic device, in which the modulating device is configured to accelerate flow of sample into the detector of the microfluidic device. Many different types of detectors may be present, e.g., a detector comprising a filament may be present.

In another aspect, a microfluidic device comprising a first internal microchannel comprising a first inlet port and a first charging chamber fluidically coupled to the first inlet port, a second internal microchannel comprising a second inlet port and a second charging chamber fluidically coupled to the second inlet port, a first detector in the microfluidic device, the first detector fluidically coupled to the first charging chamber, and a second detector in the microfluidic device, the second detector fluidically coupled to the second charging chamber, in which each of the first detector and the second detector is fluidically coupled to an outlet port of the microfluidic device to permit exit of fluid from the microfluidic device is provided.

In certain embodiments, the system further comprises a vacuum device fluidically coupled to outlet port of the microfluidic device, in which the vacuum device is configured to accelerate flow of fluid into the first detector and into the second detector. In some configurations, a restrictor is present between the microfluidic device and the vacuum device. In additional examples, a restrictor may be present in the microfluidic device. In some embodiments, a restrictor is present between the first charging chamber and the first detector, between the second charging chamber and the second detector, between the first detector and the outlet port of the microfluidic device, or between the second detector and the outlet port of the microfluidic device. The restrictor may have a fixed inner diameter or a variable inner diameter, e.g., the restrictor may take the form of a needle valve or other device whose inner diameter can be adjusted. In some embodiments, a flow stabilizer is present in the microfluidic device and between the first detector and the outlet port of the microfluidic device. In some configurations, the microfluidic device further comprises an additional outlet port. In other examples, the device further comprises a modulating valve fluidically coupled to the microfluidic device, in which the modulating device is configured to accelerate flow of sample into the detector of the microfluidic device. In additional examples, the modulating valve is configured as a solenoid valve. Many different types of detectors may be present, e.g., a detector comprising a filament may be present.

In an additional aspect, a microfluidic device comprising an internal microchannel comprising a first charging chamber and a second charging chamber, the first charging chamber and the second charging chamber each fluidically coupled to an inlet port and an outlet port of the microfluidic device, and a switching valve fluidically coupled to the internal microchannel of the microfluidic device and configured to permit flow of a fluid from the first charging chamber in a first position and to permit flow of fluid from the second charging chamber in a second position, a detector in the microfluidic device and fluidically coupled to each of the first charging chamber and the second charging chamber through the switching valve and fluidically coupled to the outlet port of the microfluidic device to permit exit of fluid from the microfluidic device, and a vacuum device in the microfluidic device and fluidically coupled to the outlet port and configured to accelerate flow of fluid from the charging chambers into the detector is provided.

In certain examples, the device further comprises a restrictor between the detector and the vacuum device. In some examples, the device comprises a restrictor in the vacuum device of the microfluidic device or a restrictor in the detector of the microfluidic device. In some examples, the system comprises a restrictor in the microfluidic device in which the restrictor is between the switching valve and the detector, between the first charging chamber and the switching valve, or between the second charging chamber and the switching valve. In additional examples, the restrictor may have a fixed inner diameter or a variable inner diameter, e.g., the restrictor may take the form of a needle valve or other device whose inner diameter can be adjusted. In some configurations, the device comprises a flow stabilizer in the microfluidic device and between the detector and the vacuum device. In some examples, the microfluidic device further comprises an additional outlet port. In some embodiments, a modulating device, e.g., a solenoid valve, fluidically coupled to the microfluidic device, in which the modulating device is configured to accelerate flow of sample into the detector of the microfluidic device may be present. Many different types of detectors may be present, e.g., a detector comprising a filament may be present.

In another aspect, a microfluidic device comprising a first internal microchannel comprising a first inlet port and a first charging chamber fluidically coupled to the inlet port, a second internal microchannel comprising a second inlet port and a second charging chamber fluidically coupled to the second inlet port, a first detector in the microfluidic device, the first detector fluidically coupled to the first charging chamber, a second detector in the microfluidic device, the second detector fluidically coupled to the second charging chamber, in which each of the first detector and the second detector is fluidically coupled to an outlet port of the microfluidic device to permit exit of fluid from the microfluidic device, and a vacuum device in the microfluidic device and fluidically coupled to the outlet port and configured to accelerate flow of fluid from the first charging chamber into the first detector and to accelerate flow of fluid from the second charging chamber into the second detector is described.

In certain embodiments, the system may comprise a restrictor between the first detector and the vacuum device. In other examples, the system comprises a restrictor between the second detector and the vacuum device. In some configurations, the system comprises a restrictor in the first detector microfluidic device. In other examples, the system comprises an additional detector fluidically coupled to the first detector. In some embodiments, the system comprises an additional detector fluidically coupled to the second detector. In some instances, the system comprises a flow stabilizer in the microfluidic device and between the first detector and the vacuum device. In certain configurations, the microfluidic device further comprises an additional outlet port. In some embodiments, the system comprises a modulating device, e.g., a solenoid valve, fluidically coupled to the microfluidic device, in which the modulating device is configured to accelerate flow of sample into at least one of the first detector and the second detector of the microfluidic device. Many different types of detectors may be present, e.g., a detector comprising a filament may be present.

In another aspect, a microfluidic device comprising an internal microchannel comprising a first fluid flow path and a second fluid flow path, and a switching valve fluidically coupled to the first fluid flow path and the second fluid flow path and configured to permit flow of a fluid from the first fluid flow path in a first position and to permit flow of fluid from the fluid flow path in a second position, and a detector in the microfluidic device and fluidically coupled to each of the first fluid flow path and the second fluid flow path through the switching valve and fluidically coupled to an outlet port of the microfluidic device to permit exit of fluid from the detector of the microfluidic device is disclosed.

In an additional aspect, a microfluidic device comprising a first internal microchannel comprising a first fluid flow path fluidically coupled to a first fluid inlet of the microfluidic device, a second internal microchannel comprising a second fluid flow path fluidically coupled to a second fluid inlet of the microfluidic device, a first detector in the microfluidic device, the first detector fluidically coupled to the first fluid flow path of the first internal microchannel and fluidically coupled to an outlet port of the microfluidic device, and a second detector in the microfluidic device, the second detector fluidically coupled to the second fluid flow path of the second internal microchannel and fluidically coupled to the outlet port of the microfluidic device is provided.

In another aspect, a method of analyzing an analyte in a chromatography system comprising a separation column and a detector comprising fluidically decoupling analyte fluid flow through the separation column of the chromatography system and analyte fluid flow through the detector of the chromatography system, and accelerating analyte fluid flow through the detector of the chromatography system. In some embodiments, the method may comprise reducing the pressure in the detector to accelerate the analyte fluid flow through the detector.

In an additional aspect, a method of detecting analyte comprising introducing analyte into a first charging chamber of an interface during a first period, introducing analyte into a second charging chamber of the interface during a second period, and fluidically coupling the first charging chamber and a detector during the second period to provide a substantially constant flow of carrier gas into the detector during the first period is provided. In certain examples, the method comprises decoupling the first charging chamber and the detector during a third period and fluidically coupling the second charging chamber and the detector during the third period to provide the substantially constant flow of carrier gas into the detector during the third period. In other examples, the method comprises reducing the pressure of the detector to less than atmospheric pressure prior to the first period. In some embodiments, the method comprises maintaining the pressure of the detector to be less than atmospheric pressure during the first period, the second period and the third period.

Additional features, aspect, examples and embodiments are described in more detail below.

BRIEF DESCRIPTION OF THE FIGURES

Certain embodiments of the devices and systems are described with reference to the accompanying figures in which:

FIG. 1A is an illustration of a flow cell, in accordance with certain examples;

FIG. 1B is an illustration of a flow cell fluidically coupled to a modulating gas, in accordance with certain configurations;

FIG. 3 is a graph showing modulation pulses, in accordance with certain examples;

FIGS. 4A and 4B are systems including charging chambers fluidically coupled to a modulating gas, in accordance with certain examples;

FIGS. 8A-8D are illustrations of an interface fluidically coupled to a detector and a vacuum device, in accordance with certain examples;

FIGS. 9A-9J are illustrations of an interface fluidically coupled to two detectors and one or more vacuum devices, in accordance with certain examples;

FIGS. 10A and 10B are illustrations of an interface fluidically coupled to a detector including an integral vacuum device, in accordance with certain examples;

FIGS. 11A and 11B are illustrations of an interface fluidically coupled to two detectors at least one of which includes an integral vacuum device, in accordance with certain examples;

FIGS. 23-27 are illustrations of various systems comprising restrictors placed in different positions, in accordance with certain examples;

FIGS. 29-31B are illustrations of various systems comprising restrictors placed in different positions, in accordance with certain examples;

FIG. 35 shows an exploded view of a microfluidic device comprising first and second layers or wafer, in accordance with certain configurations;

FIG. 39 is a graph showing the peak shape using a vacuum applied to a flow cell, in accordance with certain examples;

FIG. 43 is a chromatogram obtained using the system of FIG. 42, in accordance with certain examples;

FIG. 44 is a schematic of a vacuum TCD system, in accordance with certain examples;

FIG. 45 is a schematic of a proposed interface for a vacuum-operated TCD, in accordance with certain examples;

FIG. 46 illustrates a condition where the carrier gas flow rate through the column is greater than that entering the detector through the restrictors, in accordance with certain examples;

FIG. 47 illustrates a condition where the carrier gas flow rate through the column is less than that entering the detector through the restrictors, in accordance with certain examples;

FIG. 48 illustrates a condition where the carrier gas flow rate through the column is greater than that entering the detector through the restrictors, in accordance with certain examples;

FIG. 49 is a diagram of an interface for a vacuum-operated TCD with closed loop control of the vacuum pump, in accordance with certain examples;

FIG. 73 is graph showing flow rate and displayed temperature vs elapsed time for the 10 microliter TCD since initial power-up to 300° C. and using a 160 mA cell current, in accordance with certain examples.

Figure 2:
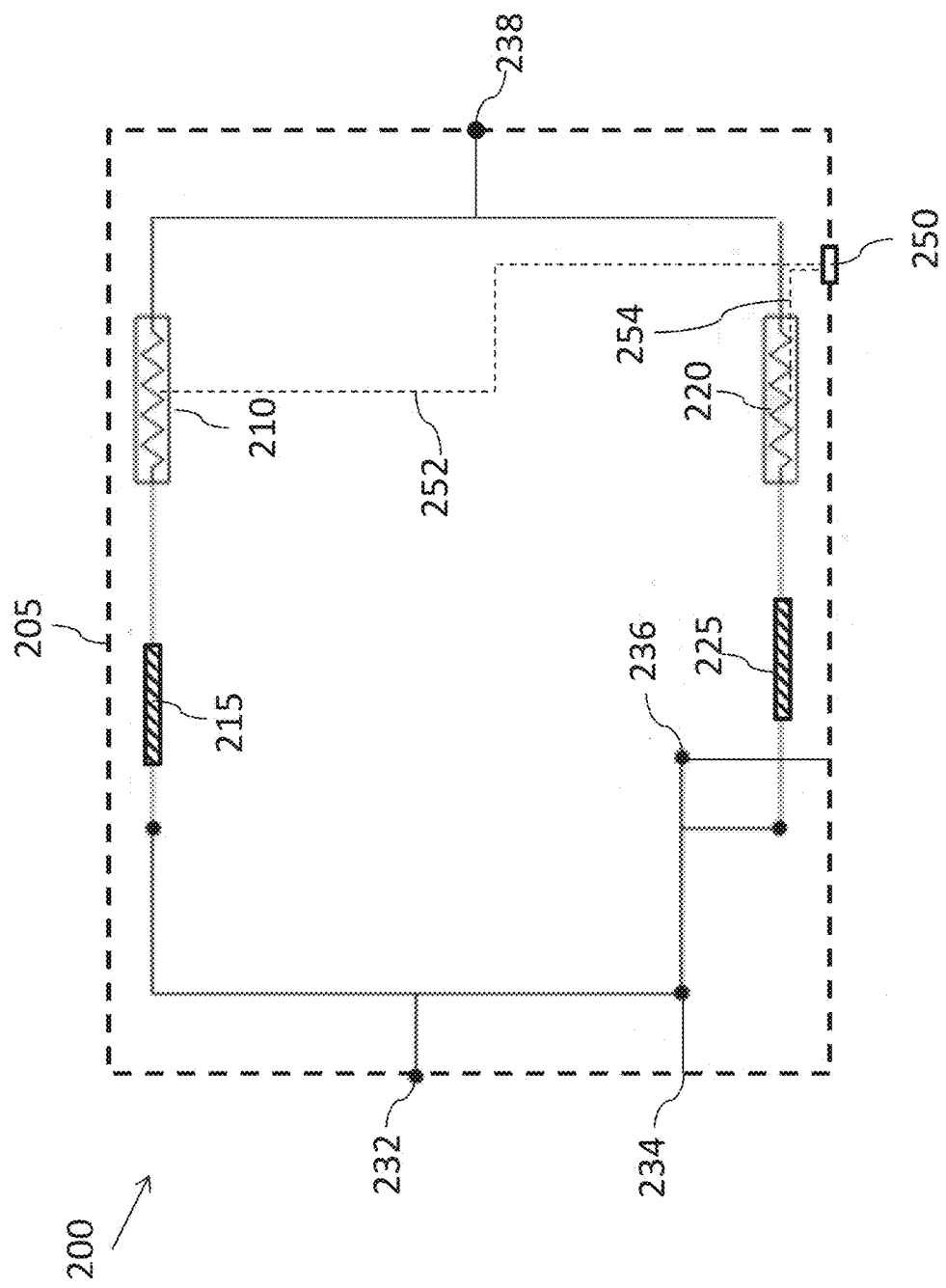
FIG. 2 is a block diagram of a manifold comprising internal restrictors and internal filament cells, in accordance with certain embodiments.

It will be recognized by the person of ordinary skill in the art, given the benefit of this disclosure, that certain dimensions or features of the components of the systems may have been enlarged, distorted or shown in an otherwise unconventional or non-proportional manner to provide a more user friendly version of the figures. In addition, the exact length, width, geometry, aperture size, etc. of the chambers, fluid paths, restrictors and other components described herein may vary.

DETAILED DESCRIPTION

Certain embodiments are described below with reference to singular and plural terms in order to provide a user friendly description of the technology disclosed herein. These terms are used for convenience purposes only and are not intended to limit the devices, methods and systems described herein. In some illustrations, the terms "fluidic coupling" or "fluidically coupled" is used. Where two or more components are fluidically coupled, fluid may pass between the components under certain, but not necessarily all, conditions. For example, a fluid path may be present to permit fluid to flow from one component to another as desired.

In certain configurations, the devices described herein may be used in or with one or more detectors commonly used with chromatographic separation systems. For example, the device may be fluidically coupled to a detector configured to receive a fluid from a chromatography column. The fluid may be a gas or a liquid or a supercritical fluid as desired. Certain illustrative embodiments are described below with reference to gas chromatography systems. Certain configurations described herein are directed to a detector that may include desirable attributes including, for example, a single filament (or multiple filaments) that can equilibrate rapidly, is stable with low flow and thermal drift and/or is compatible with both high resolution capillary columns and packed columns, e.g., the detector is operative to provide good peak shapes with about 2-second wide peaks with carrier gas flow rates down to 1 mL/min with no make-up gas and yet still work with packed columns with carrier gas flow rates up to 20 mL/min or more. The detectors may be fluidically coupled to one or more devices that are operative to accelerate sample into the detector. Numerous configurations of detectors fluidically coupled to such devices are described herein.

In certain examples, thermal conductivity detectors (TCDs) have been used on gas chromatographs for many years. It is the second most popular GC detector after the flame ionization detector (FID). The TCD comprises a heated wire filament that is contacted with the column effluent (sample stream), and the thermal flux between the filament and the detector housing is proportional to the thermal conductivity of the gas passing between them. Traditionally, the control electronics will maintain a constant current across the filament (which will approximate to a constant temperature), and the voltage applied forms the basis of the outputted detector signal. These detectors can be very sensitive to gas flow rate and temperature of the filament housing and so a second filament with pure carrier gas flowing through it is normally provided to act as a reference signal. This differential signal (sample channel minus reference channel) helps to reduce the effects of flow and thermal drift. A make-up gas can be typically added to the sample stream to provide good peak shape, but the sensitivity may be reduced by a factor of 10× or even more as the sample is diluted by the make-up gas.

In some instances of the detectors described herein, the interfaces and manifolds can be configured to decouple fluid flow through a column and fluid flow through a filament detector cell. For example, a make-up gas can be used to push sample into a filament detector cell to decouple sample flow through the cell from sample flow through a chromatography column. In other instances, a vacuum device can be used to pull sample into a filament detector cell to decouple sample flow through the cell from sample flow through a chromatography column. Depending on whether sample is pushed or pulled through the filament cell, the exact size and dimensions of the cell can vary. In certain instances, decoupling of sample flow through the detector cell and sample flow through the column can provide for better control of fluid flow through the detector cell and more reproducible and consistent results. The devices described herein also permit, if desired, omission of costly and complicated pneumatic controllers, e.g., PPC controllers, to control the flow rates of sample in a chromatography column and in a detector cell. In addition, a set of fixed restrictors in the devices described herein can permit use of the interfaces and manifolds with many different column types without the need to alter the restrictor size, e.g., without the need to change the length or internal diameter of the restrictors.

In certain embodiments and referring to FIG. 1A, a detector 100 comprises a flow cell 110 comprising a fluid inlet port 115 and a fluid outlet port 120. Sample eluted from a column 130 is provided to the flow cell 110 through the fluid inlet port 115 that is fluidically coupled to the column 130 and exits the flow cell 110 through the fluid outlet port

120. The flow cell 110 comprises a filament 112 which can be used to measure the conductivity of sample that passes through the flow cell 110. In some configurations, the exact size of the fluid inlet path 115 and the fluid outlet path 120 may vary, but in some instances, the paths 115, 120 are sized as capillaries to permit rapid pressure changes at various portions of the detector 100. Where a filament detector is used, the filament can be operative as a concentration detector such that only a small volume of sample can be introduced into the cell 110 for detection. While not shown in FIG. 1A, the interface and manifolds described herein may comprise a first cell used as an analytical cell and may comprise a second cell used as a reference cell. One or more restrictors can be placed in-line and upstream of the detector cells and/or downstream of the detector cells. In some instances, the devices described herein can be configured as a 4-filament block of manifold comprising internal restrictors and a plurality of ports for coupling the analytical cell and the reference cell in the 4-filament block to a chromatography column, make-up gas and/or a vacuum device.

In certain examples, the detector may be fluidically coupled to one or more interfaces that are operative to provide for better fluid flow control within the device or system. Referring to FIG. 1B, one configuration of a device comprises a flow cell 150 with a fluid inlet path 155 and a fluid outlet path 170. A column 180 is fluidically coupled to the flow cell 160 through the fluid inlet path 155. An interface is also fluidically coupled to the flow cell 160 through the fluid inlet path 155. The interface comprises an optional valve 185 that is fluidically coupled to a gas source 190. Prior to sample elution, the valve 185 can be closed so gas from the gas source 190 is not provided to the fluid inlet path 155. In operation of the system 150, sample elutes from the column 180 into the fluid inlet 155. Sample elution occurs at a rate generally the same as the carrier gas flow rate. The valve 185 may then be energized to fluidic ally couple the gas source 190 to the flow cell 160. The flow rate provided by the gas source may be 5-10× or more higher than the carrier gas flow rate to sweep the eluted sample rapidly into the flow cell. By selecting suitable gas flow rates from the gas source 190, sample is pushed quickly into the flow cell 160 without substantial dispersion/dilution. As the pulse of sample vapor passes through the flow cell 160, a reading from the filament 162 may be taken to detect the sample. The valve 185 may then be closed until a second sample component elutes from the column 180. After elution of the second component, the valve 185 may be opened, and gas from the gas source 190 may rapidly push the second component into the flow cell for detection. This process may be repeated numerous times to detect the components in the sample. In some instances, the valves described herein may be configured as a 2-way valve, a 3-way valve or the like to fluidically couple and decouple two or more fluid flow paths. Illustrative types of valves include, but are not limited to, solenoid valves, pressure valves, ball valves, valves with micro motors, MEMS devices or other valve devices that can actuate between two or more different positions. By controlling the flow rate of gas into the cell 160 using the gas source 190, sample flow rate through the cell 160 can generally be decoupled from the sample flow rate through the column 180. If desired, one or more vacuum devices can be fluidically coupled to the cell 160 to assist in pulling sample into the cell 160. The cell 160 can be configured as an analytical cell or as a reference cell. In some instances, the gas source 190 can be fluidically coupled to each of an analytical cell and a reference cell to assist in pushing eluted sample (or a reference sample) into one or more of the detector cells.

In certain embodiments, the filament detector cells described herein can be integrated into a common block or manifold. One attribute of such integration is that existing fluid lines can be coupled to the manifold without the need to substantially modify the fluid line components in a gas chromatography device. A block diagram of some components that may be present in a manifold or block device is shown in FIG. 2. The manifold 200 comprises an analytical cell 210, e.g., a 2-filament analytical cell, and a reference cell 220, e.g., a 2-filament reference cell, each positioned inside a housing or block 205. A sample inlet port 232 is present in the block 205 and is fluidically coupled to the analytical cell 210 through a first restrictor 215. The inlet 232 is fluidically coupled a chromatography column (not shown) to the analytical cell 210. A reference gas port 236 is also present and is fluidically coupled to the reference cell 220 through a second restrictor 225. Port 236 can be fluidically coupled to a gas source and/or pressure regulator to assist in controlling fluid flow within the channels of the block 205. A vent port 238 is present to permit sample and/or reference to exit the block 205. While a single vent port 238 is shown, if desired the cell 210 and the cell 220 may comprise a respective vent port. An optional second vent port 234 can be present to assist in controlling flow of fluid within the channels of the block 205. For example, a pressure controller, needle valve, restrictor or other device can be fluidically coupled to the port 234 to tune further the flow of fluid within the block 205. In some instances, the port 234 may be omitted or may be present in a closed position, if desired. The exact flow rates within the channels of the block 205 can vary. In some instances, the flow rate of the reference gas introduced into port 236 may vary, for example, from about 5 mL/min to about 20 mL/min. Similarly, the volume of the cells 210 and 220 can vary from about 5 microliters to about 50 microliters, e.g., about 10 microliters to about 50 microliters or about 10 microliters to about 30 microliters or about 10 microliters to about 20 microliters. The entire block 205 can be temperature controlled by placing it into an oven or other heating device. Illustrative heating temperatures depend on the exact analysis being performed and on the sample(s) being analyzed, but typically the block can be heated, for example, to about 100 deg. Celsius to about 400 deg. Celsius. While not shown in FIG. 2, an optional vacuum device can be fluidically coupled to the port 238 to assist in pulling sample through the cells 210, 220. One or more electrical connection may be present on the housing to permit electrical coupling of the cells 210, 220 to a processor, e.g., to a computer or other device. For example, an electrical coupler 250 is shown as providing an electrical coupling between the first cell 210 through an electrical connection 252, and the electrical coupler 250 provides an electrical coupling between the second cell 220 through an electrical connection 254.

In certain embodiments, the vacuum device or the make-up gas or both can assist in decoupling flow through the detector cells from flow through the separation column. For example, the flow rate of carrier gas through the detector cells can be controlled by the pressure set at the regulator on the make-up gas line (or by the vacuum device), the dimensions of the restrictors, the type of carrier gas and the temperature of the restrictors according to the Hagen-Poiseuille equation. In some instances, the flow rate of gas through the restrictors and the detector cells is typically about 2 mL/min though other flow rates can also be used.

The carrier gas flow rate through a capillary column is controlled by the inlet pressure to the column and uses a theoretical equation (again the Hagen-Poiseuille equation) to set the pressure to deliver a required flow rate. The column flow rate can be based on the dimensions of the column, the outlet pressure (which is the same pressure at the inlet to the restrictors in the detector), the type of carrier gas and the column temperature. The column inlet pressure is often adjusted dynamically to maintain a constant flow rate as the column is temperature programmed. The carrier gas flow rate through a packed column is normally controlled by a mass flow controller or a simple pressure regulator. The flow rate through the column is typically in the range 1 to 20 mL/min. though other flow rates can be used depending, for example, on the sample to be analyzed and the carrier gas used. By using a make-up gas (or vacuum device or both), the flow rates of carrier gas through the detector and the column can be independently controlled. If the column carrier gas flow rate is higher than that through the restrictors and filament cells, the excess will exit the detector via the vent. This excess can be routed to an external detector such as an FID or MS if desired. Because the TCD is a concentration-dependent detector, venting some of the column effluent does not affect the sensitivity of the detector. If the column carrier gas flow rate is less than the flow rate through the restrictors and filaments cells, the deficit can be made up by gas from the make-up supply. Some dilution of the sample stream can occur causing an apparent loss of sensitivity, but the detector will continue to operate under desired conditions. Using the illustrative configurations described herein (and similar configurations), a wide range of column gas flows may be deployed and yet the detector will continue to operate under a desired fixed flow rate requiring no (or little) adjustment by the user for different columns or operating conditions. To help ensure that the flow rate through the restrictors and filament cells remains substantially constant, the manifold can reside in a thermostatted environment—desirably mounted in the same heated block as the filament cells. Desirable attributes that results from the configurations described herein, include, but are not limited to, a more stable background signal, improved detector performance (especially when performing low-level analyses), the ability to omit expensive and precise external flow controllers, and the reduction or elimination of baseline drift in chromatography caused by changing column flow rate as the column is temperature programmed.

In certain embodiments, introduction of the gas flow from the gas source followed by subsequent detection can result in detection of sample pulses by the detector. One illustration of such pulses is shown in FIG. 3. The pulse intensities represent the concentration of the sample present at the time of sampling. Many detectors, such as TCDs, are concentration-sensitive detectors, and the height of the modulated pulses is about the same as would be observed from the un-modulated sample stream at a particular time. The difference would be that the higher flow rates using the gas source to push the sample into the flow cell can reduce peak dispersion without diluting the sample. A low column carrier gas flow rate could be used to get the detector performance seen with high make-up flow rates without the usual loss in sensitivity observed with existing detectors. By decoupling or separating a desired column flow rate with a desired detector flow rate, overall sensitivity and precision can be improved.

In certain embodiments, certain detectors may be sensitive to the flow rate with different flow rates resulting in perturbation of the detector signal. For example, TCDs are very sensitive to gas flow rates. To account for any fluctuations or perturbations of the detector signal during measurement, one or more additional modulated stages may be present. Referring to FIG. 4A, sample may enter charging chambers 410, 420 from a column (not shown) through a port 405. As one of the chambers 410, 420 is being charged with sample, the other chamber is being swept with gas from a gas source 440. For example in FIG. 4A, a valve 240 fluidically couples the chamber 420 and the gas source 440 such that sample in the chamber 420 is pulsed out of the system through an outlet 450 and to a detector (not shown). While the sample is pulsed out of the chamber 420, sample is being filled in the chamber 420. After a certain period, the valve 430 may be switched to a different position to fluidically couple the gas source 440 and the chamber 410 (see FIG. 4B). Sample is pulsed out of the chamber 410 and to a detector through the fluid outlet 450, and sample is being filled in the chamber 420. In this configuration, a substantially constant flow rate of carrier gas should be maintained through the detector and throughout the modulation cycles. This configuration also permits collection of sample vapor in one chamber while the other channel is being swept, so there is no lost sample vapor during the sweeping steps. In addition, if two pulses are generated for each cycle, the valve can be operated at half-speed to extend the valve lifetime.

Figure 5:
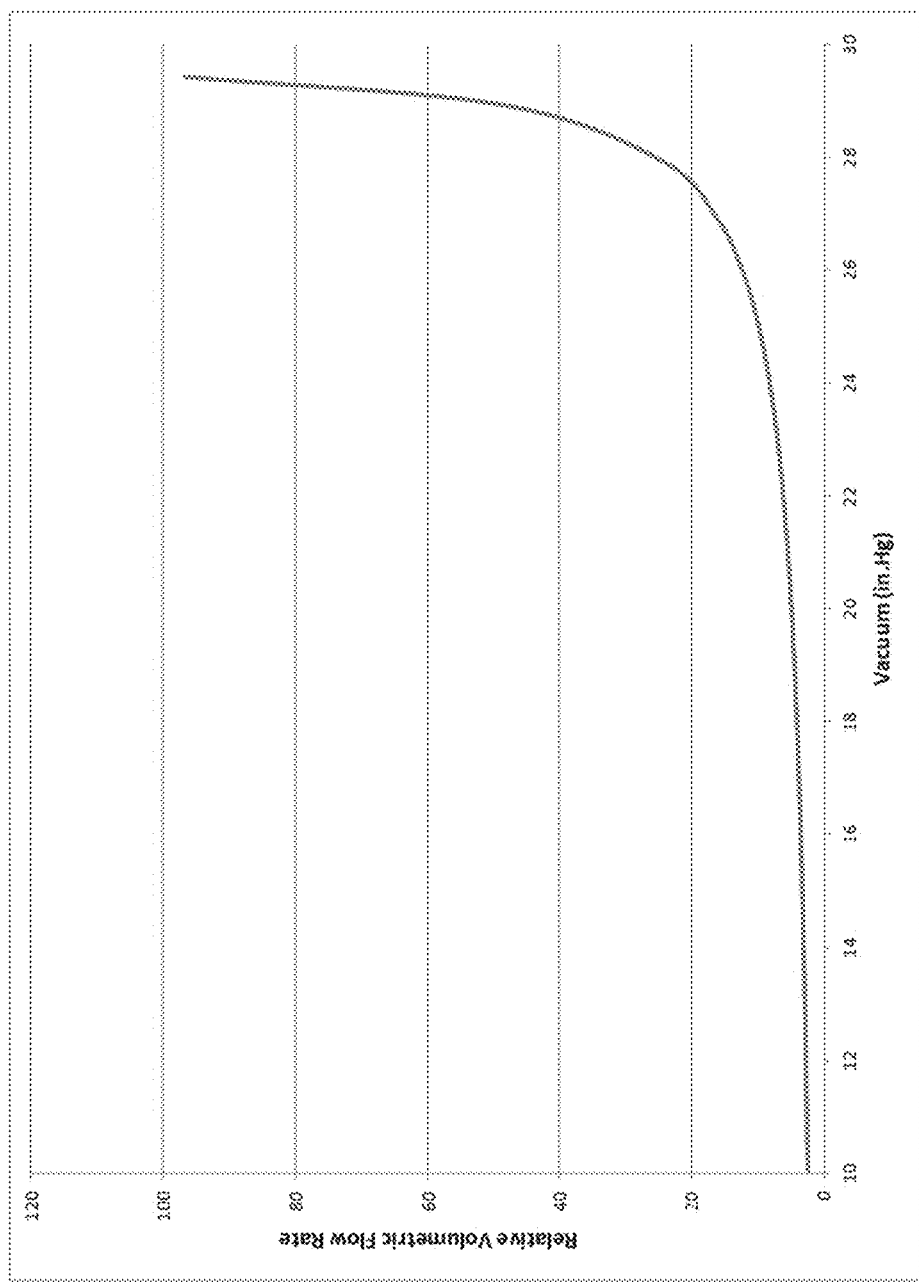
FIG. 5 is a graph showing the relationship between applied vacuum on a flow cell and the volumetric flow rate into the flow cell, in accordance with certain examples.

In certain examples, rather than pushing the sample into a detector using pulse sweeping, the pressure within the detector may be lowered in a pulsed or continuous manner to draw (or push) eluted sample into the detector. In both instances, the end result is better control of sample flow into the detector. For example and referring to FIG. 5, the pressure inside the detector may be reduced by pulling a vacuum on the detector, e.g., using a vacuum pump or other suitable device to lower the pressure in the flow cell of the detector. As the applied vacuum pressure increases, the volumetric flow into the detector rapidly increases. The vacuum pressure shown in FIG. 5 is expressed as inches of mercury below ambient pressure (which is 29.92 inches of mercury), and a larger number is reflective of a lower pressure. As noted herein, sample can instead be pushed into the filament cells using a make-up gas. The systems and devices described herein may use a gas to pulse sample into a detector cell, may draw a vacuum on the detector cell to accelerate sample into the detector cell or may be configured to both provide a positive pressure gas to pulse sample into the detector and to draw a vacuum on the detector cell to accelerate sample into the detector cell.

Figure 6:
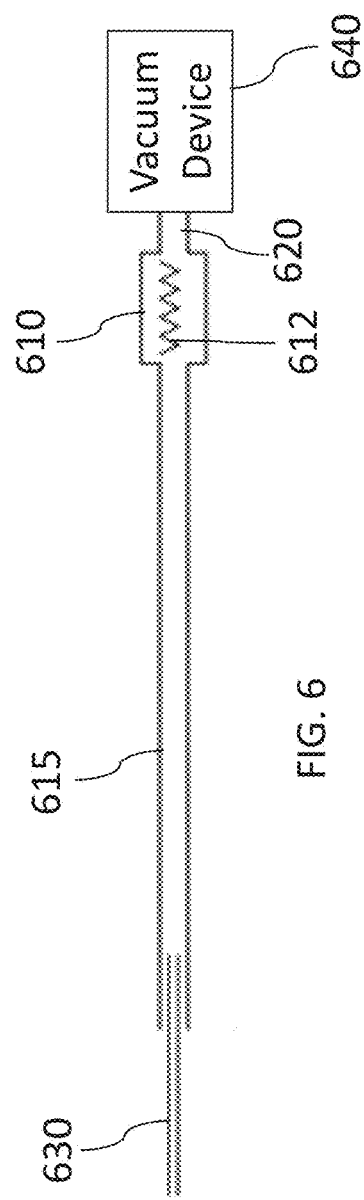
FIG. 6 is an illustration of a flow cell fluidically coupled to a vacuum device, in accordance with certain examples.

In some instances, a device configured to provide a vacuum may be fluidically coupled to an outlet of a flow cell to reduce the pressure within the detector flow cell. One illustration of a system including a vacuum device is shown in FIG. 6. A flow cell 610 comprises a filament 612. The flow cell 610 is fluidically coupled to a column 630 through a fluid inlet 615 and to a vacuum device 640 through a fluid outlet 620. As sample elutes from the column 630 into the fluid inlet 615, the vacuum device 640 may be switched on to decrease the pressure in the flow cell to accelerate sample into the flow cell 610. By applying a vacuum to the outlet 620 of the flow cell 610, an effective volumetric flow rate improvement of 10×, 20×, 30×, 40×, 50× or more can be achieved depending on the exact vacuum applied.

Figure 7:
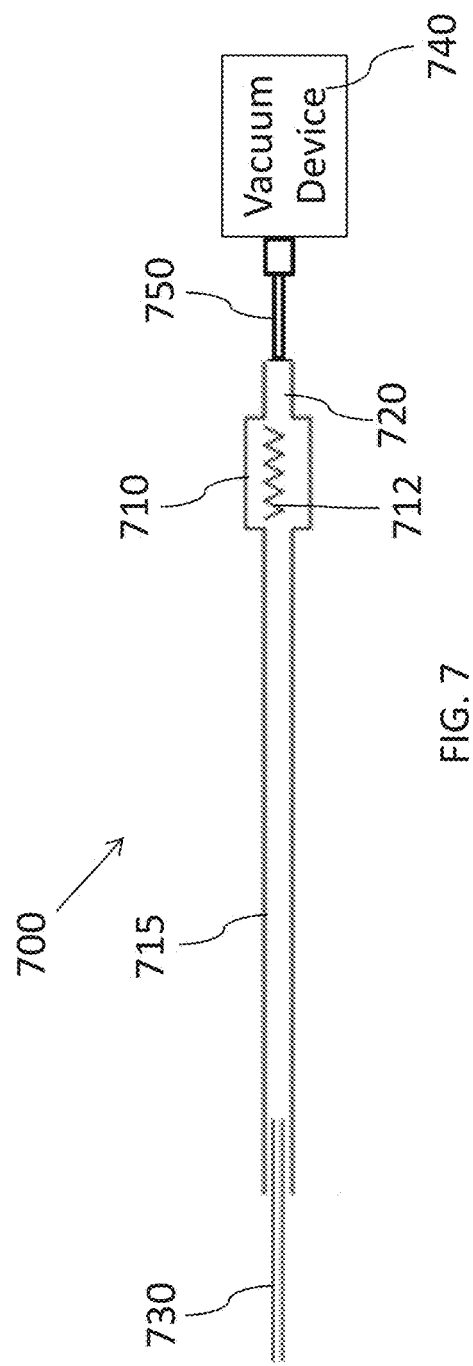
FIG. 7 is an illustration of a flow cell fluidically coupled to a vacuum device through a restrictor, in accordance with certain examples.

In some instances, it may be desirable to restrict the fluid path between the vacuum device and the flow cell to provide for better control of the pressure within the flow cell. One configuration of such a system is shown in FIG. 7. The system 700 comprises a flow cell 710 fluidically coupled to a column 730 through a fluid inlet path 715. The flow cell 710 is also fluidically coupled to a vacuum device 740 through a restrictor 750 fluidically coupled to an outlet path 720 of the flow cell 710. The flow cell 710 comprises a filament 712 in the embodiment shown in FIG. 7. The restrictor 750 may take numerous forms or may be numerous different devices as described in more detail herein. In some instances, the restrictor 750 may be fixed such that the size of its internal fluid path is not adjustable, whereas in other examples, the restrictor 750 may be a variable restrictor to permit adjustment of the fluid flow rate through the restrictor 750. The flow through the detector will depend, at least in part, on the restrictor size, the carrier gas flow rate, the flow rate of any modulating gas and/or the degree to which a vacuum is provided to the detector. If desired, different carrier gases and/or different modulating gases may use different types or sizes of restrictors. Without wishing to be bound by any particular scientific theory, the restrictor size and/or length can be selected to stabilize fluid flow through the system. Methods of determining suitable restrictor sizes may be found, for example, in commonly owned U.S. Pat. No. 8,303,694, the entire disclosure of which is hereby incorporated herein for all purposes. In instances where the vacuum devices of FIGS. 6 and 7 are omitted and where a make-up gas is instead used to push sample into a cell, a restrictor can be present between the cell and a vent port to assist in better control of fluid flow in the system.

In certain configurations, the systems described herein may comprise an interface, a detector and an optional vacuum device fluidically coupled to the detector to accelerate flow of fluid from the interface into the detector. Referring to FIG. 8A, a system 800 comprises an interface 810 which comprises two or more flow paths. For example, the interface 800 may comprise a first fluid flow path 820 between a fluid input port 822 and a fluid outlet port 824, and a second fluid flow path 830 between a fluid input port 832 and a fluid outlet port 834. In operation of the system 800, sample can elute from a column (not shown) into one or both of the fluid flow paths 820, 830. For example, a switching valve 835 may be actuated between positions to permit the sample within the first fluid flow path 820 to flow into a detector 840. The valve is configured so that the fluid flow path 830 is loaded with sample and is fluidically decoupled from the detector 840 in a first position. An optional vacuum source 850 may be switched on during actuation of the valve 835 to accelerate flow of sample from the first fluid path 820 into the detector. At a second period, the valve 835 may be switched to a second position to fluidically couple the second fluid flow path 830 and the detector 840 and to fluidically decouple the first fluid flow path 830 and the detector 840. The vacuum device 850 may again be switched on (or may remain on during operation of the system 800) to accelerate sample into the detector 840. The switching valve 835 may take numerous forms including a solenoid valve, ball valve, a microfluidic device or other devices. Referring to FIG. 8B, one or more restrictors, e.g., restrictor 855, may be present between components of the system. As shown in FIG. 8B, the restrictor is present between the detector 840 and the vacuum device 850. If desired, however, a restrictor may instead be present in one or both of the fluid flow paths 820, 830, between the fluid outlet ports and the switching valve 835, between the switching valve 835 and the detector 840 or between other components of the system. In some embodiments of the system 800, two or more restrictors may be present. For example, a first restrictor may be present between the detector 840 and the vacuum device 850 and a second restrictor may be present between the switching valve 835 and the detector 840. In some instances, the components 810-840 of FIGS. 8A and 8B can be integrated into a common manifold or block as noted in connection with FIG. 2 herein.

In certain arrangement of the components shown in FIGS. 8A and 8B, one or more valves (or pressure regulators) and/or gases may be present to control sample flow into the detector 840. Two of many possible configurations are shown in FIGS. 8C and 8D. Referring to FIG. 8C, a valve 860 fluidically coupled to a gas source 870 and to the detector 840 is shown. In some embodiments, the valve 860 may fluidically couple the gas source 870 to the detector 840 when the valve 860 is in a first position. In other instances, the valve 860 may fluidically decouple the gas source 870 to the detector 840 when the valve 860 is in a second position. When the gas source 870 and the detector 840 are fluidically coupled, the gas source may introduce a gas to drive sample in the fluid flow path between the switching valve 835 and the detector 840 into the detector 840. By using both a gas source 870 and an optional vacuum device 850, enhanced control of sample flow in the system can be achieved. If desired and referring to FIG. 8D, one or more restrictors, such as restrictor 875 may be present between the components of the system. If desired, however, a restrictor may instead be present in the system of FIG. 8D in one or both of the fluid flow paths 820, 830, between the fluid outlet ports and the switching valve 835, between the switching valve 835 and the detector 840 or between other components of the system. In some embodiments of the system of FIG. 8D, two or more restrictors may be present. In some instances, the components 810-840 of FIGS. 8C and 8D can be integrated into a common manifold or block as noted in connection with FIG. 2 herein.

Figure 9I:
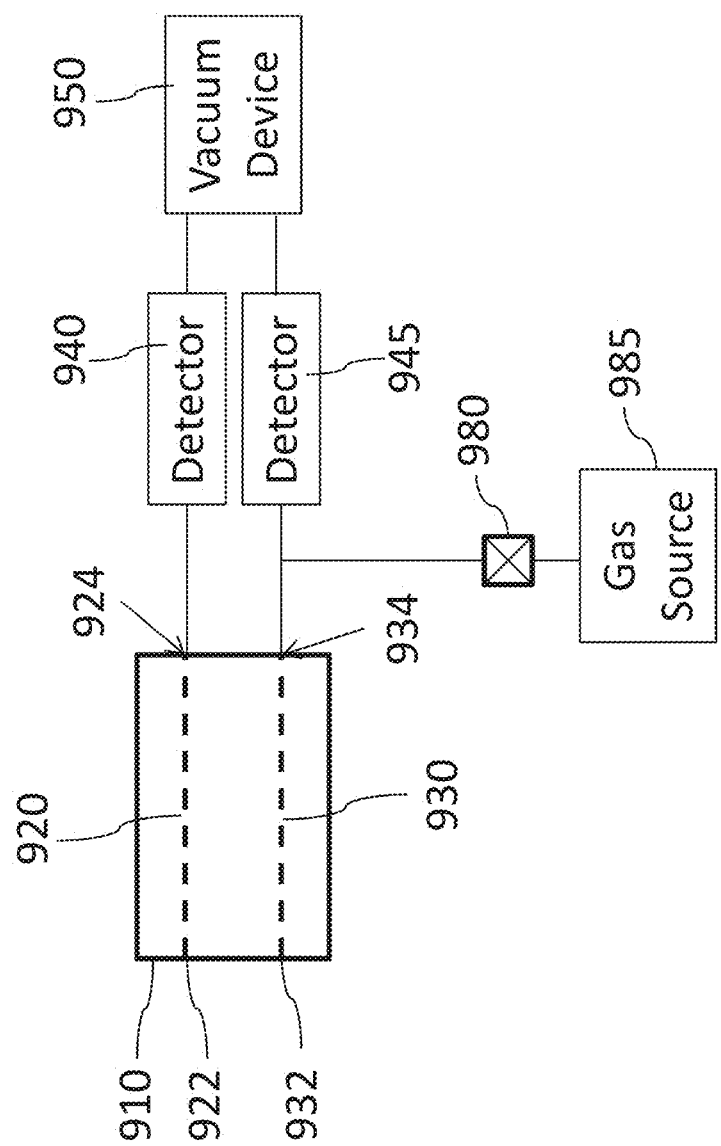

In certain configurations, the interfaces described herein may be configured to fluidically couple two or more detectors to one or more columns. For example and referring to FIG. 9A, a system 900 comprises an interface 910 comprising a first fluid flow path 920 between a first fluid input port 922 and a first fluid outlet port 924 and a second fluid flow path 930 between a second fluid input port 932 and a second fluid outlet port 934. The system also comprises a first detector 940 fluidically coupled to the first fluid flow path 930, and a second detector 945 fluidically coupled to the second fluid flow path 930. The system further comprises an optional vacuum device 950 fluidically coupled to the first detector 940 and the second detector 945 to accelerate flow of fluid from the interface 910 into the first detector 940 and into the second detector 945. In operation of the system 900, sample can elute from a column (not shown) into one or both of the fluid flow paths 820, 830. In some embodiments, each of the fluid flow paths 820, 830 may be fluidically coupled to a respective column for parallel analysis using the system 900, whereas in other instances, one of the detector 940 can be operative as an analytical cell and the other detector 945 can be operative as a reference cell. Sample within the fluid flow path 920 may be accelerated into the detector 940 by pulling a vacuum in the detector 940 using an optional vacuum device 950 or using a make-up gas (as described herein). Similarly, sample within the fluid flow path 930 may be accelerated into the detector 945 by pulling a vacuum in the detector 945 using the optional vacuum device 950. While the system 900 is shown as comprising a single vacuum device fluidically coupled to each of the detectors, two or more vacuum device may be present. For example and referring to FIG. 9B, a first vacuum device 955 is fluidically coupled to the first detector 940, and a second vacuum device 956 is fluidically coupled to the first detector 945. In some instances, the components 910-945 of FIGS. 9A and 9B can be integrated into a common manifold or block as noted in connection with FIG. 2 herein.

In certain embodiments, one or more restrictors may be present in the system 900. Referring to FIG. 9C, a restrictor 935 is present between the first fluid outlet 924 and the first detector 940. As discussed herein, the presence of one or more restrictors may better balance pressures and flow rates in the system. If desired, the restrictor may be present between other components. For example, a restrictor 936 is shown in FIG. 9D as being between the first detector 940 and the optional vacuum device 950. In FIG. 9E, restrictors 936, 937 are present between the first and second detectors 940, 940, respectively, and the optional vacuum device 950. In FIG. 9F, restrictors 936, 937 are present between the first and second detectors 940, 945, respectively, and the vacuum device 950, and restrictors 935, 938 are present between the first and second fluid outlets 924, 934, and the first and second detectors 940, 950, respectively. In FIG. 9G, an additional restrictor 927 is present in the system shown in FIG. 9F, and the additional restrictor 927 is present in the first fluid flow path 920. In FIG. 9H, a restrictor 937 is present in the second fluid flow path 930.

Figure 9J:
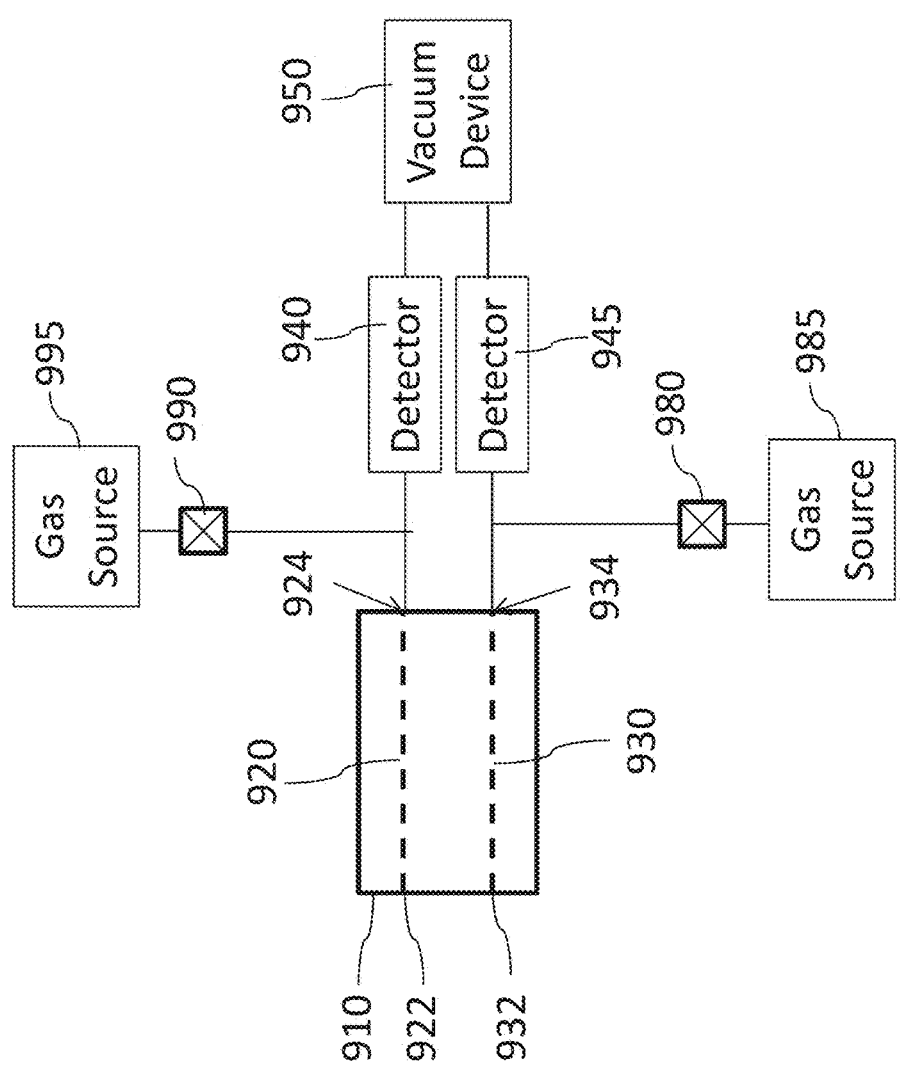

In certain configurations, the system 900 may comprise a valve (or pressure regulator) and/or gas source as described herein. For example and referring to FIG. 9I, a gas source 985 can be fluidically coupled and decoupled to the second detector 945 through a valve 980. If desired, an additional valve 990 and gas source 995 may be fluidically coupled and decoupled to the first detector 940 (see FIG. 9J). The systems shown in FIGS. 9I and 9J may include, if desired, restrictors, two vacuum sources or other components described in reference to FIGS. 9A-9H. The presence of both a gas source and/or a vacuum device in systems with multiple detectors enhances the ability to control fluid flow into the detectors. In some instances, all the components numbered from 910-945 of FIGS. 9C-9J (exclusive of the restrictors 936, 937) can be integrated into a common manifold or block as noted in connection with FIG. 2 herein. In other instances, all the components numbered 910-945 of FIGS. 9C-9J (inclusive of the restrictors 936, 937) can be integrated into a common manifold or block as noted in connection with FIG. 2 herein.

In certain configurations described herein, the various components may be integrated into a common interface or manifold. For example, the filaments and ports can be present in a common block or manifold that can be fluidically coupled to a column, a gas (if desired) and/or one or more optional vacuum devices. In certain instances, the vacuum device may be an integral component of the detector. Referring to FIG. 10A, a device 1000 comprises an manifold 1005 that includes an interface 1010 which comprises two or more flow paths. For example, the interface 1000 may comprise a first fluid flow path 1020 between a fluid input port 1022 and a fluid outlet port 1024, and a second fluid flow path 1030 between a fluid input port 1032 and a fluid outlet port 1034. In operation of the device 1000, sample can elute from a column (not shown) into one or both of the fluid flow paths 1020, 1030. In some instances, a valve 1035 may be actuated between positions to permit the sample within the first fluid flow path 1020 to flow into a detector 1040. The valve 1035 is configured so that the fluid flow path 1030 is loaded with sample and is fluidically decoupled from the detector 1040 in a first position. An optional vacuum source can be integral to the detector 1040 and may be switched on during actuation of the valve 1035 to accelerate flow of sample from the first fluid path 1020 into the detector 1040. In other instances, the vacuum source of the detector may remain on during operation of the system 1000 to keep the flow cell of the detector at a pressure less than atmospheric pressure. At a second period, the valve 1035 may be switched to a second position to fluidically couple the second fluid flow path 1030 and the detector 1040 and to fluidically decouple the first fluid flow path 830 and the detector 1040. The vacuum device (when present) of the detector 1040 may again be switched on (or may remain on during operation of the system 1000) to accelerate sample into the detector 1040. In some instances, the vacuum device of the detector may be fluidically coupled to the flow cell of the detector 1040 through one or more valves to permit fluidic coupling and decoupling between the flow cell of the detector 1040 and the vacuum device. One or more restrictors may be present between components of the system 1000. In other configurations, a gas source 1070 and a valve 1060 (see FIG. 10B) may be present. The valve 1060 may fluidically couple the gas source 1070 to the detector 1040 when the valve 1060 is in a first position. In other instances, the valve 1060 may fluidically decouple the gas source 1070 to the detector 1040 when the valve 1060 is in a second position. When the gas source 1070 and the detector 1040 are fluidically coupled, the gas source 1070 may introduce a gas to push sample in the fluid flow path between the switching valve 1035 and the detector 1040 into the detector 1040. By using a gas source 1070, enhanced control of sample flow into the cell of the detector 1040 can be achieved.

In certain examples, one of the detectors of the systems described herein may comprise an integral vacuum device that can be used to draw sample into the detector. Where two or more detectors are present, the vacuum device of one of the detectors may be fluidically coupled to the other detector to draw sample into both detectors. Referring to FIG. 11A, a device 1100 comprises an block or manifold 1105 comprising an interface 1110 comprising a first fluid flow path 1020 between a first fluid input port 1122 and a first fluid outlet port 1124 and a second fluid flow path 930 between a second fluid input port 1132 and a second fluid outlet port 1134. The device 1100 also comprises a first detector 1140 with an integral vacuum device. The detector 1140 is fluidically coupled to the first fluid flow path 1130, and a second detector 1145 fluidically coupled to the second fluid flow path 1130. The vacuum device of the first detector 1130 is fluidically coupled to the second detector 1145. In operation of the system 1100, sample can elute from a column (not shown) into one or both of the fluid flow paths 1120, 1130. In some embodiments, each of the fluid flow paths 1120, 1130 may be fluidically coupled to a respective column for parallel analysis using the system 1100. Sample within the fluid flow path 1120 may be accelerated into the detector 1140 by pulling a vacuum in the detector 1140 using the vacuum device of the detector 1140. Similarly, sample within the fluid flow path 1130 may be accelerated into the detector 1145 by pulling a vacuum in the detector 1145 using the vacuum device of the detector 1140. While the system 1100 is shown as comprising a single vacuum device within a detector, two or more vacuum device may be present. For example, a second detector 1150 (see FIG. 11B) comprising an integral vacuum device may be present in the system. As described in reference to the other figures herein, the systems of FIGS. 11A and 11B may comprise a gas source and valve to assist in controlling sample flow into the cells of the detectors. The systems of FIGS. 11A and 11B may also comprise one or more restrictors present between two components. Additional components described in reference to FIGS. 8A-10B may also be included in the systems of FIGS. 11A and 11B.

Figure 12A:
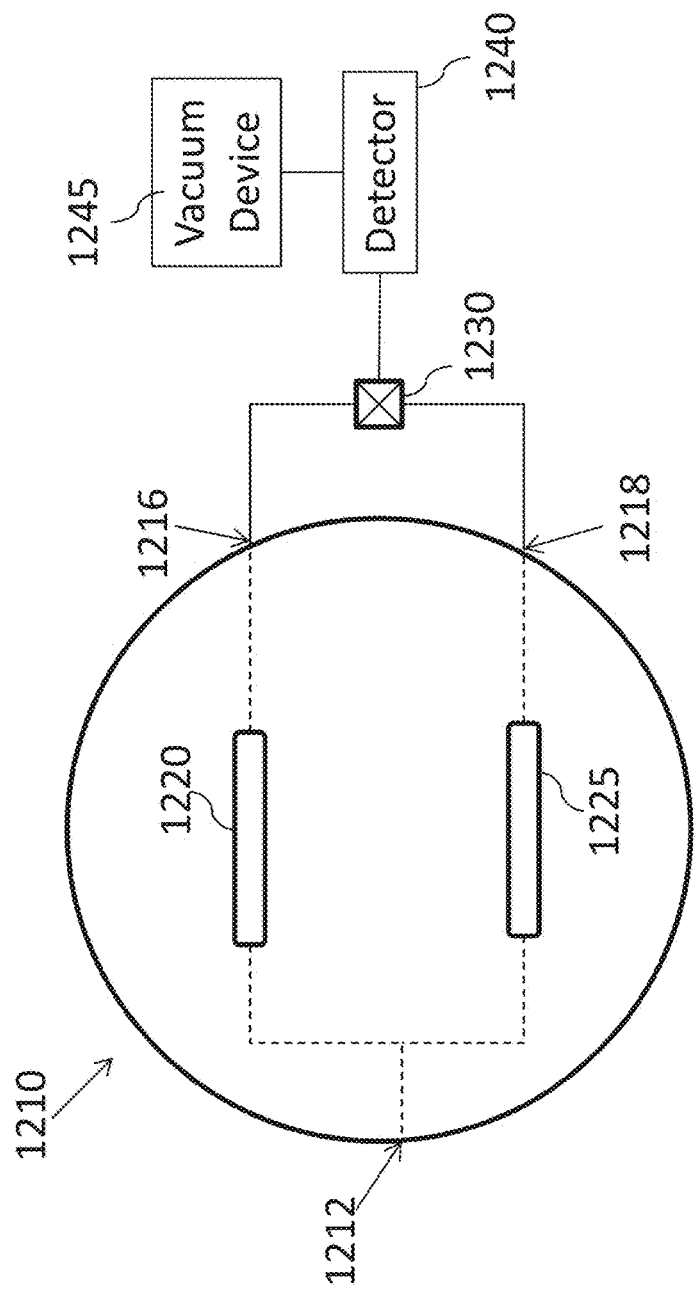
FIGS. 12A and 12B are illustrations of a system comprising a microfluidic device interface fluidically coupled to a detector and vacuum device, in accordance with certain examples.
Figure 12B:
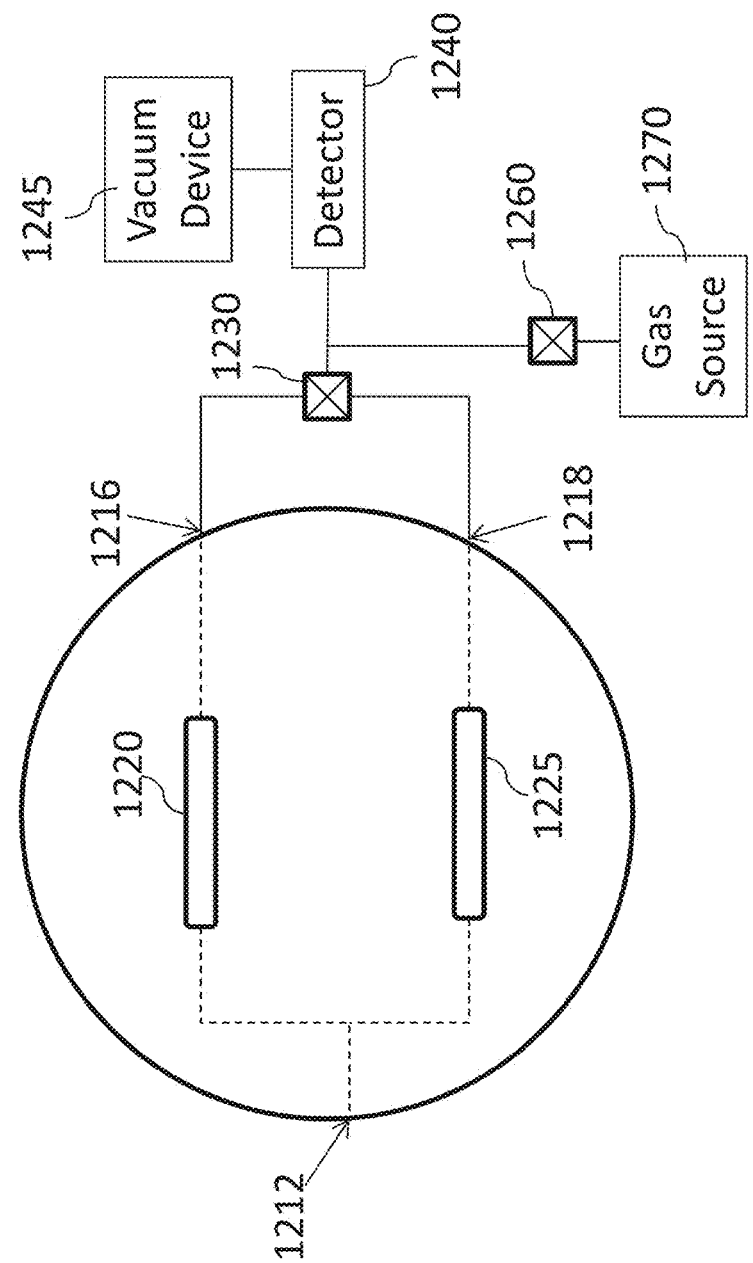

In certain embodiments, the interfaces described herein may be configured as a microfluidic device comprising one or more internal charging chambers and/or one or more internal filament flow cell detectors. For example and referring to FIG. 12A, an enlarged view of a microfluidic device 1210 is shown as comprising an internal microchannel comprising a first charging chamber 1220 and a second charging chamber 1225. The first charging chamber 1220 and the second charging chamber 1225 are each fluidically coupled to an inlet port 1212. The charging chambers 1220, 1225 may be fluidically coupled to a common fluid outlet port or may be coupled to a respective outlet port 1216, 1218 as shown in FIG. 12A. A switching valve 1230 may be fluidically coupled to the first and second charging chambers 1220, 1225 through the outlet ports 1216, 1218. In some configurations, the switching valve 1230 is configured to permit flow of fluid from the first charging chamber 1220 in a first position and to permit flow from the second charging chamber 1225 in a second position. A detector 1240 may be fluidically coupled to the outlet ports 1216, 1218 of the microfluidic device 1210 through the switching valve 1230. As noted herein, the detector 1240 may be present in a common manifold or block, e.g., may be present in a block similar to FIG. 2. A vacuum device 1245 may be fluidically coupled to the detector 1240 to accelerate flow of fluid from the microfluidic device 1210 and into the detector 1240. If desired, one or more restrictors may be present between the components shown in FIG. 12A. In some instances, one or more gas sources may be fluidically coupled to the detector 1240 to assist in pushing sample into the detector 1240. For example and referring to FIG. 12B, a gas source 1270 may be fluidically coupled to the detector 1240 through a valve 1260. The valve 1260 may fluidically couple the gas source 1270 to the detector 1240 when the valve 1260 is in a first position. In other instances, the valve 1260 may decouple the gas source 1270 to the detector 1240 when the valve 1260 is in a second position. When the gas source 1270 and the detector 1240 are fluidically coupled, the gas source may introduce a gas to drive sample in the fluid flow path between the switching valve 1230 and in the detector 1240 into the cell of the detector 1240. By using a gas source 1270, enhanced control of sample flow in the system can be achieved. If desired, one or more restrictors may be present between the components of the system of FIG. 12B. In some instances, the width of the internal microchannel in the device 1210 may be variable to provide restriction to fluid flow within the microchannel.

Figure 13A:
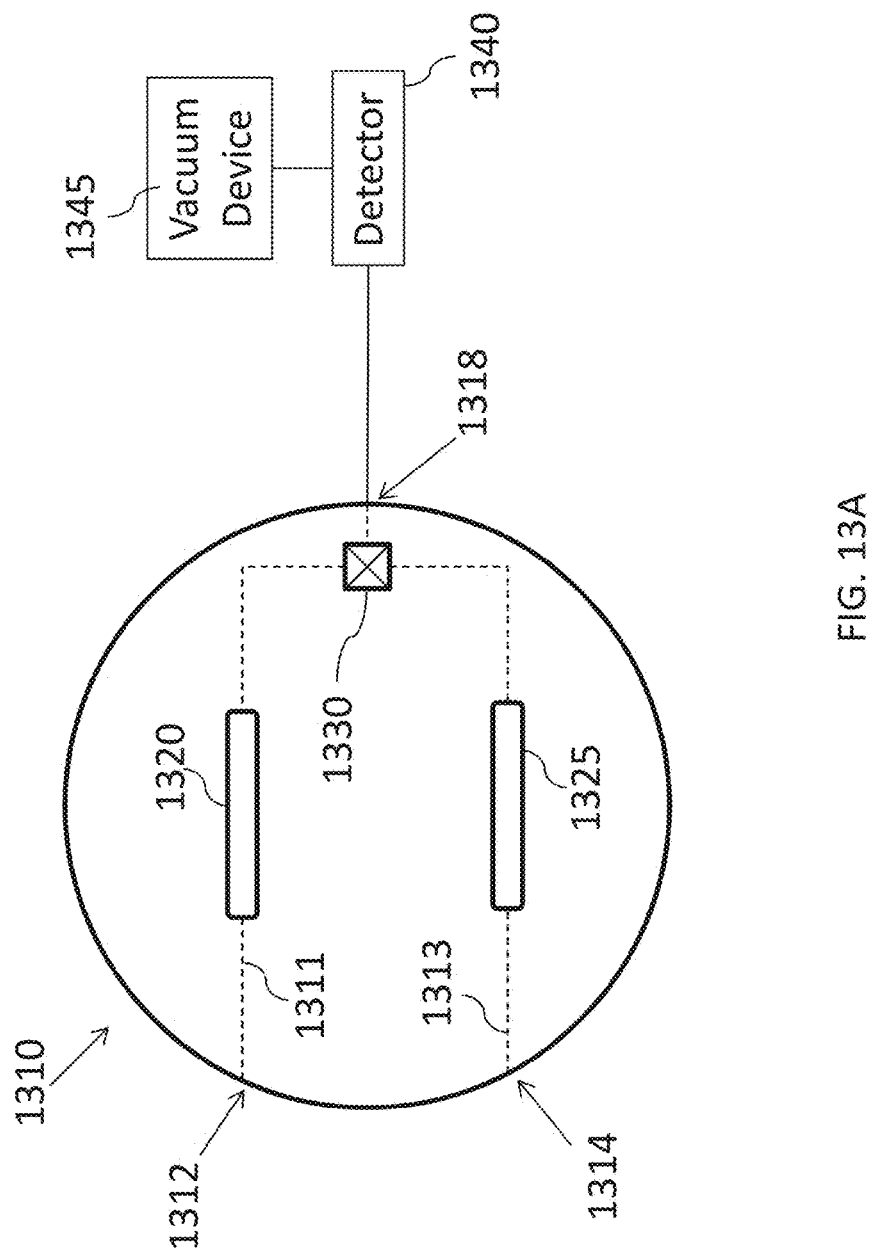
FIGS. 13A and 13B are illustrations of a system comprising another microfluidic device interface fluidically coupled to a detector and vacuum device, in accordance with certain examples.
Figure 13B:
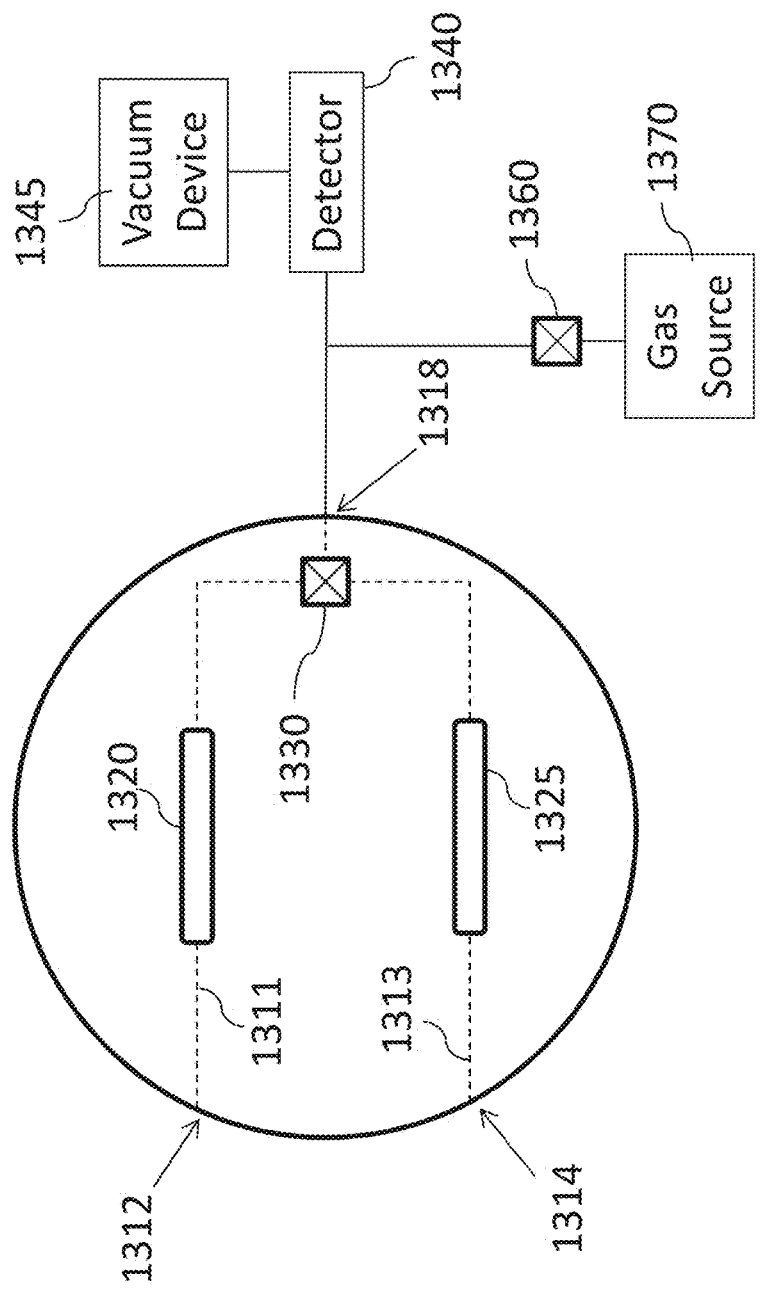

In certain embodiments, a system (see FIG. 13A) comprises a microfluidic device 1310 comprising a first internal microchannel 1311 comprising a first input port 1312 fluidically coupled to a first charging chamber 1320 and a second internal microchannel 1313 comprising a second input port 1314 fluidically coupled to a second charging chamber 1325. The first charging chamber 1320 and the second charging chamber 1325 are each fluidically coupled to an outlet port 1318 of the microfluidic device 1310 through an on-board switching valve 1330. The switching valve is configured to permit flow of fluid from the first charging chamber 1320 in a first position and to permit flow from the second charging chamber 1325 in a second position. A detector 1340 is fluidically coupled to the switching valve 1330. In some instanced, the detector 1340 can be integrated into the device 1310, whereas in other instances, the detector 1240 can be present in a common block or manifold, e.g., as described in reference to FIG. 2. An optional vacuum device 1345 is fluidically coupled to the detector 1340. The vacuum device 1345 is operative to accelerate flow of fluid from the outlet port 1318 of the microfluidic device 1310 and into the detector 1340. If desired, one or more restrictors may be present between the components shown in FIG. 13A. In some instances, one or more gas sources may be fluidically coupled to the detector 1340. For example and referring to FIG. 13B, a gas source 1370 may be fluidically coupled to the detector 1340 through a valve 1360. The valve 1360 may fluidically couple the gas source 1370 to the detector 1340 when the valve 1360 is in a first position. In other instances, the valve 1360 may fluidically decouple the gas source 1370 to the detector 1340 when the valve 1360 is in a second position. When the gas source 1370 and the detector 1340 are fluidically coupled, the gas source may introduce a gas to drive sample in the fluid flow path between the switching valve 1330 and the detector 1340 into the cell of the detector 1340. By using a gas source 1370, enhanced control of sample flow into the detector can be achieved. If desired, one or more restrictors may be present between the components of the system of FIG. 13B. In some instances, the width of the internal microchannel in the device 1310 may be variable to provide restriction to fluid flow within the microchannel.

Figure 14A:
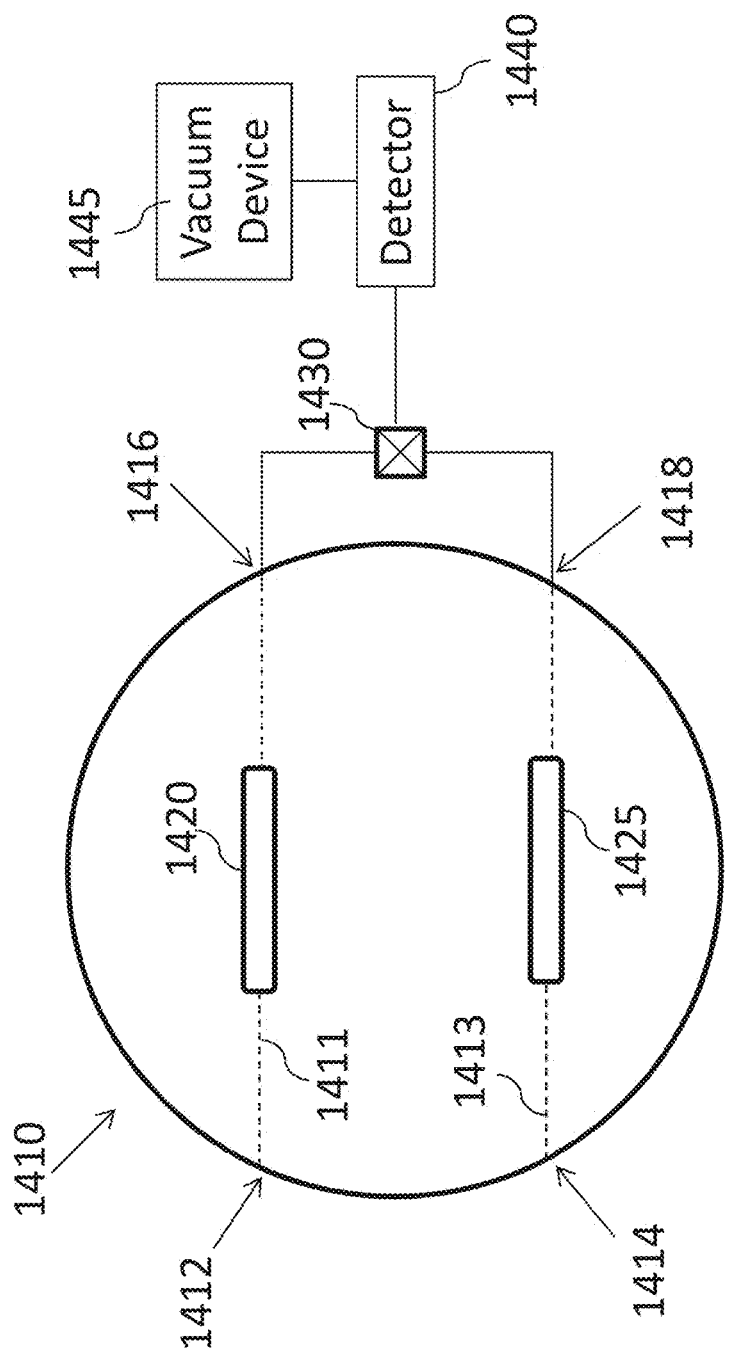
FIGS. 14A and 14B are illustrations of a system comprising an additional microfluidic device interface fluidically coupled to a detector and vacuum device, in accordance with certain examples.
Figure 14B:
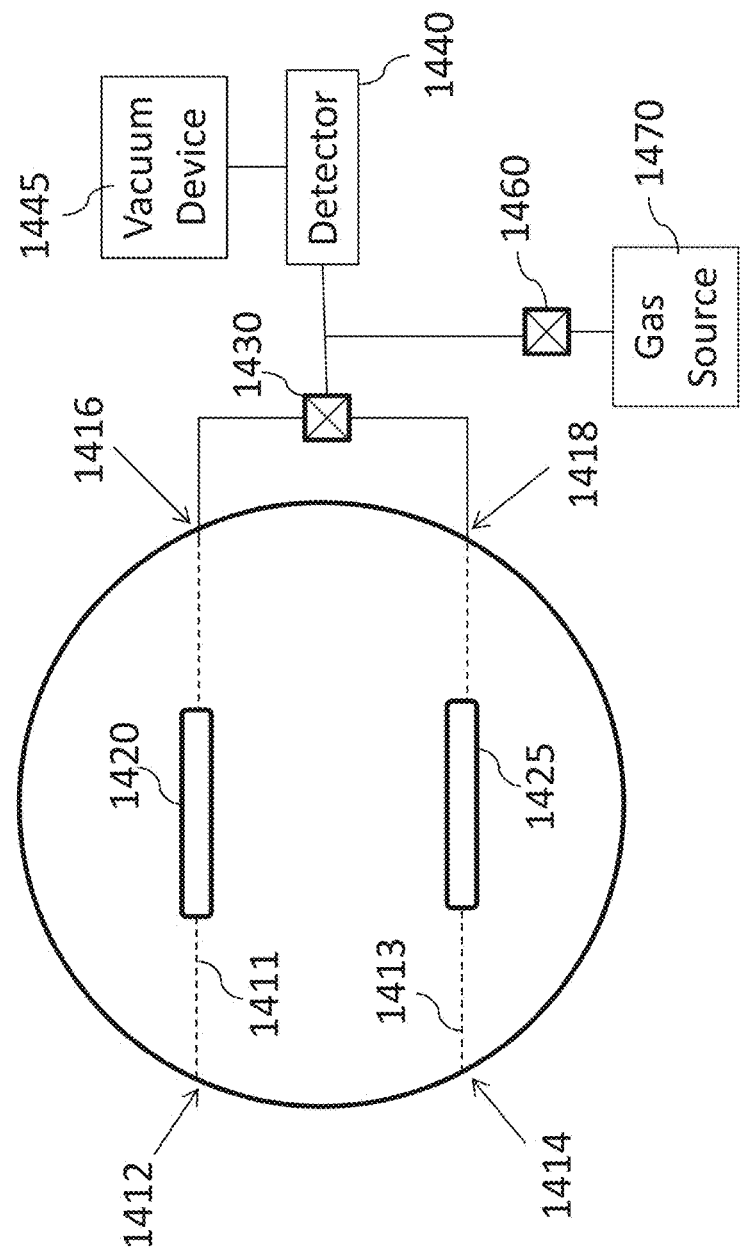

In certain configurations where a microfluidic device is implemented, the charging chambers of the microfluidic devices may be fluidically coupled to their own respective inlet and outlet ports. Referring to FIG. 14A, a microfluidic device 1410 comprising a first internal microchannel 1411 comprising a first input port 1412 fluidically coupled to a first charging chamber 1420 and first output port 1416 fluidically coupled to the charging chamber 1420. The device 1410 also includes a second internal microchannel 1413 comprising a second input port 1414 fluidically coupled to a second charging chamber 1425 and a second output port 1418 fluidically coupled to the charging chamber 1425. A switching valve 1430 is fluidically coupled to each of the output ports 1416 and 1418. The switching valve 1430 is configured to permit flow of fluid from the first charging chamber 1420 in a first position and to permit flow from the second charging chamber 1425 in a second position. A detector 1440 is fluidically coupled to the switching valve 1430. As noted herein, the detector 1440 can be integrated into the device 1410 or may be present in a common manifold or block as described in connection with FIG. 2, for example. An optional vacuum device 1445 is fluidically coupled to the detector 1440. The vacuum device 1445 is operative to accelerate flow of fluid from the outlet ports 1416, 1418 of the microfluidic device 1410 and into the detector 1440. If desired, one or more restrictors may be present between the components shown in FIG. 14A. In some instances, one or more gas sources may be fluidically coupled to the detector 1440. For example and referring to FIG. 14B, a gas source 1470 may be fluidically coupled to the detector 1440 through a valve 1460. The valve 1460 may fluidically couple the gas source 1470 to the detector 1440 when the valve 1460 is in a first position. In other instances, the valve 1460 may fluidically decouple the gas source 1470 to the detector 1440 when the valve 1460 is in a second position. When the gas source 1470 and the detector 1440 are fluidically coupled, the gas source may introduce a gas to drive sample in the fluid flow path between the switching valve 1430 and the detector 1440 into the cell of the detector 1440. By using a gas source 1470, enhanced control of sample flow into the detector can be achieved. If desired, one or more restrictors may be present between the components of the system of FIG. 14B. In some instances, the width of an internal microchannel in the device 1410 may be variable to provide restriction to fluid flow within the microchannel.

Figure 15A:
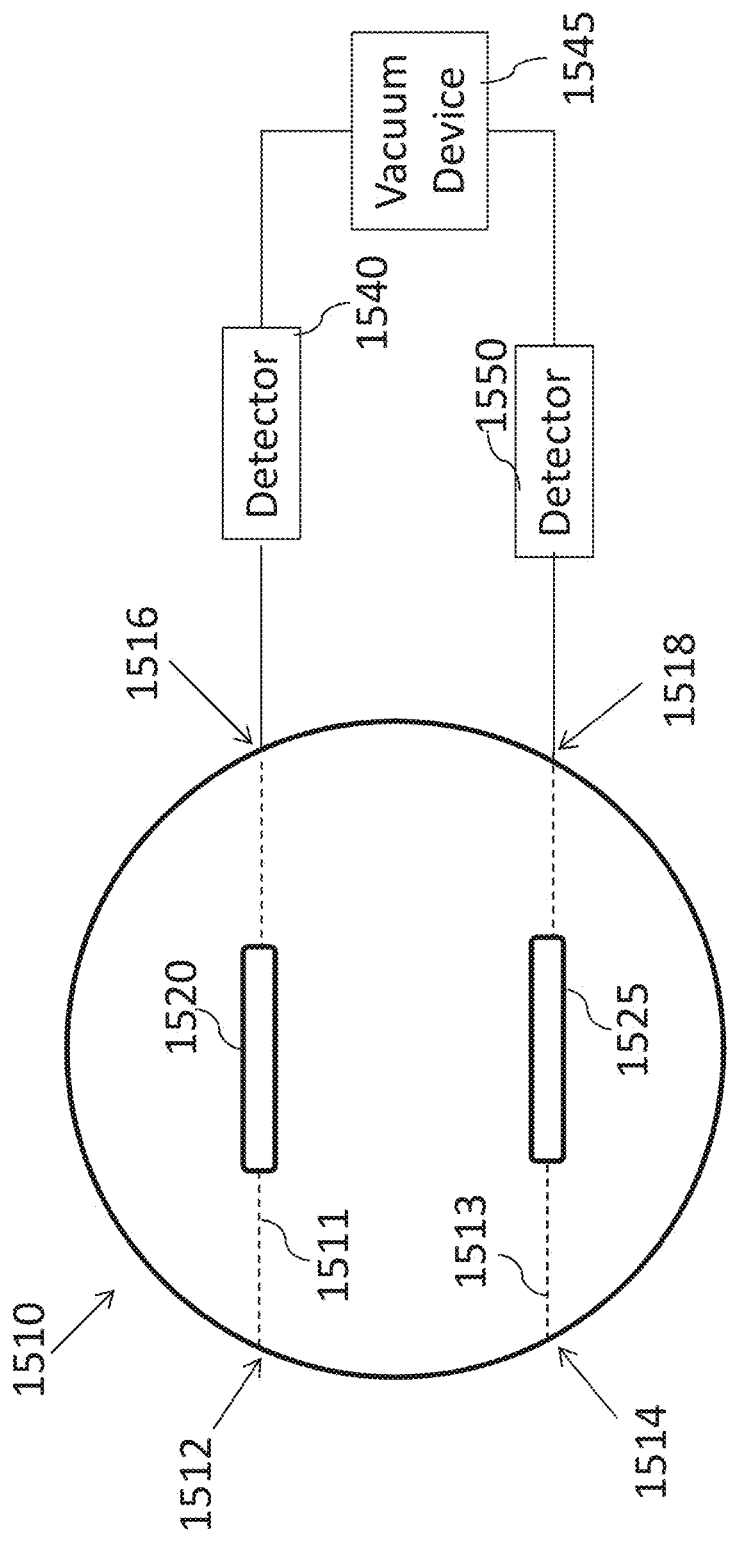
FIGS. 15A and 15B are illustrations of a system comprising a microfluidic device interface fluidically coupled to two detector and vacuum device, in accordance with certain examples.
Figure 15B:
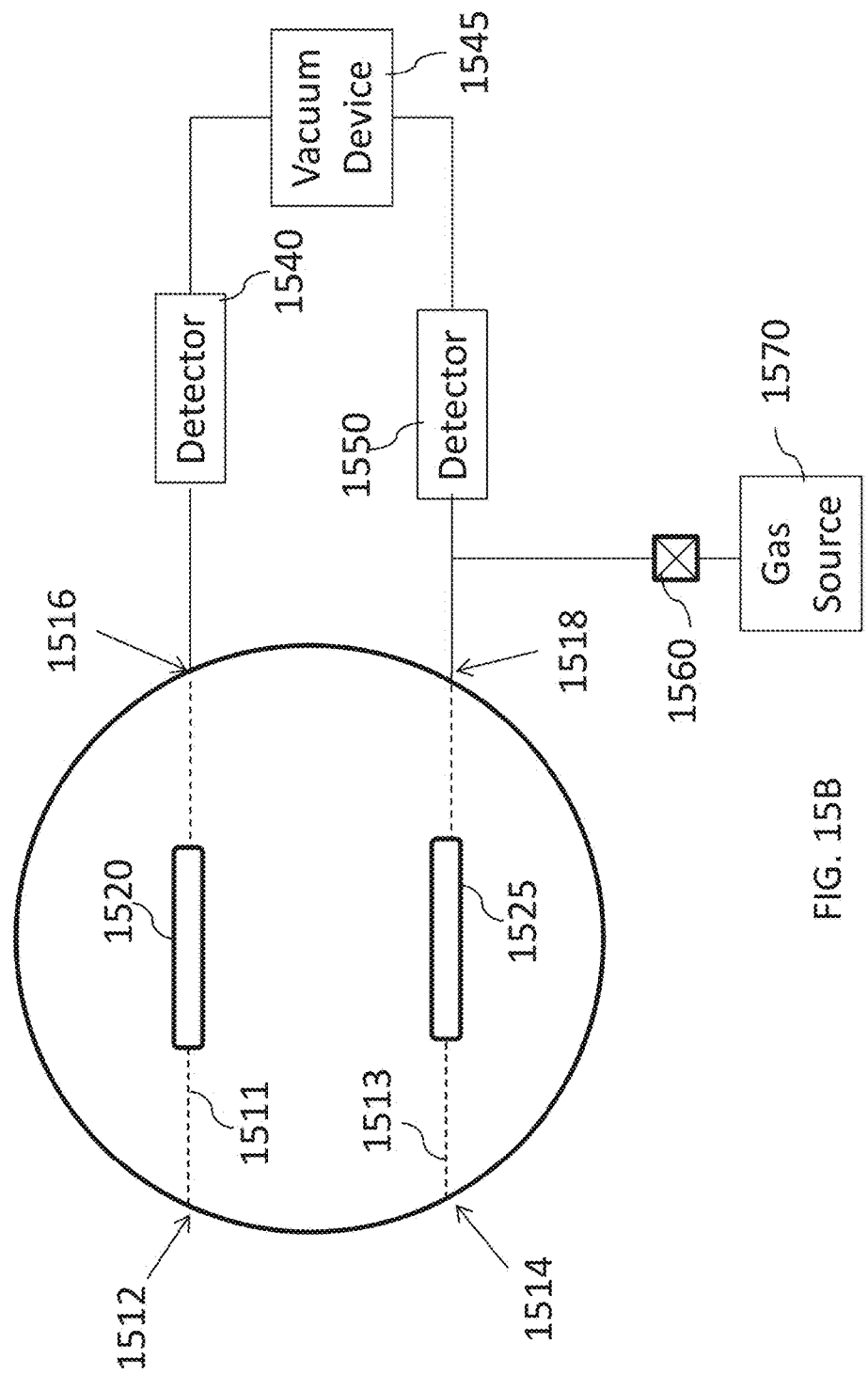

In some instances where two or more fluid output ports are present on the microfluidic device, each of the output ports may be fluidically coupled to a respective detector. For example and referring to FIG. 15A, a microfluidic device 1510 comprising a first internal microchannel 1511 comprising a first input port 1512 fluidically coupled to a first charging chamber 1520 and first output port 1516 fluidically coupled to the charging chamber 1520. The device 1510 also includes a second internal microchannel 1513 comprising a second input port 1514 fluidically coupled to a second charging chamber 1525 and a second output port 1518 fluidically coupled to the charging chamber 1525. A first detector 1540 is fluidically coupled to the first charging chamber 1520, and a second detector 1550 is fluidically coupled to the second charging chamber 1525. If desired, the detectors 1540 and 1550 can be present in a common manifold or block, e.g., as described in connection with FIG. 2. An optional vacuum device 1545 is fluidically coupled to the detectors 1540, 1550, but if desired each of the detectors 1540, 1550 may comprise its own respective vacuum device. The vacuum device 1545 is operative to accelerate flow of fluid from the outlet ports 1516, 1518 of the microfluidic device 1510 and into the detector 1540. If desired, one or more restrictors may be present between the components shown in FIG. 15A. In some instances, one or more gas sources may be fluidically coupled to the detector 1540 or to the detector 1550. In some instances only one detector comprises a gas source, whereas in other examples each detector comprises a respective gas source. Referring to FIG. 15B, a gas source 1570 may be fluidically coupled to the detector 1550 through a valve 1560. The valve 1560 may fluidically couple the gas source 1570 to the detector 1550 when the valve 1560 is in a first position. In other instances, the valve 1560 may fluidically decouple the gas source 1570 to the detector 1550 when the valve 1460 is in a second position. When the gas source 1570 and the detector 1550 are fluidically coupled, the gas source may introduce a gas to drive sample in the fluid flow path between the second charging chamber 1525 and the detector 1550 into the cell of the detector 1550. By using both a modulating gas source 1570 and a vacuum device 1545, enhanced control of sample flow into the detector 1550 can be achieved. If desired, one or more restrictors may be present between the components of the system of FIG. 15B. In some instances, the width of an internal microchannel in the device 1510 may be variable to provide restriction to fluid flow within the microchannel.

In some embodiments, the systems of FIGS. 12A-15B may comprise a detector comprising an integral vacuum device. The external vacuum device may be omitted from the system, and the vacuum device of the detector can be fluidically coupled to one or more output ports, switching valves or other components of the system to accelerate flow of sample into the detector. Where two or more detectors are present, each of the detectors may include a respective integral vacuum device, or a vacuum device of one detector may be fluidically coupled to another detector to accelerate fluid flow into both detectors.

Figure 16:
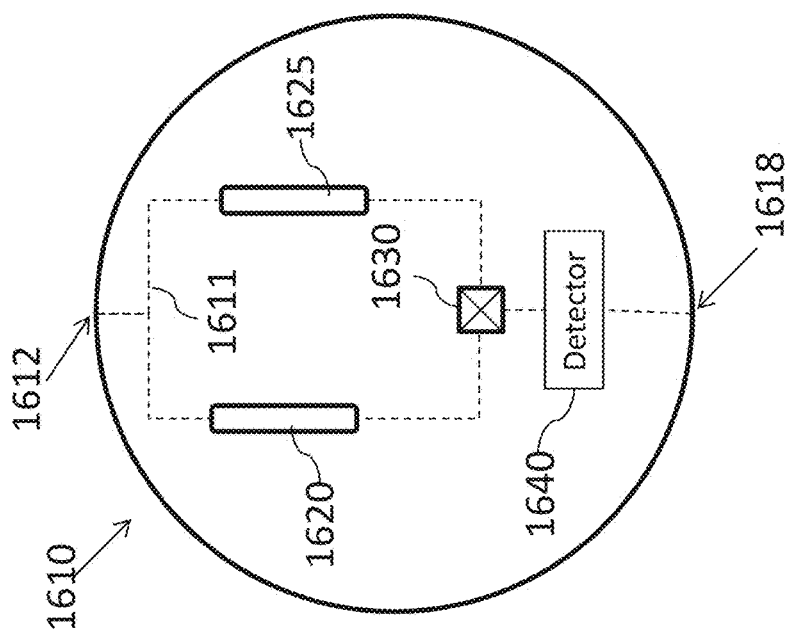
FIG. 16 is an illustration of a microfluidic device interface fluidically coupled to a detector, in accordance with certain examples.

In some configurations, the components of the systems described herein may be implemented such that the detectors are on-board the microfluidic device. By including integral detectors in the microfluidic device, a microfluidic device can be plugged into a chromatography system by making fluid and electrical connections and then analysis may be performed. Fewer fluid connections would be needed when the detector is on-board the microfluidic device. Similarly, a vacuum device may be present on the microfluidic device, or in other configurations a vacuum port may be present to fluidically couple an external vacuum device to the on-board detector. Illustrations of such devices are shown in FIGS. 16-22B. While the exact nature and type of the detectors may vary, illustrative on-board detectors typically include a filament or filaments and suitable electrical connections for receiving a current and/or providing a signal to a controller or processor. In some instances, the on-board detectors may comprise a filament cell operative as an analytical cell and another filament cell operative as a reference cell. Reference herein to charging chamber refers to a space within the microfluidic device that is configured to retain a desired volume, e.g., 5-80 microliters or other volumes. Referring to FIG. 16, a microfluidic device 1610 is shown that comprises an internal microchannel 1611 fluidic ally coupled to an input port 1612. The microchannel 1611 is also fluidically coupled to an outlet port 1618. A first charging chamber 1620 and a second charging chamber 1625 are each fluidic ally coupled to the outlet port 1618 through a switching valve 1630 and a detector 1640. If desired, the first and second charging chambers 1620, 1625 can be replaced with restrictors. An optional vacuum device (not shown) may be fluidically coupled to the detector 1640 through the outlet port 1618 to accelerate flow of sample into the detector 1640. In some configurations, the switching valve 1630 is configured to permit flow of fluid from the first charging chamber 1620 in a first position and to permit flow from the second charging chamber 1625 in a second position. If desired, one or more restrictors may be present between the components shown in FIG. 16. In some instances, one or more gas sources may be fluidically coupled to the detector 1640 through an additional input port (not shown) in the microfluidic device 1610. The gas source can be used to push sample into the detector 1640 to better control flow of sample through a flow cell of the detector 1640.

Figure 17:
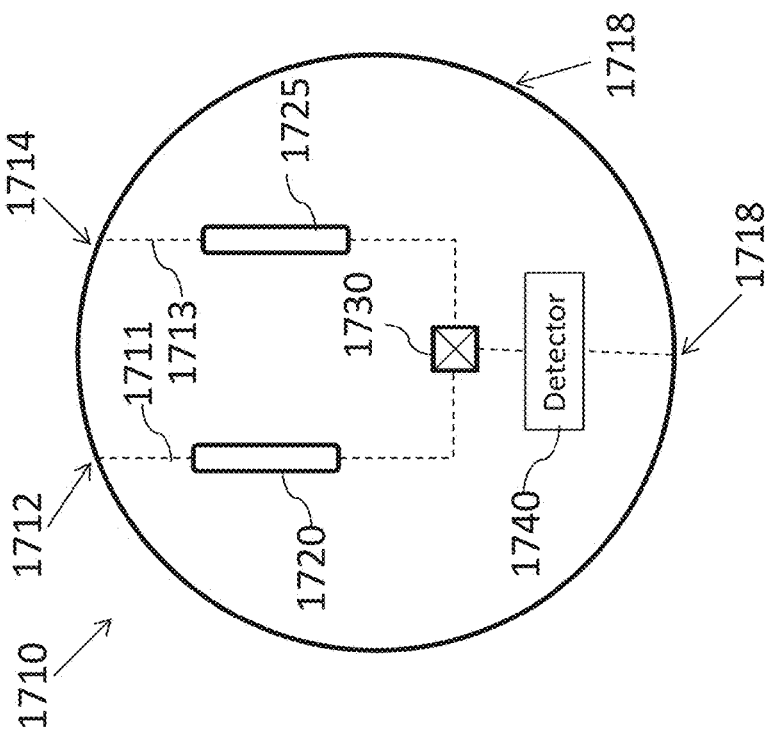
FIG. 17 is another illustration of a microfluidic device interface fluidically coupled to a detector, in accordance with certain examples.

In some configurations, each of the charging chambers may comprise a respective input port. Referring to FIG. 17, a microfluidic device 1710 is shown that comprises an internal microchannel 1711 fluidically coupled to an input port 1712. A second internal microchannel 1713 is fluidically coupled to a second input port 1714. Each of the microchannels 1711, 1713 is also fluidically coupled to an outlet port 1718. A first charging chamber 1720 and a second charging chamber 1725 are each fluidically coupled to the outlet port 1718 through a switching valve 1730 and a detector 1740. If desired, the first and second charging chambers 1720, 1725 can be replaced with restrictors. An optional vacuum device (not shown) may be fluidically coupled to the detector 1740 through the outlet port 1718 to accelerate flow of sample into the detector 1740. In some configurations, the switching valve 1730 is configured to permit flow of fluid from the first charging chamber 1720 in a first position and to permit flow from the second charging chamber 1725 in a second position. If desired, one or more restrictors may be present between the components shown in FIG. 17. In some instances, one or more gas sources may be fluidically coupled to the detector 1640 through an additional input port (not shown) in the microfluidic device 1610. The gas source can be used to push sample into the detector 1740 to better control flow of sample through a flow cell of the detector 1740.

Figure 18:
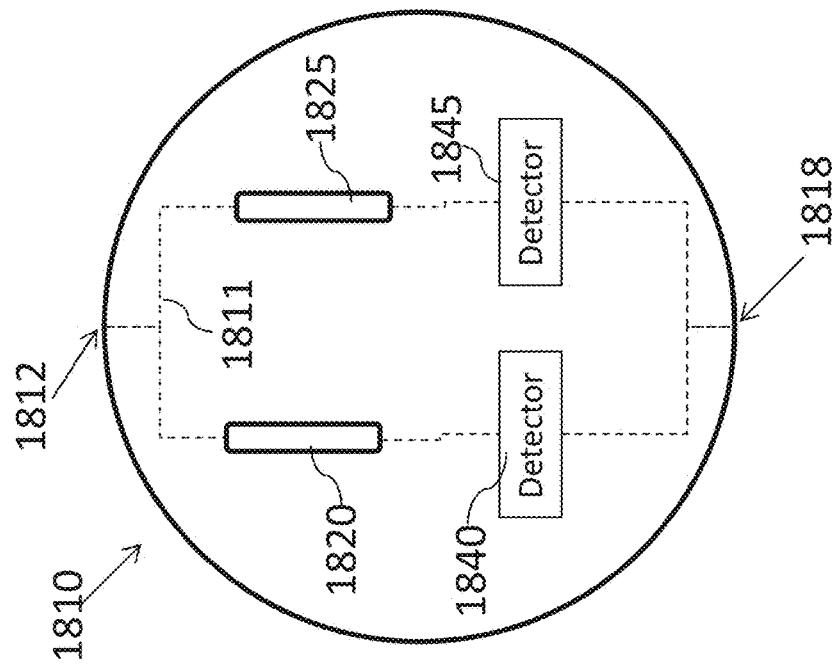
FIG. 18 is an illustration of a microfluidic device interface fluidically coupled to two detectors, in accordance with certain examples.

In some configurations, two or more on-board detectors may be present in a microfluidic device. For example, one of the detectors can be configured as a 1-filament or a 2-filament analytical cell, and the other detector can be configured as a 1-filament or a 2-filament reference cell. Referring to FIG. 18, a microfluidic device 1810 is shown that comprises an internal microchannel 1811 fluidically coupled to an input port 1812. The microchannel 1811 is also fluidically coupled to an outlet port 1818. A first charging chamber 1820 is fluidically coupled to a first detector 1840. A second charging chamber 1825 is fluidically coupled to a second detector 1845. If desired, the first and second charging chambers 1820, 1825 can be replaced with restrictors. A vacuum device (not shown) may be fluidically coupled to the detectors 1840, 1845 through the outlet port 1818 to accelerate flow of sample into the detectors 1840, 1845. In some configurations, a valve (not shown) may be present between the detectors 1840, 1845 and the outlet port 1818 so that vacuum may be provided to only one of the detectors 1840, 1845 at some period. If desired, one or more restrictors may be present between the components shown in FIG. 18. In some instances, one or more gas sources may be fluidically coupled to one or more of the detector 1840, 1845 through an additional input port (not shown) in the microfluidic device 1810. The gas source can be used to push sample into the detector 1840, the detector 1845 or both to better control flow of sample through a flow cell of one or more of the detectors 1840, 1845.

Figure 19:
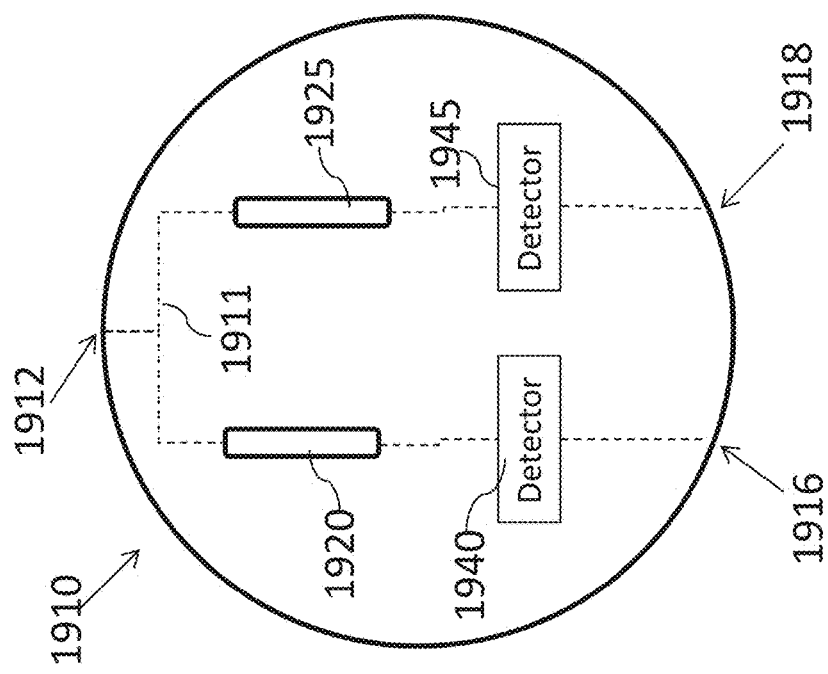
FIG. 19 is another illustration of a microfluidic device interface fluidically coupled to two detectors, in accordance with certain examples.

In some instances where two or more on-board detectors are present, each detector may comprise a respective output port so that vacuum control of each detector may be implemented independently of the other detector. Referring to FIG. 19, a microfluidic device 1910 is shown that comprises an internal microchannel 1911 fluidically coupled to an input port 1912. The microchannel 1911 is also fluidically coupled to first and second outlet ports 1916, 1918. A first charging chamber 1920 is fluidically coupled to a first detector 1940 and to the first outlet port 1916. A second charging chamber 1925 is fluidically coupled to a second detector 1945 and to the second outlet port 1918. If desired, the first and second charging chambers 1920, 1925 can be replaced with restrictors. A vacuum device (not shown) may be fluidically coupled to each of the detectors 1940, 1945 through the outlet ports 1916, 1918, respectively to accelerate flow of sample into the detectors 1940, 1945. If desired, each of the detectors 1940, 1945 may be fluidically coupled to a respective vacuum device to provide independent control of the vacuum provided to the detectors 1940, 1945. If desired, one or more restrictors may be present between the components shown in FIG. 19. In some instances, one or more gas sources may be fluidically coupled to one or more of the detector 1940, 1945 through an additional input port (not shown) in the microfluidic device 1910. The gas source can be used to push sample into the detector 1940, the detector 1945 or both to better control flow of sample through a flow cell of one or more of the detectors 1940, 1945.

Figure 20:
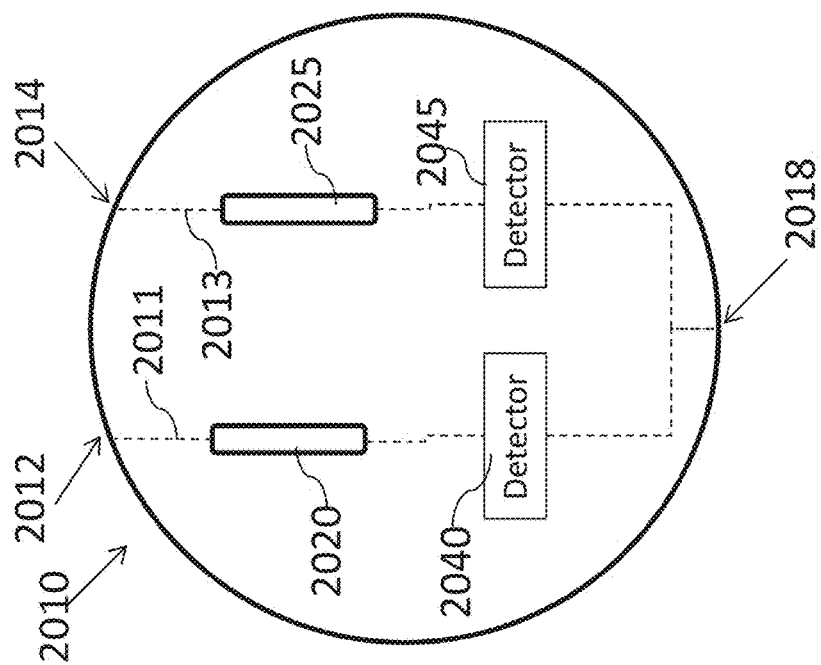
FIG. 20 is an additional illustration of a microfluidic device interface fluidically coupled to two detectors, in accordance with certain examples.

In some examples where two or more on-board detectors are present in a microfluidic device, each charging chamber may comprise its own respective input port. Referring to FIG. 20, a microfluidic device 2010 is shown that comprises an internal microchannel 2011 fluidically coupled to an input port 2012 and a first charging chamber 2020. A microchannel 2013 is also present and fluidically coupled to an inlet port 2014 and a second charging chamber 2025. Each of the first charging chamber 2020 and the second charging chamber 2025 is fluidically coupled to a respective detector 2040, 2045. If desired, the first and second charging chambers 2020, 2025 can be replaced with restrictors. An optional vacuum device (not shown) may be fluidically coupled to the detectors 2040, 2045 through the outlet port 2018 to accelerate flow of sample into the detectors 2040, 2045. In some configurations, a valve (not shown) may be present between the detectors 2040, 2045 and the outlet port 2018 so that vacuum may be provided to only one of the detectors 2040, 2045 at some period. If desired, one or more restrictors may be present between the components shown in FIG. 20. In some instances, one or more gas sources may be fluidically coupled to one or more of the detector 2040, 2045 through an additional input port (not shown) in the microfluidic device 2010. The gas source can be used to push sample into the detector 2040, the detector 2045 or both to better control flow of sample through a flow cell of one or more of the detectors 2040, 2045.

Figure 21:
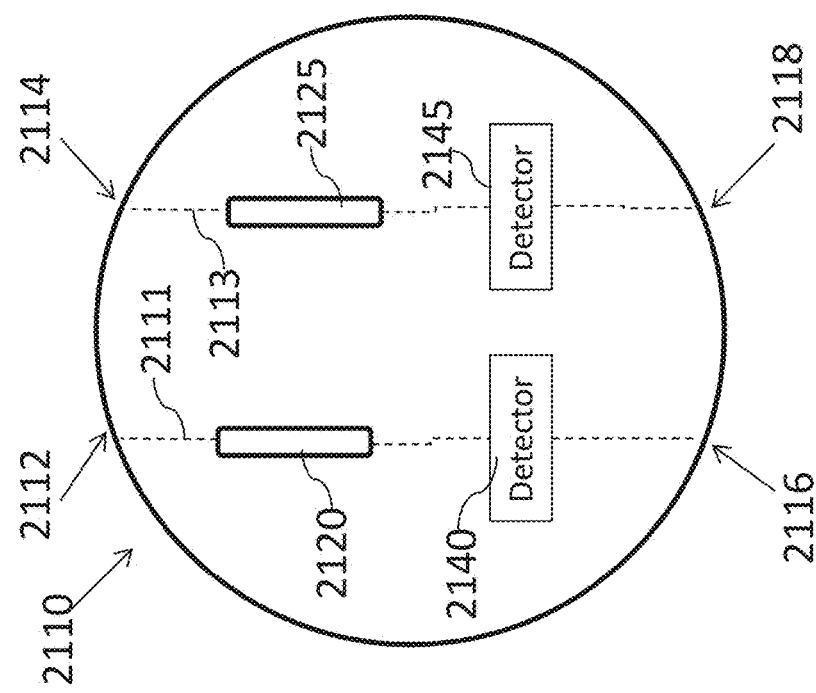
FIG. 21 is another illustration of a microfluidic device interface fluidically coupled to two detectors, in accordance with certain examples.

In some instances where two or more on-board detectors are present, each charging chamber may comprise its own respective input port and each detector may comprise a respective output port so that vacuum control of each detector may be implemented independently of the other detector. Referring to FIG. 21, a microfluidic device 2110 is shown that comprises an internal microchannel 2111 fluidically coupled to an input port 2112, a first charging chamber 2120 and a first outlet port 2116. A second microchannel 2113 is also present and is fluidically coupled to an inlet port 2014, a second charging chamber 2125 and a second outlet port 2118. Each of the first charging chamber 2120 and the second charging chamber 2125 is fluidically coupled to a respective detector 2140, 2145. If desired, the first and second charging chambers 2120, 2125 can be replaced with restrictors. An optional vacuum device (not shown) may be fluidically coupled to each of the detectors 2140, 2145 through the outlet ports 2116, 2118, respectively to accelerate flow of sample into the detectors 2140, 2145. If desired, each of the detectors 2140, 2145 may be fluidically coupled to a respective vacuum device to provide independent control of the vacuum provided to the detectors 2140, 2145. In some instances, one or more restrictors may be present between the components shown in FIG. 21. In some instances, one or more gas sources may be fluidically coupled to one or more of the detector 2140, 2145 through an additional input port (not shown) in the microfluidic device 2110. The gas source can be used to push sample into the detector 2140, the detector 2145 or both to better control flow of sample through a flow cell of one or more of the detectors 2140, 2145.

Figure 22B:
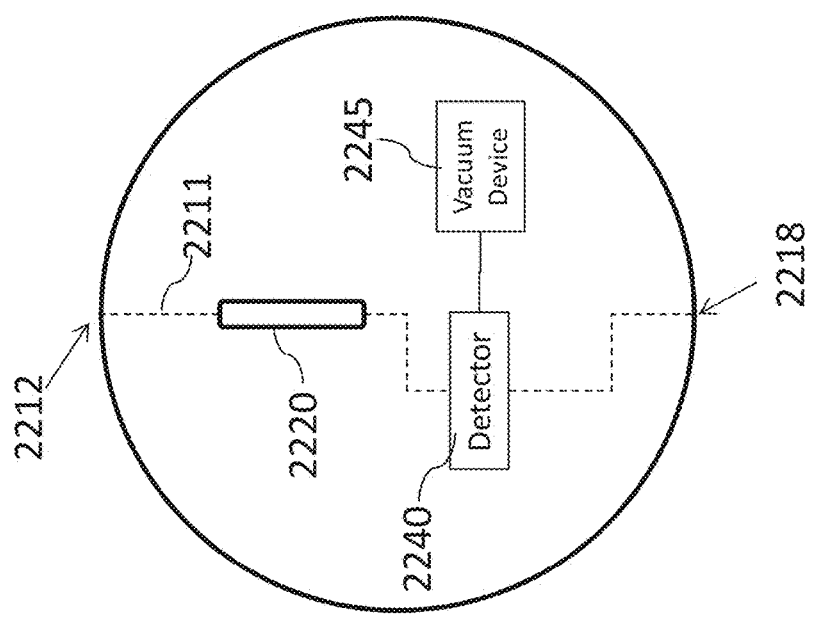
FIGS. 22A and 22B are illustrations of a microfluidic device including an on-board vacuum device, in accordance with certain examples.
Figure 22A:
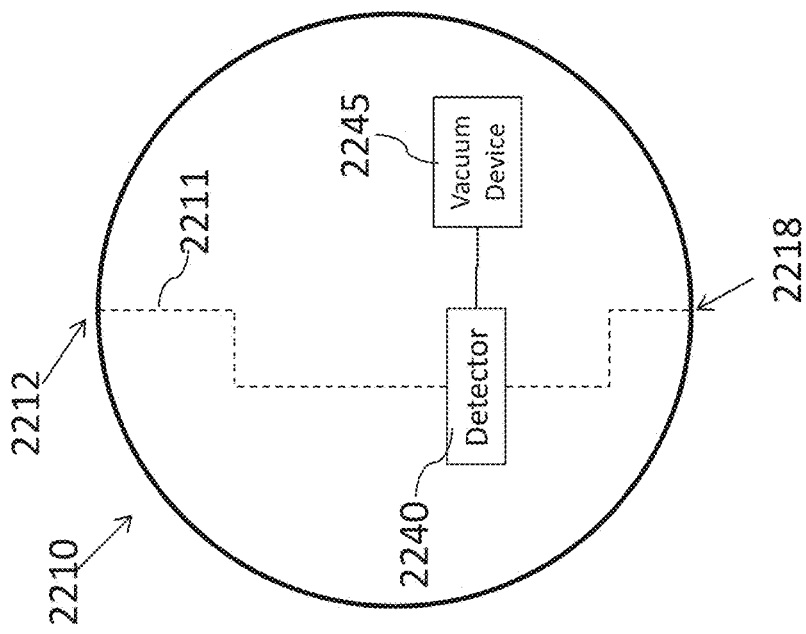

In certain configurations, a microfluidic device may comprise an on-board detector and an on-board vacuum device. Referring to FIG. 22A, a microfluidic device 2200 comprises an internal microchannel 2211 fluidically coupled to an input port 2212 and a detector 2240. The detector 2240 is fluidically coupled to an outlet port and an on-board vacuum device 2245. In some instances, one or more restrictors may be present between the components shown in FIG. 22A. In certain configurations, the internal microchannel 2211 may comprise one or more charging chambers as shown in FIG. 22B (see charging chamber 2220). The charging chamber 2220 provides a defined volume to permit accumulation of sample. In another configuration, the charging chamber 2220 can be replaced with a restrictor. In some instances, one or more valves may be present between the detector 2240 and the charging chamber 2220 to permit sample to accumulate in the charging chamber 2220 prior to introduction into the detector 2240. If desired, two or more separate internal microchannels or two or more separate charging chambers may be present in the devices of FIGS. 22A and 22B. In addition, two or more detectors, two or more vacuum devices and one or more gas sources may also be present or used with the devices shown in FIGS. 22A and 22B. In some configurations, the vacuum device 2245 can be replaced with an on-board restrictor to permit fluidic coupling of the restrictor to an external gas source. The external gas source can be used to push sample into the detector as described, for example, in connection with FIG. 2.

In certain embodiments and referring to FIG. 23, an illustration of certain system components are shown. The system 2300 comprises an injector 2310 (or other sample introduction device, e.g., gas sampling valve, thermal desorption apparatus, headspace injector, etc.) fluidically coupled to a mobile phase source 2315. A chromatography column 2320 is fluidically coupled to the injector 2310. Fixed restrictors 2332, 2334 are present between the column 2320 and a detector 2340. The detector 2340 is shown in FIG. 23 as a 4-filament detector though other detectors may be used instead. If desired, the 4-filament detector 2340 can be present in a manifold or block that can be fluidically coupled to other components of the system 2300. In other configurations, the restrictors 2332, 2334 and the detector 2340 are present in a common manifold or block. An excess flow outlet or vent 2335 may be present (either separately or in the common manifold or block). The outlet 2335 may be open, unrestricted vent or pressure or flow controlled vent using a fixed inner diameter restrictor, adjustable restrictor, pressure regulator, needle valve, or frit, for example. A second gas source 2336 may be present to provide a reference or makeup mobile phase. Various valves may be present between the second gas source 2336 and the detector 2340. A fixed restrictor 2342 can be downstream of the detector 2340 and present between the detector 2340 and a flow stabilizer 2345. An optional vacuum device 2350 is fluidically coupled to the detector 2340 through the fixed restrictor 2342 and the flow stabilizer 2345. Flow of samples into the detector 2340 can be controlled, for example, using the fixed restrictors 2332, 2334 which function as if the column oven were operating isothermally and can assist in stabilizing the system baseline. The inlets to the restrictors can be supplied with an excess flow of carrier gas to permit operation of the detector 2340 with a column effluent flow rate less than the detector flow. By decoupling the flow rate through the detector 2340 and the flow rate through the column 2320, better control of sample flow through the detector 2340 can be achieved.

If desired, a microfluidic device can be used in the system shown in FIG. 23. Referring to FIG. 24, the system 2400 comprises an injector 2410 (or other sample introduction device, e.g., gas sampling valve, thermal desorption apparatus, headspace injector, etc.) fluidically coupled to a mobile phase source 2415. A chromatography column 2420 is fluidically coupled to the injector 2410. Fixed restrictors are present in the internal microchannels of a microfluidic device 2435 present between the column 2420 and a detector 2440. The detector 2440 is shown in FIG. 24 as a 4-filament detector though other detectors may be used instead. If desired, the microfluidic device 2435 and filament detector 2440 can be integrated into a common manifold or block to provide for easier connection of the various components of the system 2400 and/or to permit enhanced temperature control of these components. In other configurations, the detector 2440 can be integrated into a common manifold or block and the microfluidic device 2435 may be separate. An optional outlet port 2436 may be present in the microfluidic device or present in a common manifold that comprises the detector 2440. The outlet 2436 may be open, unrestricted vent or pressure or flow controlled vent using a fixed inner diameter restrictor, adjustable restrictor, pressure regulator, needle valve, or frit, for example. A second gas source 2437 may be present to provide a reference or makeup mobile phase. Various valves may be present between the second gas source 2437 and the detector 2440. A fixed restrictor 2442 can be downstream of the detector 2440 and is present between the detector 2440 and a flow stabilizer 2445. A vacuum device 2450 is fluidically coupled to the detector 2440 through the fixed restrictor 2442 and the flow stabilizer 2445. Flow of sample into the detector 2440 can be controlled, for example, using the vacuum device 2450 to accelerate sample into the detector 2440. By introducing gas from the gas source 2437, flow of sample through the detector 2440 can be decoupled from flow of sample through the column 2420.

In certain configurations, it may be desirable to include one or more additional components to provide a pressure differential across different fluid channels of the detector. Referring to FIG. 25, a system 2500 comprises an injector 2510 (or other sample introduction device, e.g., gas sampling valve, thermal desorption apparatus, headspace injector, etc.) fluidically coupled to a mobile phase source 2515. A chromatography column 2520 is fluidically coupled to the injector 2510. Fixed restrictors 2532, 2534 are present between the column 2520 and a detector 2540. The detector 2540 is shown in FIG. 25 as a 4-filament detector though other detectors may be used instead. In some instances, the detector 2540 (and restrictors 2532, 2534) can be present in a manifold or block to permit coupling of the various fluid lines to the detector 2540 in a rapid manner. An excess flow outlet including a restrictor 2542 may be present to provide a pressure differential across the restrictors 2532, 2534 to balance the fluid pressures in the system. The excess flow outlet can be present in the common manifold that includes the detector 2540 or may be separate from the manifold. A second gas source 2536 may be present to provide a reference or makeup mobile phase. Various valves may be present between the second gas source 2536 and the detector 2540. An optional vacuum device (not shown) may be fluidically coupled to the detector 2540 if desired. The gas source 2536 can be used to introduce a make-up gas to better control flow of sample through the detector 2540.

In some examples, a microfluidic device can be used in the system shown in FIG. 25. Referring to FIG. 26, the system 2600 comprises an injector 2610 (or other sample introduction device, e.g., gas sampling valve, thermal desorption apparatus, headspace injector, etc.) fluidically coupled to a mobile phase source 2615. A chromatography column 2620 is fluidically coupled to the injector 2610. Fixed restrictors are present in the internal microchannels of a microfluidic device 2635 present between the column 2620 and a detector 2640. The detector 2640 is shown in FIG. 26 as a 4-filament detector though other detectors may be used instead. In certain configurations, the detector 2640 can be configured as a manifold or block that is fluidically coupled to the various other components of the system. If desired, the microfluidic device 2635 can also be present in this manifold or block or may be separate from the manifold or block. An outlet port comprising a restrictor 2642 may be present in the microfluidic device 2635. A second gas source 2636 may be present to provide a reference or makeup mobile phase. Various valves may be present between the second gas source 2636 and the detector 2640. A vacuum device (not shown) can be fluidically coupled to the detector 2640 if desired. By introducing gas from the gas source 2636, flow of sample through the detector 2440 can be decoupled from flow of sample through the column 2620.

Figure 27:
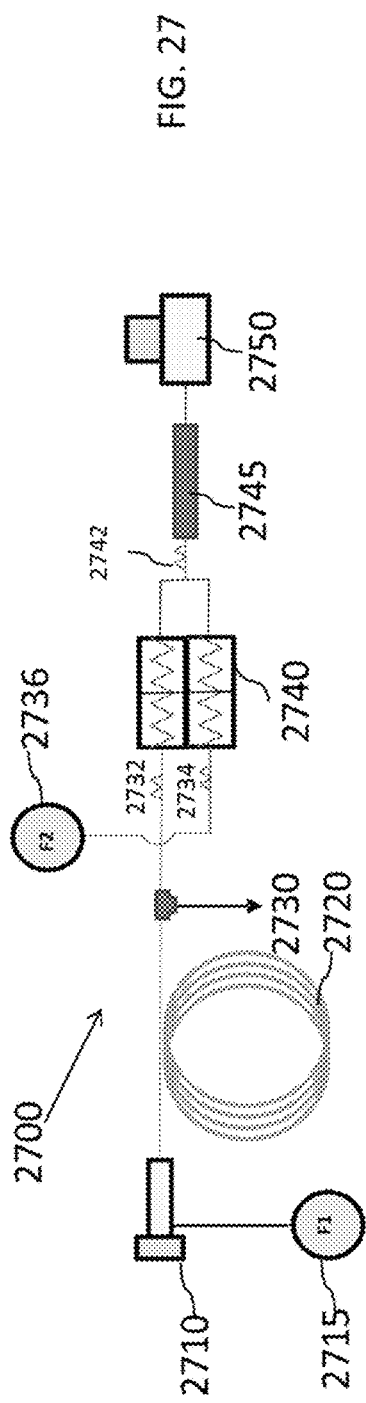
Figure 28:
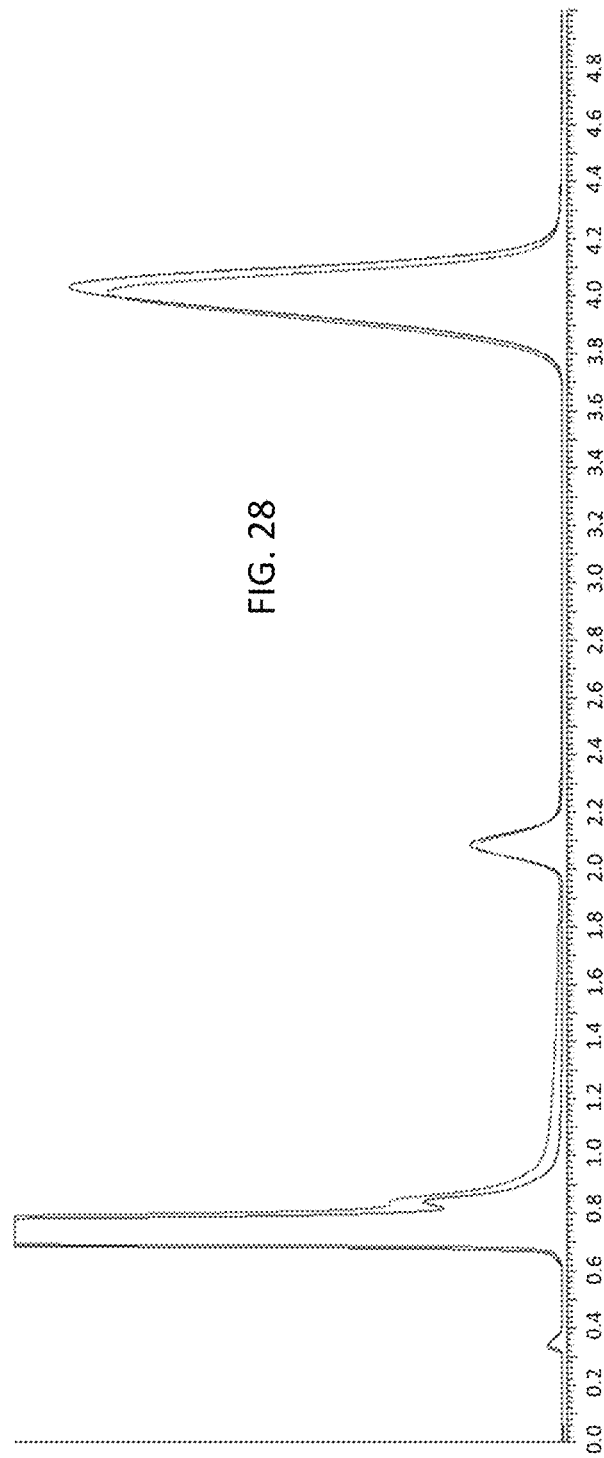
FIG. 28 is an illustrative chromatogram based on the system of FIG. 27, in accordance with certain configurations.

In some embodiments, it may be desirable to place the detector in parallel with another sensor or detector by using a fraction of a higher carrier flow column effluent. If the detector is a concentration dependent detector, the detector signal with the low flow/sub-ambient pressure operation of the detector is similar to the signal generated by the full column effluent flow through the detector at ambient pressure. One configuration is illustrated in the system of FIG. 27 and the graph shown in FIG. 28. Referring to FIG. 27, the system 2700 comprises an injector 2710 (or other sample introduction device, e.g., gas sampling valve, thermal desorption apparatus, headspace injector, etc.) fluidically coupled to a mobile phase source 2715. A chromatography column 2720 is fluidically coupled to the injector 2710. Restrictors 2732, 2734 are present between the column 2720 and the detector 2740. If desired, the detector 2740 and restrictors 2732, 2734 can be integrated into a common manifold or block as described, for example, in connection with FIG. 2. An outlet port 2730 is present that can provide sample to a different detector or sensor (not shown). The outlet port 2730 can be integrated into the common manifold or may be separate. A second gas source 2736 may be present to provide a reference or makeup mobile phase. Various valves may be present between the second gas source 2736 and the detector 2740. A fixed restrictor 2742 is downstream of the detector 2740 and is present between the detector 2740 and a flow stabilizer 2745. An optional vacuum device 2750 is fluidically coupled to the detector 2740 through the fixed restrictor 2742 and the flow stabilizer 2745. Flow of sample into the detector 2740 can be controlled, for example, using the vacuum device 2750 to accelerate sample into the detector 2740 or using the makeup gas to push sample into the detector 2740 or both. As illustrated in the chromatogram shown in FIG. 28, a low flow through the system 2700 is anticipated to be substantially the same as the flow through a normal system. The graph shows two expected curves overlaid onto each other. The peak shape and peak height is about the same for the different flows. The x-axis of the graph begins at 0.0 minutes and increase in increments of 0.2 minutes until terminating at 5.2 minutes. The y-axis shows the relative intensity.

In some configurations, certain detectors, e.g., TCDs, functioning at sub-ambient pressure conditions with a low effective cell volume, e.g., 5-30 microliters or 5-20 microliters or 5-10 microliters, can be useful in series with a different detector such as a mass spectrometer. The other detector, however, may be negatively affected by high concentrations of a component (oxygen, for example). The detector could be used as a safety device as well as for quantification of components that are out of the operating range of the other detector. One arrangement of a system is shown in FIG. 29. The system 2900 comprises an injector 2910 (or other sample introduction device, e.g., gas sampling valve, thermal desorption apparatus, headspace injector, etc.) fluidically coupled to a mobile phase source 2915. A chromatography column 2920 is fluidically coupled to the injector 2910. Restrictors 2932, 2934 are present between the column 2920 and the detector 2940. If desired, the restrictors 2932, 2934 and the detector 2940 can be integrated into a manifold or block to facilitate fluidic coupling to other components in the system. A second gas source 2936 may be present to provide a reference or makeup mobile phase. Various valves may be present between the second gas source 2936 and the detector 2940. A fixed restrictor 2942 is downstream of the detector 2940 and is present between the detector 2940 and a mass spectrometer 2960 fluidically coupled to the detector 2940. Another fixed restrictor 2944 is present between the detector 2940 and a flow stabilizer 2945. The flow stabilizer 2945 is fluidically coupled to a vacuum device 2950. Flow of sample into the detector 2940 can be controlled, for example, using the vacuum device 2950 to accelerate sample into the detector 2940 or using the gas source 2936 to push sample into the detector 2940 or both. The mass spectrometer 2960 can receive sample from the detector 2940 and may analyze the sample using one or more techniques commonly implemented in mass spectrometry.

Figure 30B:
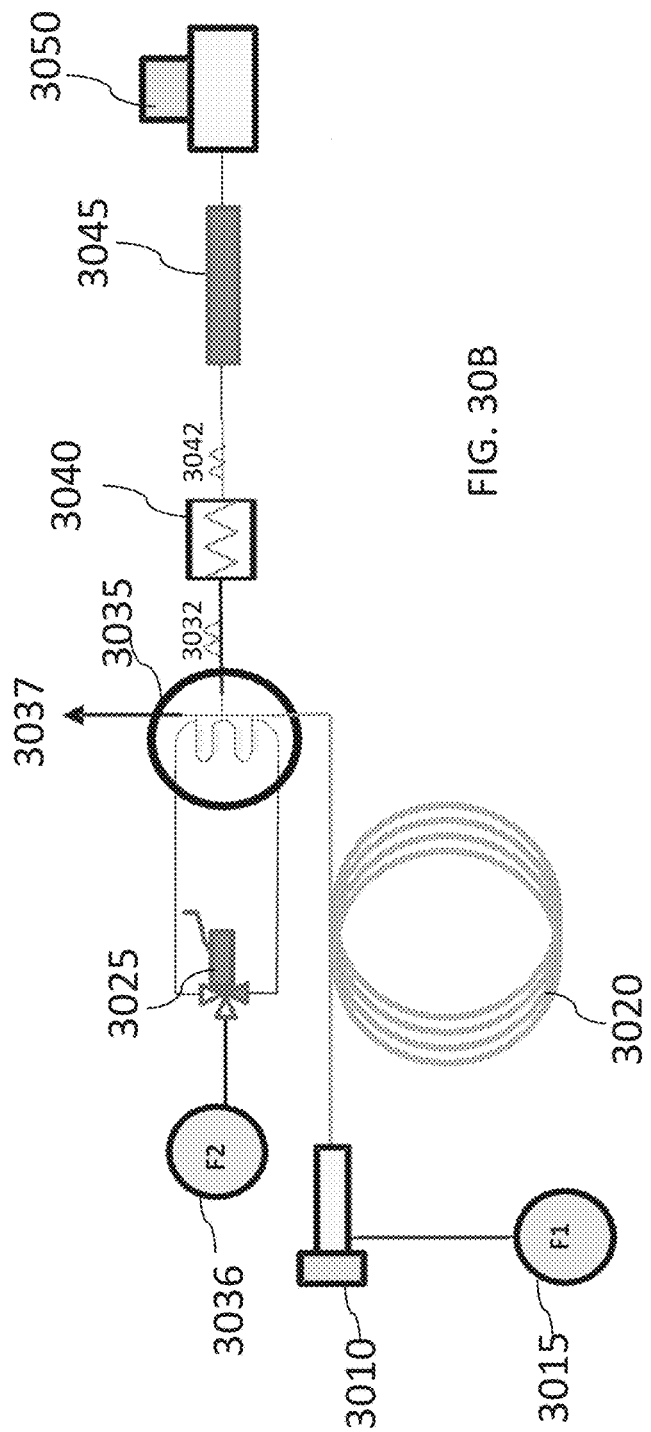

In some instances, the systems described herein may implement a gas source in combination with one or more restrictors to control flow of fluid in the system. Referring to FIGS. 30A and 30B, systems are shown comprising an injector 3010 (or other sample introduction device, e.g., gas sampling valve, thermal desorption apparatus, headspace injector, etc.) fluidically coupled to a mobile phase source 3015. A chromatography column 3020 is fluidically coupled to the injector 3010. A second mobile phase gas source 3036 may be fluidically coupled to a microfluidic device 3035 through a solenoid valve 3035 (or other valve). The solenoid valve can be used to fluidically couple and decouple the column 3020 from the detector 3040 to direct reference and column effluent to the detector 3040. If desired, the detector 3040 and restrictor 3032 can be integrated into a block or manifold. An output port 3037 may be present in the microfluidic device 3035 to vent the system or to provide effluent to another component. A restrictor 3032 is present between the detector 3040 and the microfluidic device 3035 to control fluid flow in the system 30000. As shown in FIG. 30B, a vacuum source 3050 may be fluidically coupled to the detector 3040 through a flow stabilizer 3045. If desired, the vacuum source 3050, detector 3040 and flow stabilizer 3045 can be integrated into a block or manifold.

Figure 31A:
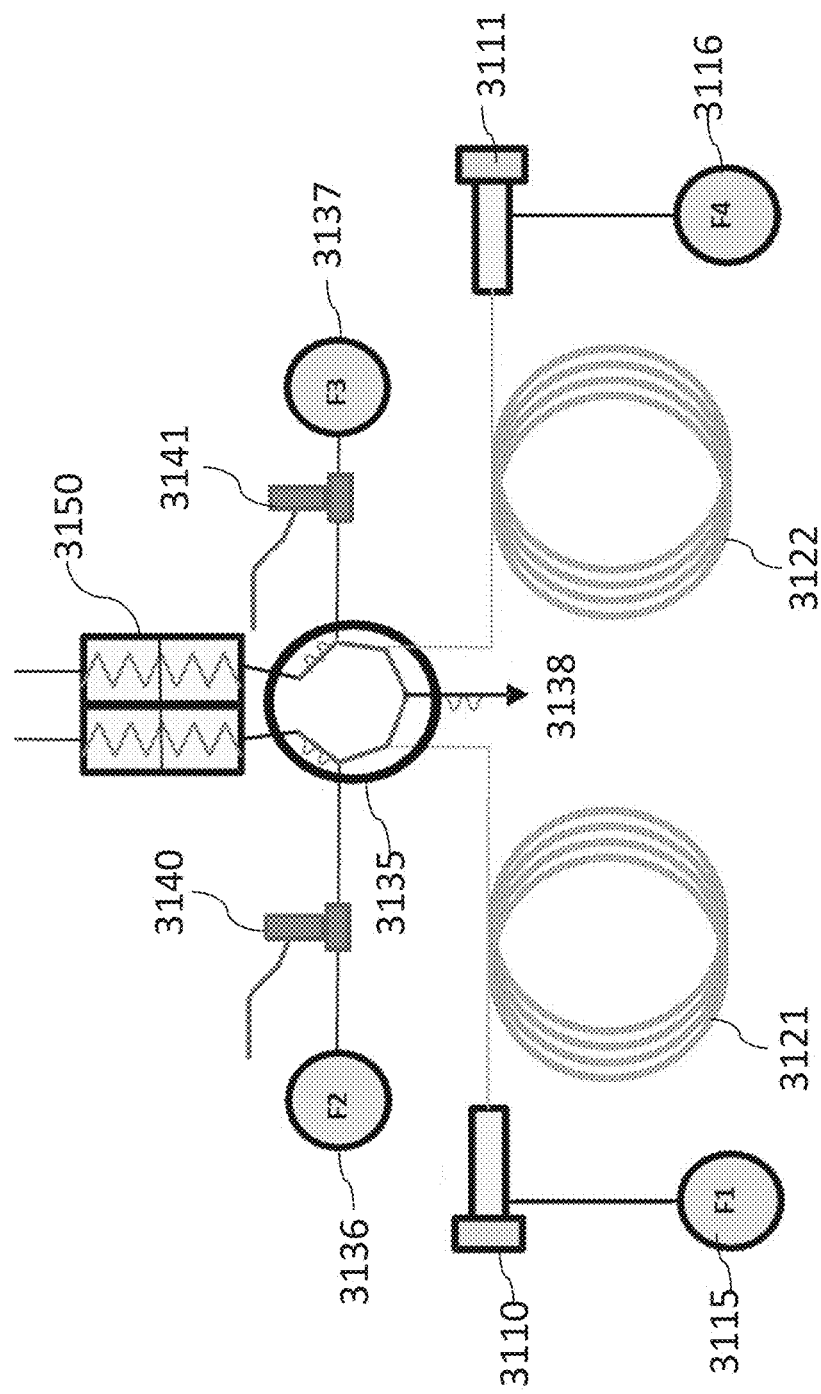
Figure 31B:
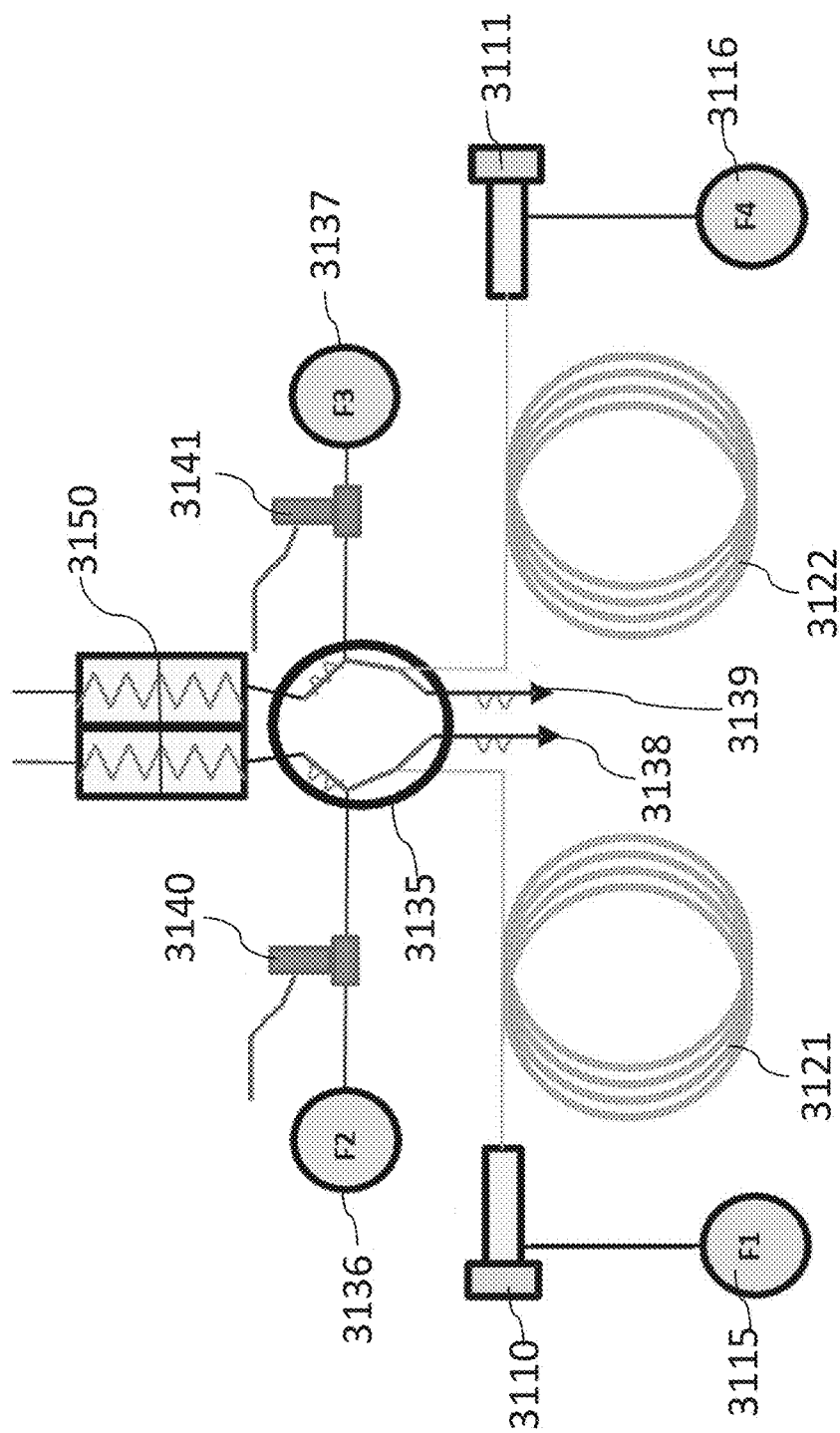

In some embodiments, the interfaces described herein may be used to multiplex multiple different columns through one or more detectors. Illustrative systems are shown in FIGS. 31A and 31B. Referring to FIG. 31A, the system 3100 comprises a first injector 3110 (or other sample introduction device) fluidically coupled to a first mobile phase source 3115. A second injector 3111 (or other sample introduction device) is fluidically coupled to a second mobile phase source 3116. Each of the injectors 3110, 3111 is fluidically coupled to a column 3121, 3122, respectively. The columns 3121, 3122 are each fluidically coupled to a microfluidic device 3135 that comprises an internal microchannel and internal restrictors. The microfluidic device 3135 is fluidically coupled to gas sources 3236, 3237 through valves 3140, 3141, respectively. The gas sources 3236, 3237 can be used to provide a reference or makeup mobile phase that can enhance flow of sample into a detector 3150. The gas sources 3236, 3237 can include one or more pumps to pressurize the system 3100. A detector 3150 is fluidically coupled to outlet ports of the microfluidic device 3135 and can be operated in parallel to receive sample from both columns 3121, 3122 at the same time. The detector 3150 can be present in a manifold or block, if desired, along with one or more restrictors. One or more output ports 3138, 3139 may be present to vent excess flow or provide column effluent to another detector or to another component. An optional vacuum device (not shown) can be fluidically coupled to the detector 3150, if desired, to accelerate fluid flow into the detector 3150.

In certain examples, the detector used in the systems and devices described herein may take many forms. Common detectors include those which are used in gas and liquid chromatography applications. For example, detectors which provide a signal based on a change in current or voltage are desirably used in the systems and devices described herein. Illustrative detectors include a flame ionization detector, a thermal conductivity detector and other detectors which may include one or more filaments or wires that can be charged. The exact configuration of the detector can vary from a single filament or two or more filaments. In some instances, the detector may comprise two or more separate flow cells which may comprise the same or a different number of filaments, e.g., 2 filaments can be present in each cell. In certain configurations, one flow cell can be used as an analytical cell to receive sample, and the other flow cell can be used as a reference cell. In certain embodiments, the exact volume of the TCD cell used can vary. As noted herein, illustrative volumes can vary from about 5 microliters to about 100 microliters, e.g., about 10 microliters to about 70 microliters or about 10 microliters to about 50 microliters. Where two or more different cells are present in a single device, the volume of the cells may be the same or may be different. In some instances, the volume of each cell is about 5 microliters to about 20 microliters, more particularly about 10 microliters to about 20 microliters or about 5 microliters to about 15 microliters. The exact shape of the TCD cell can also vary, and in some instances, the cell can be symmetric about one or more axes whereas in other instances the cell can be asymmetric about one or more axes, e.g., a longitudinal axis.

Figure 32:
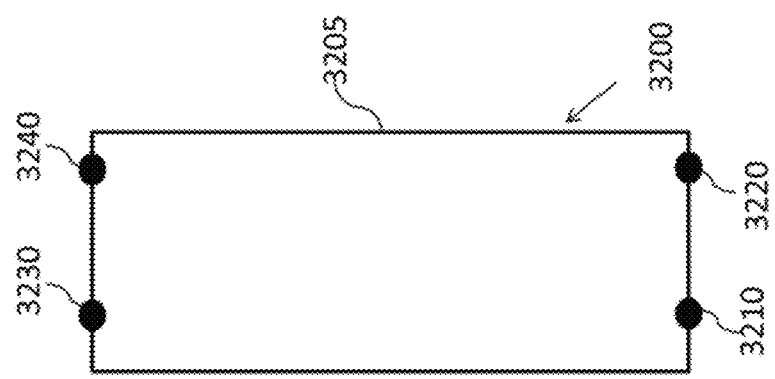
FIG. 32 is an illustration showing a manifold housing, in accordance with certain configurations.

In certain embodiments, the detectors described herein can include a generally integral housing comprising internal microchannels, internal restrictors, internal detectors and external ports to fluidically couple the various internal components to external fluid components of a system. For example, and referring to FIG. 32, an illustration of a filament detector manifold 3200 is shown. The interface 3200 generally comprises an integral block 3205 that comprises a sample inlet port 3210, a reference/make-up gas port 3220, a common vent port 3230 and a make-up gas vent port 3240. As sample enters into the manifold 3200 through the inlet 3210, sample encounters a first internal restrictor between the sample inlet 3210 and sample filaments of an analytical cell. The sample can then be vented through the common vent 3230. Make-up gas can enter the manifold through the inlet 3220. A restrictor can be present between the inlet 3220 and reference filaments. Make-up gas can then exit through the common vent 3230. The make-up gas vent 3240 is fluidically coupled to both the inlet 3210 and the inlet 3220 to assist in controlling the pressure in the manifold 3200.

Certain specific examples are described to facilitate a better understanding of the technology described herein.

Example 1

Figure 33A:
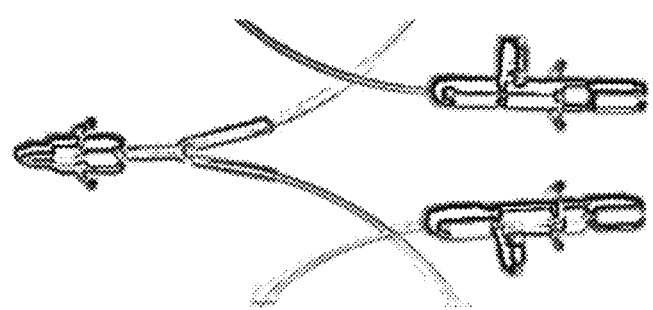
FIG. 33A is a line drawing produced from a photograph of an interface, in accordance with certain examples.
Figure 33B:
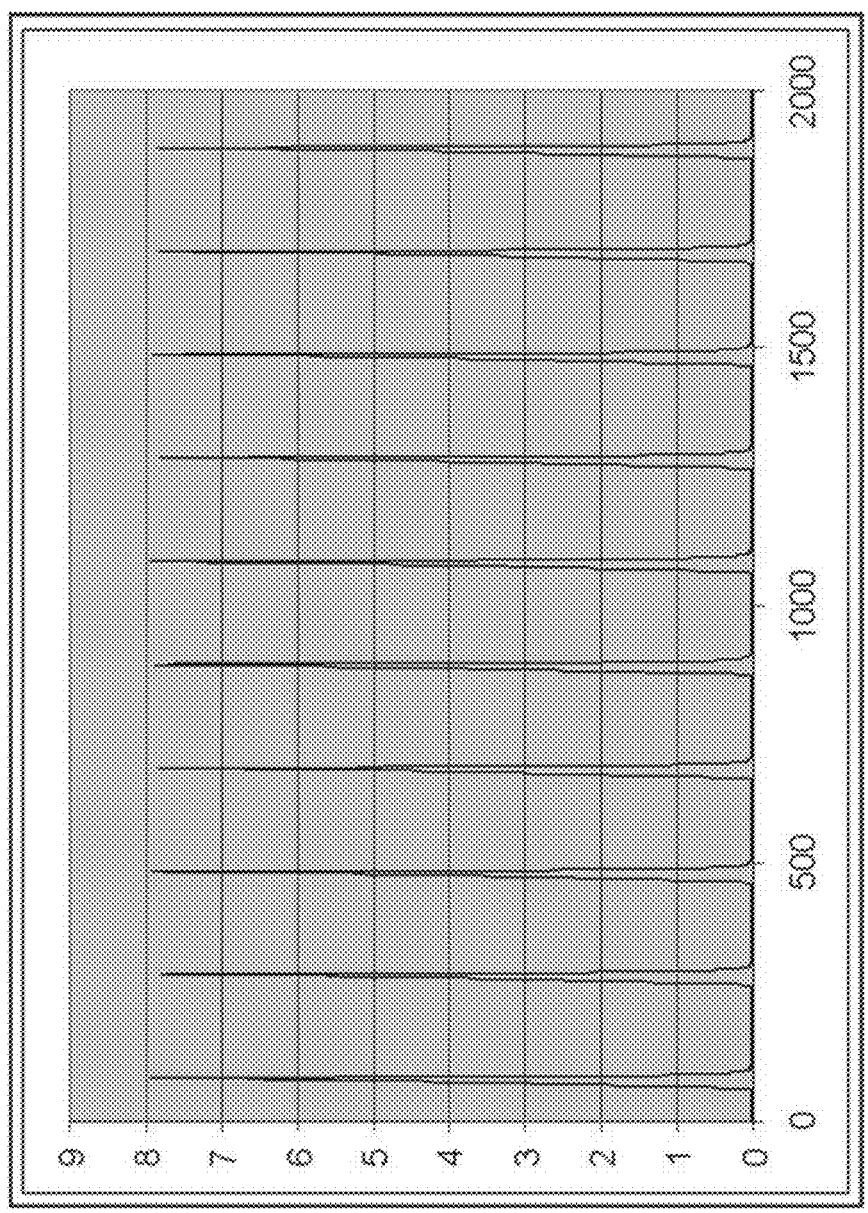
FIG. 33B shows a typical modulation profile, in accordance with certain examples.
Figure 34A:
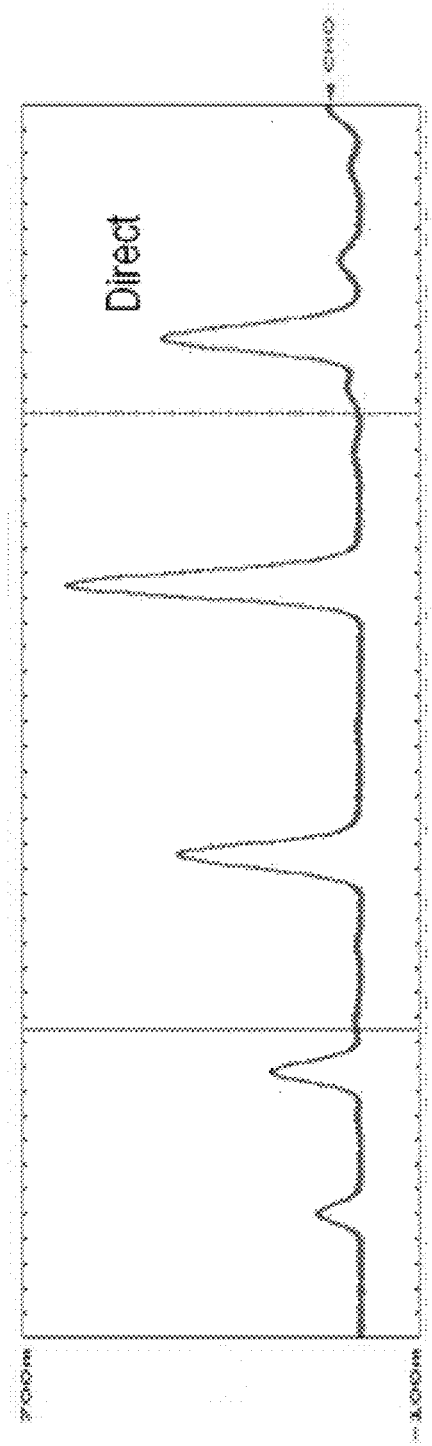
FIGS. 34A and 34B are flame ionization detector chromatograms of a modulated and an unmodulated test sample, in accordance with certain examples.
Figure 34B:
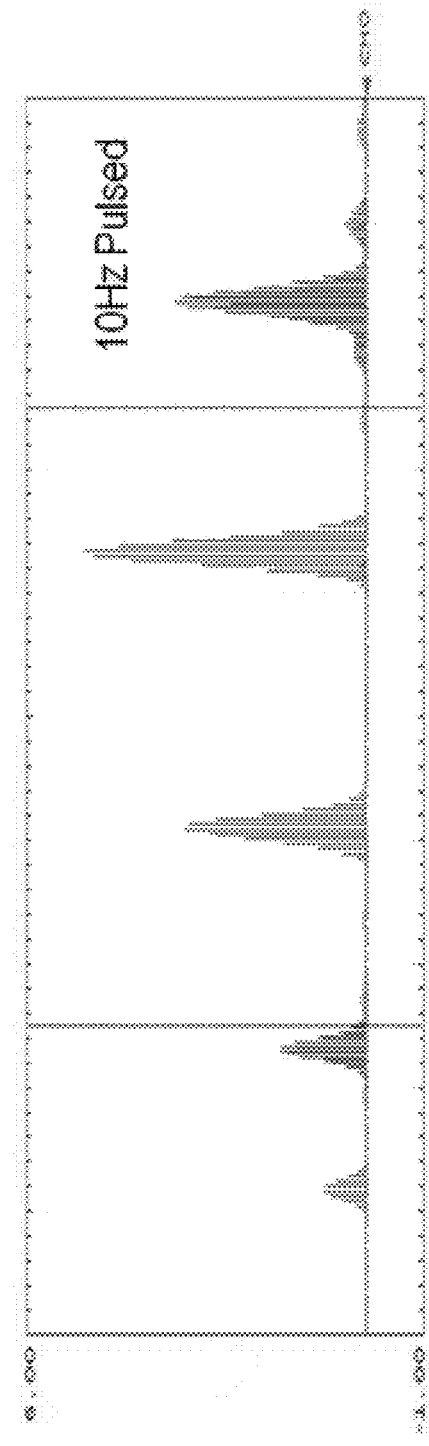

A two-chamber device (see FIG. 33A) was constructed using unions and fused silica tubing. The charge tubes are the lengths of fused silica tubing connected to the T-pieces at the bottom of this photograph. A signal generator was used to deliver a square wave voltage to a 3-way solenoid valve that supplied the switched sweep gas to the side ports on these T-pieces. This first implementation was tested on a flame ionization detector with column carrier gas doped with methane to provide a response on that detector. FIG. 33B shows a typical modulation profile for this system using a flame ionization detector (FID) and a 5 Hz modulated carrier gas doped with methane The system was then further tested with chromatography with an example shown in FIGS. 34A and 34B. Initial (FID) data represents un-modulated (labeled as Direct and in FIG. 34A) and 10 Hz modulated (FIG. 34B) chromatograms of a standard FID test mixture. A significant increase in peak height is observed in the modulated data. This result is consistent with the sample mass flow rate being increased into the FID as a result of the modulation. The concentration should not change so no increase on TCD peak height would be expected.

Example 2

A second device was constructed similar to the devices described in commonly assigned U.S. Pat. No. 8,303,694. FIG. 35 shows a schematic of the microfluidic device with a first layer 3510 and a second layer 3520 shown in an exploded view to permit viewing of the internal microchannels. An external solenoid valve 3530 was present to switch the effluent from the column 3505 between two external lengths of fused silica tubing that served as the charge tubes. The output from the charge tubes were combined in a SGE SilFlow™ 3-port splitter device.

Example 3

Figure 36:
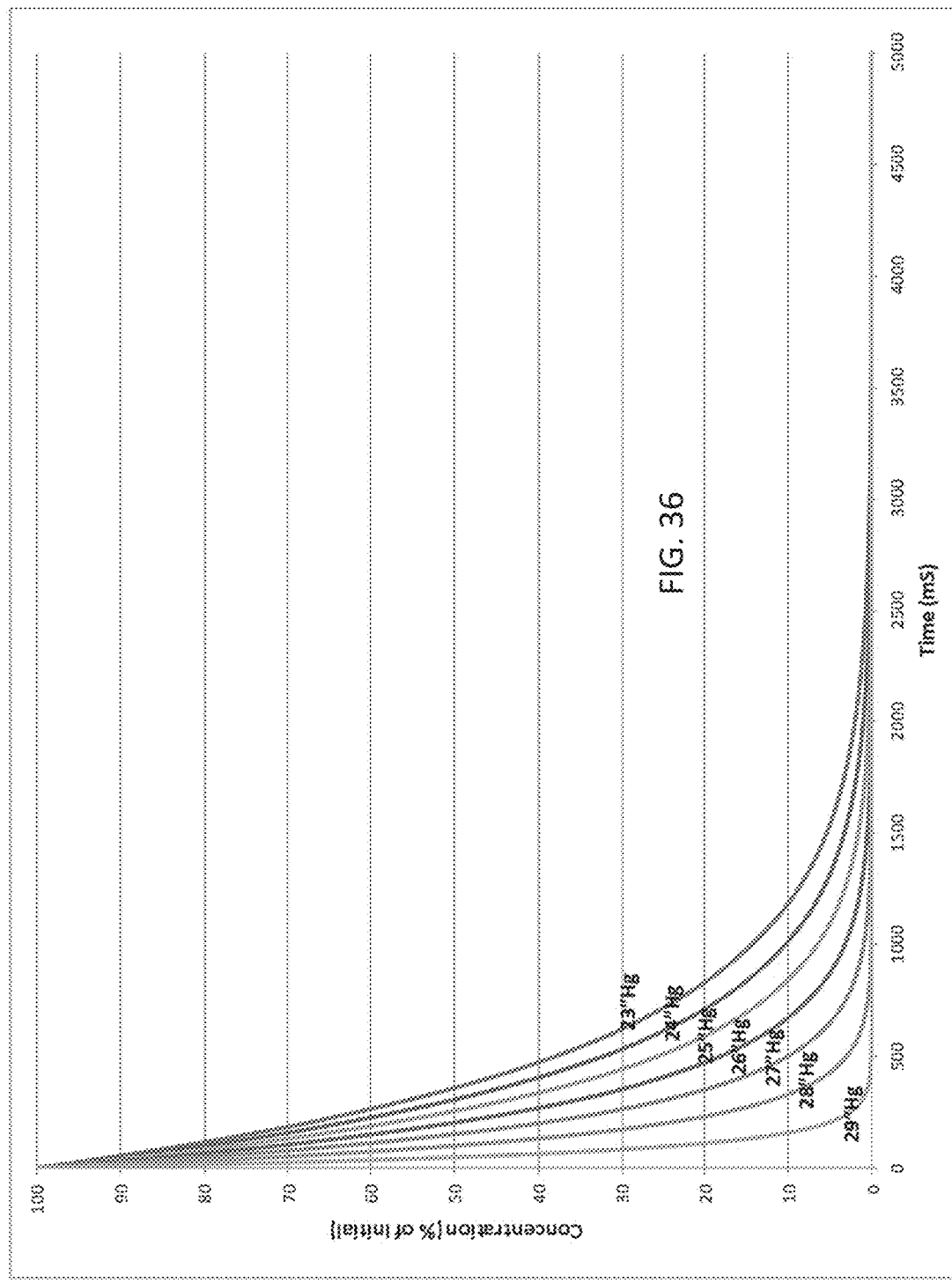
FIG. 36 shows the wash-out curves for a 30 microliter flow cell, in accordance with certain examples.
Figure 37:
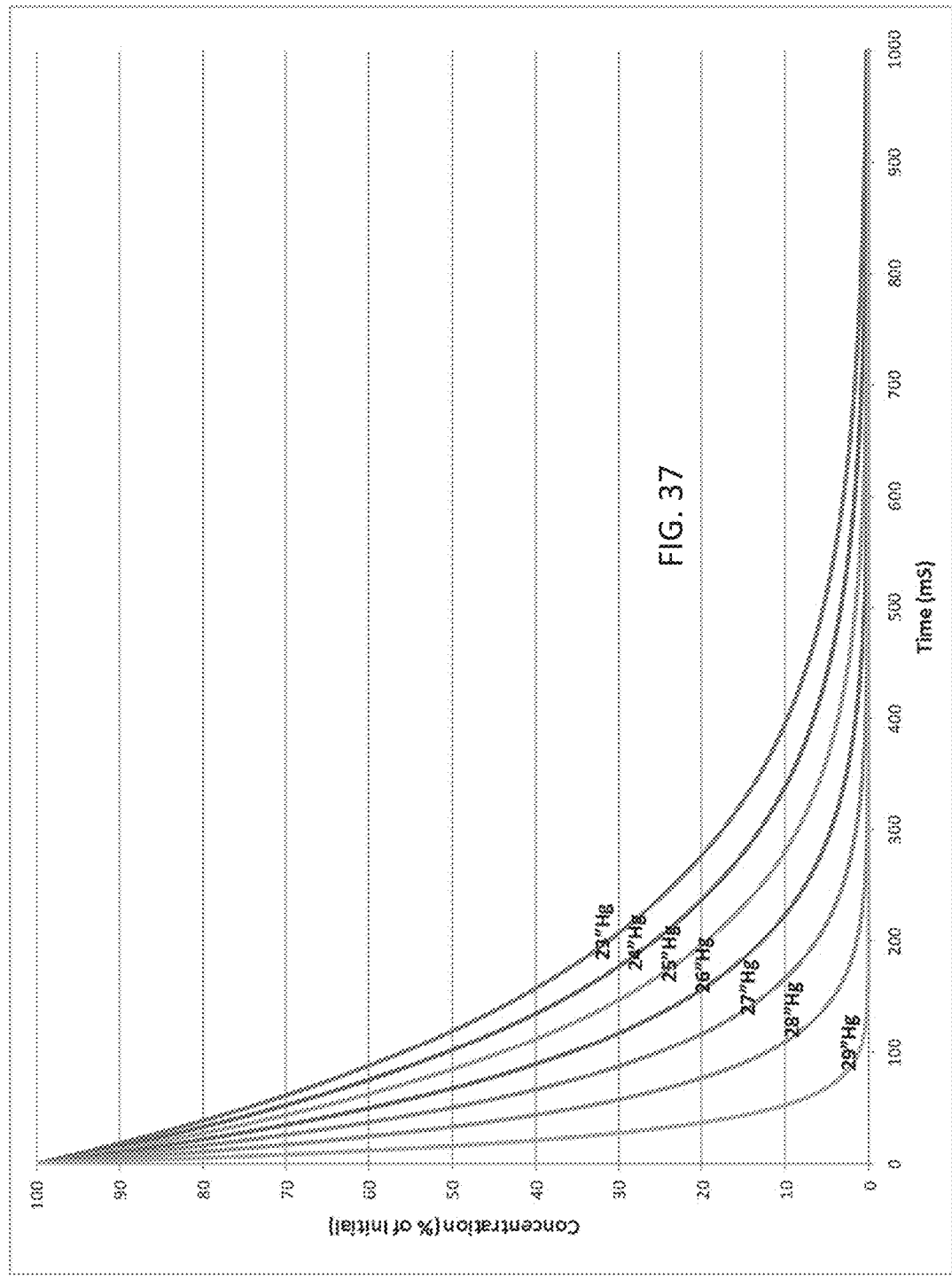
FIG. 37 shows the wash-out curves with a smaller cell (20 microliters), in accordance with certain examples.

A vacuum can be applied to a flow cell to increase the rate of sample flow into the flow cell. FIG. 36 shows the wash-out curves at a carrier gas flow rate of 1 mL/min with the detector cell (30 microliter volume) under a range of vacuum pressures. For comparison, the wash-out curves with a smaller cell (20 microliters) is shown in FIG. 37.

Figure 38:
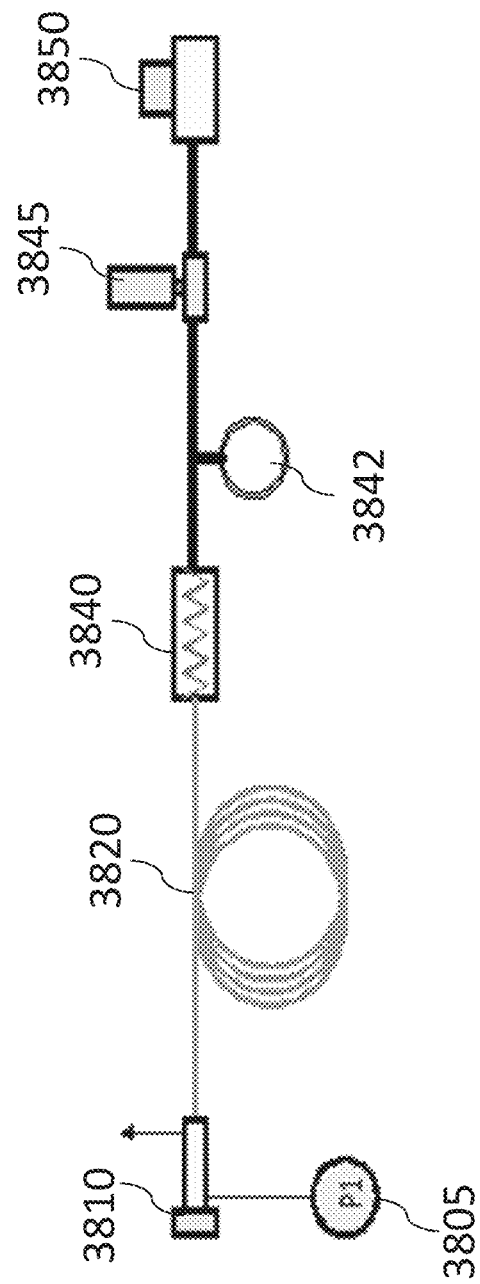
FIG. 38 is an illustration of a system for providing a vacuum to a flow cell of a detector, in accordance with certain examples.

A system was set up as shown in FIG. 38. The system included a PPC controller 3805 fluidically coupled to a split injector 3810. The injector 3810 was coupled to a column 3820, which was fluidically coupled to a detector 3840 operated under vacuum. An Edwards RV3 2-stage rotary vane vacuum pump 3450 was used. A needle valve 3845 was connected inline between the vacuum pump 3850 and the cell outlet of the detector 3840 to allow control of the cell pressure. A pressure sensor 3842 was placed in-line to monitor pressures. The improvement in peak shape with increasing vacuum is quite apparent as shown in the chromatogram overlay in FIG. 39. As pressure is decreased (higher vacuum), the peaks become sharper and narrower.

Example 4

Figure 40A:
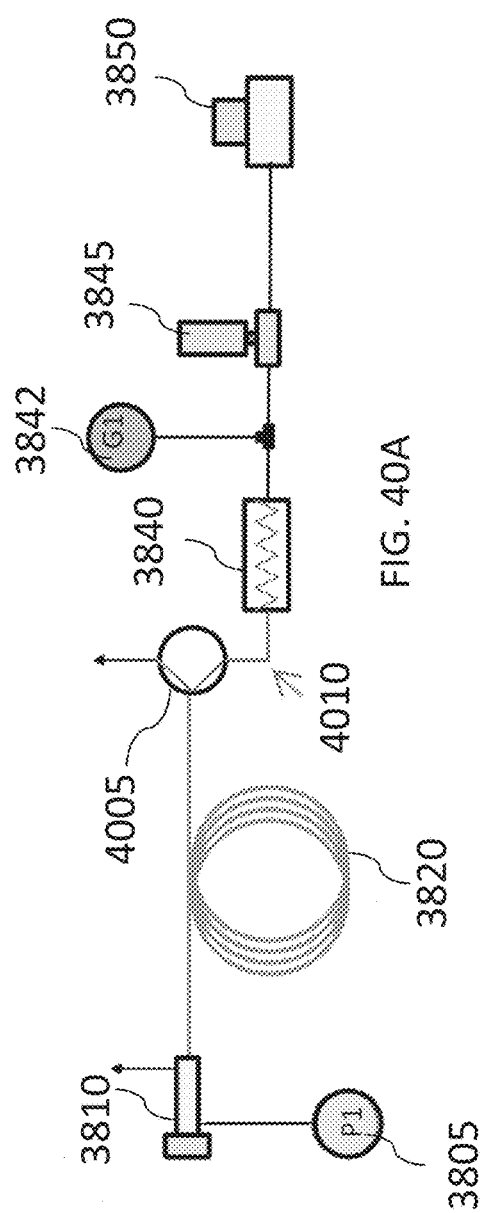
FIGS. 40A and 40B are illustrations of open split systems, in accordance with certain examples.
Figure 40B:
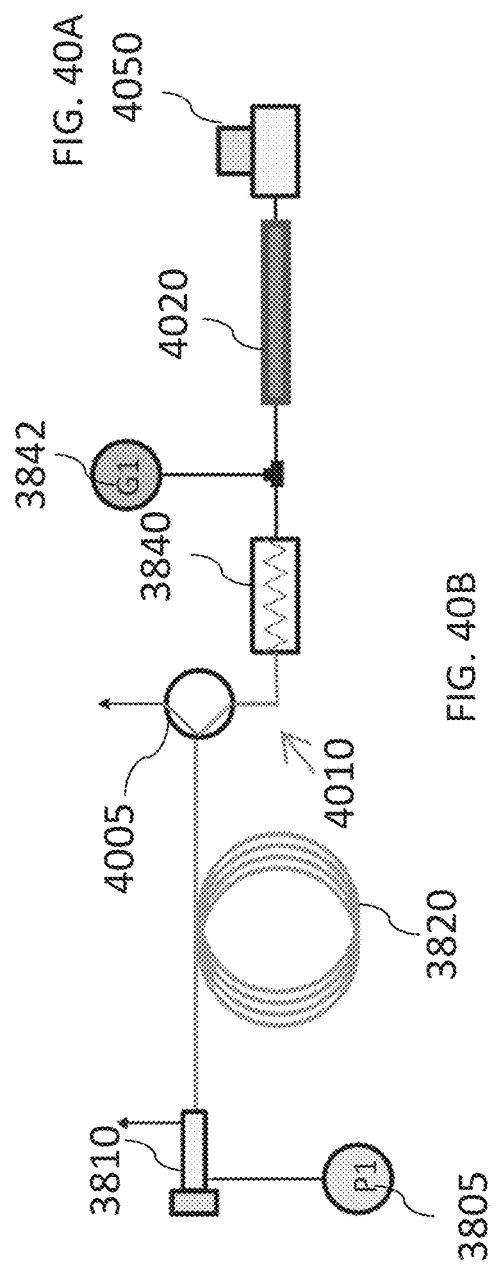
Figure 41:
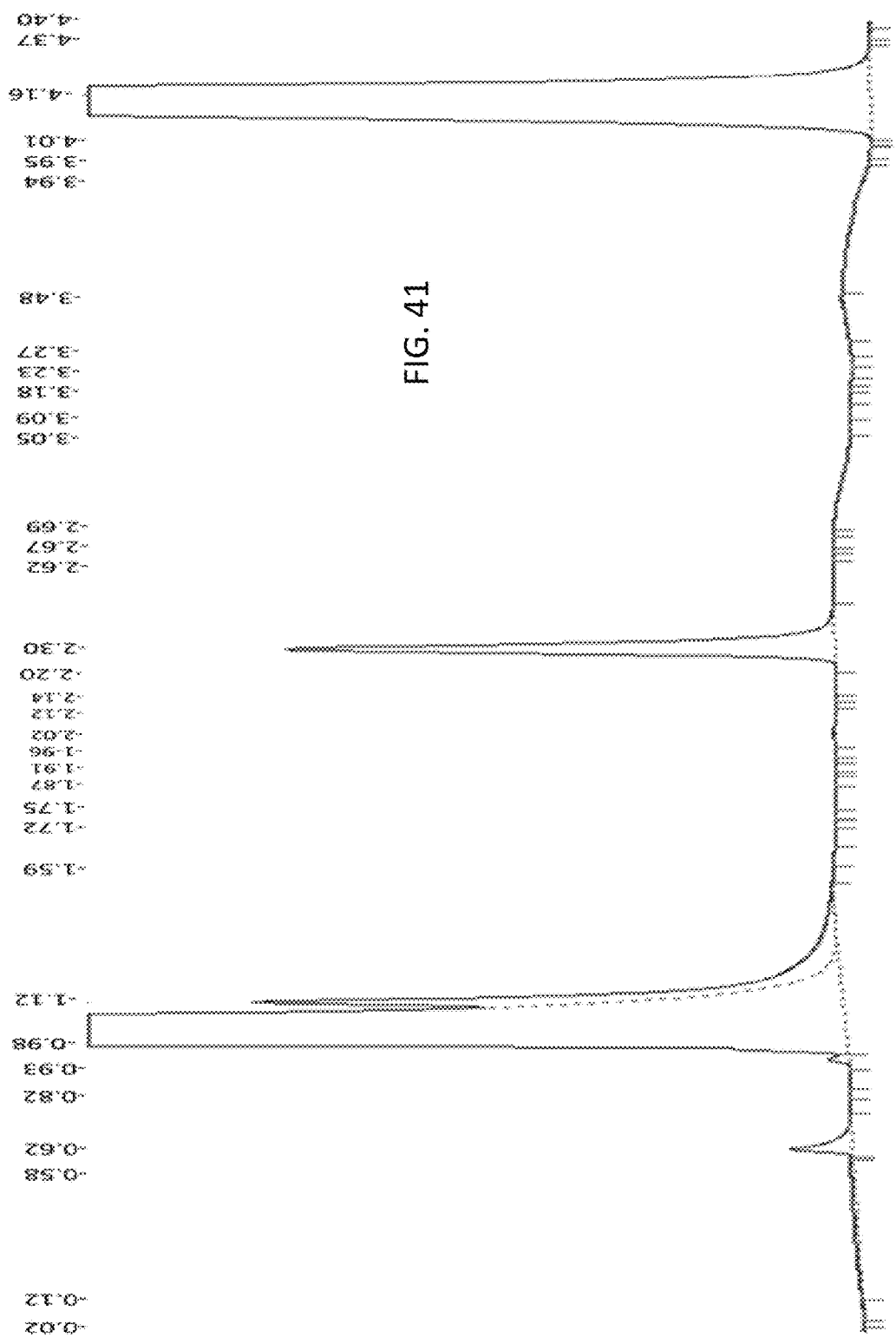
FIG. 41 is a chromatogram obtained using the system of FIG. 40B, in accordance with certain examples.

To control the sample and carrier flow through the cell/vacuum pump, an open split type interface consisting of a SilFlo 3 port splitter with a 75 um id restrictor can be added to the system shown in FIG. 38. For example and referring to FIGS. 40A and 40B, an open interface 4005 can be implemented between the column 3820 and the TCD inlet. In FIG. 40A, an adjustable restrictor 3845 was present, and in the system of FIG. 40B a buffer volume 4020 was placed between the detector 3840 and the vacuum pump 3850. The vacuum pump 3850, which was a rotary vane pump, was replaced with a diaphragm vacuum pump. In order to minimize possible pressure fluctuations from the diaphragm operation and reduce the flow restriction (maximize pump efficiency), the adjustable restrictor 345 was replaced with a buffer volume 4020 placed between the detector and the vacuum pump. A restrictor 4010 was added between the open interface and the detector 3840. FIG. 41 shows a chromatogram obtained using the system of FIG. 40B.

Example 5

Figure 42:
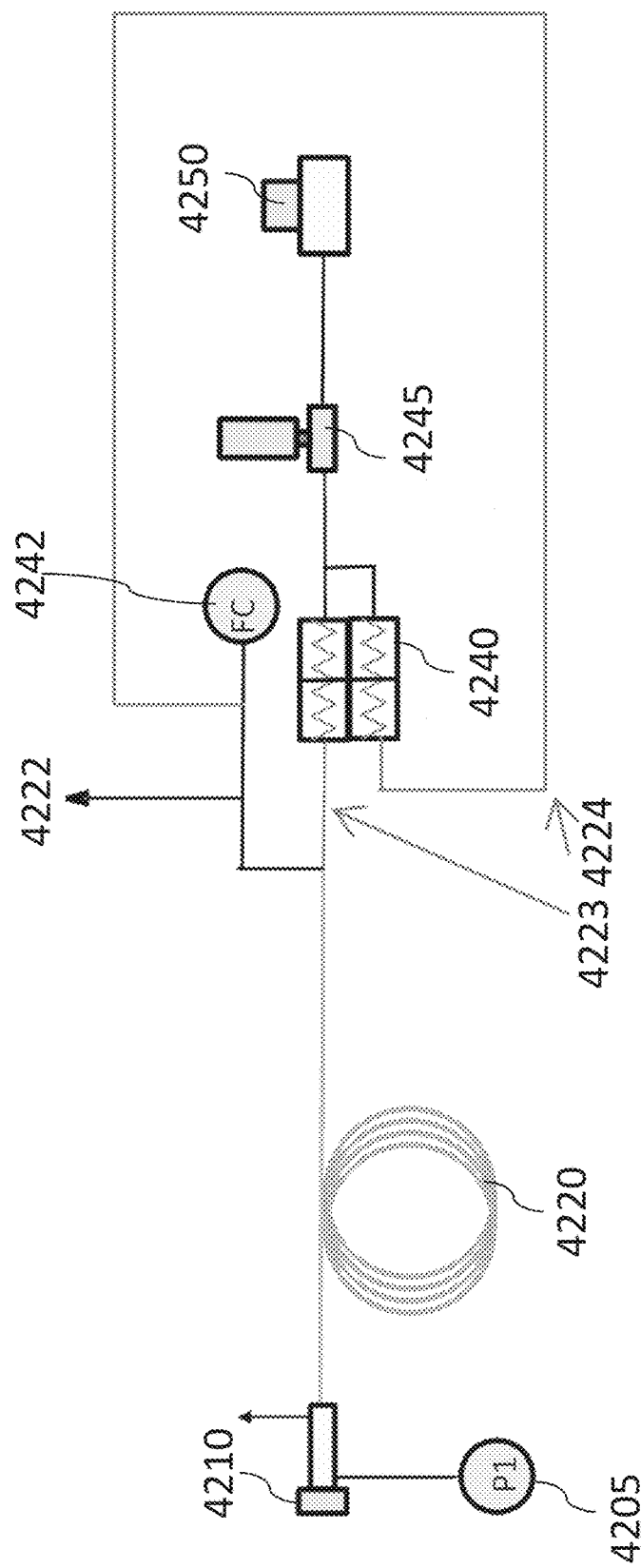
FIG. 42 is an illustration of another open split system, in accordance with certain examples.

An alternative configuration which reduces the potential number of gas sources utilizes a manual flow controller which can supply the needed gas for the reference side of the TCD using a fixed restrictor like the one used in the open split interface as well as the gas needed for the open split interface. This configuration also provides any makeup gas to the carrier side of the detector for use with carrier flow rates below the restrictor controlled flow through the detector. This configuration is illustrated in FIG. 42. The system includes an injector 4210 fluidically coupled to a PPC controller 4205. The injector 4210 is fluidically coupled to a column 4220. The column 4220 is fluidically coupled to a TCD detector 4240 through a restrictor 4223. The system can be vented through a vent 4222, if desired. The detector 4240 is also fluidically coupled to a flow controller 4242 through a restrictor 4224. The detector 4240 is fluidically coupled to a vacuum device 4250 (diaphragm pump) through an adjustable restrictor 4245. The use of fixed restrictors for detector inlet flow control will permit the use of a simple 'fixed flow' flow controller to provide a constant vent flow slightly above the total flow needed for the makeup and reference flows. The adjustable restrictor 4245 is used to provide the pressure supplied by the diaphragm pump 4250.

To determine the relative performance of the modifications to a standard detector configuration, a series of analyses of a PKI Detector Test Mix (PN N9307036) diluted 1:100 with hexane. The analyses were then evaluated using TotalChrom System Suitability software. The results were:

Dilution 1 (1:100): 18.5:1; Detection Limit: 7.6E-11 ng

Another set of the same sample was analyzed using the detector without the sub-ambient pressure conditions. The same column flow setting was maintained and makeup gas was added to provide the minimum recommended detector flow of 5 ml/min. These analyses were then evaluated and showed a significantly lower signal-to-noise ratio.
Reference (no vacuum, carrier+mu=5 ml/min) 2.5:1; Detection Limit: 5.6E-10 (Dilution 1)

To verify the sample used (and resulting detection limits), a second 1:100 dilution was made and analyzed.
Dilution 2 (1:100) S:N 21.1:1; Detection Limit:6.7E-11. A chromatogram of dilution 2 is shown in FIG. 43.

Example 6

FIG. 44 shows a simple configuration in which a column is connected to a traditional 2 or 4 cell (2 cell shown) detector which is held under vacuum. An optional vacuum device 4450 can be used to sustain sufficient vacuum at the low flow rates expected. One of the concerns in using such a configuration is that the flow rate through a column connected to that detector nay be affected by the vacuum. The performance of the vacuum pump 4450 will also be affected by the flow rate of carrier gas eluting from the column which in turn will again affect the column flow rate. To balance the detector cell 4442, the gas flow rate through the reference cell 4444 can be selected to match that through the analytical cell 4442.

The setup of FIG. 44 can be used to accurately track the narrow train of pulses produced by a pneumatic modulator for the multiplexing. The system includes a column carrier gas source 44025 fluidically coupled to an injector 4410, a column 4415 and the analytical cell 4442. A make-up gas source 4420 is fluidically coupled the reference cell 4444. To preserve peak fidelity, these pulse widths can be 100 mS or faster. The total volume of the TCD can be selected to provide desirable results. In addition, make-up gas can also be used.

Example 7

An alternative approach along the lines of a classic open-split interface was explored. FIG. 45 shows the general approach. This new configuration has the same components as shown in FIG. 44 but with some additional plumbing between the column and the detector. In particular, the system of FIG. 45 can include a carrier gas source 4505 fluidically coupled to an injector 4510, a column 4515, a vent 4530 and an analytical filament 4542. A make-up gas 4520 is fluidically coupled to a reference filament 4544 and to the vent 4530. An optional vacuum device 4550 can be fluidically coupled to the filaments 4542, 4544.

The vent was a piece of tubing with the exit end exposed to the atmosphere. The pressure drop across this tubing was very low so, essentially, the column exit is at atmospheric pressure. Gas flow rate into both the analytical and reference cells is controlled by a pair of matched restrictors with one restrictor upstream of the cells 4542, 4544. The inlet end of both restrictors will be very close to atmospheric pressure and the same as the column outlet pressure. The outlet of the restrictors will be connected to the two TCD cells 4542, 4544 which can be under the vacuum delivered by the miniature vacuum pump 4550. These restrictors can be fabricated from lengths of narrow-bore capillary tubing. If the geometries of the restrictors are closely matched, then the flow rates into both cells 4542, 4544 should be the same. If the restrictors are held in a thermostatted environment, then these flow rates should remain constant. Using this configuration, the flow rate of carrier gas through the column 4515 and into the detector will now be completely independent. The flow rate into both cells should be unaffected by temperature programming—a significant benefit. Further, maintaining a constant flow through the detector can also minimize baseline fluctuations contributed by column flow upsets due to valving and microfluidic switching (backflush to detector/series bypass, column selection and others). It can also be useful for column pressure, flow or velocity programming.

In FIG. 45, the reference gas (labeled P2) 4520 not only feeds the reference cell but also keeps air completely out of the system that would otherwise be pulled in through the vent.

Example 8

In FIG. 45, the reference gas (labeled P2) not only feeds the reference cell but also keeps air completely out of the system that would otherwise be pulled in through the vent. It also acts as a make-up gas when a column with a low flow rate is being used. The principle is illustrated further in FIGS. 46 and 47, which show the gas flows through the system.

Referring to FIG. 46, the system can include a carrier gas source 4605 fluidically coupled to an injector 4610, a column 4615, a vent 4630 and an analytical filament 4642. A make-up gas 4620 is fluidically coupled to a reference filament 4644 and to the vent 4630. An optional vacuum device 4650 can be fluidically coupled to the filaments 4642, 4644. The detector response may be compromised because some of the sample stream from the column is vented and does not enter the detector. For some detectors (for instance a flame ionization detector) this can be a concern. In the case of a TCD, the response is a function of analyte concentration and venting some of the sample stream does not substantially affect its concentration. Thus, venting where a TCD is used should not affect detector response. For example, even in situations where 90% of the sample stream is vented, the detector response is largely unaffected. This behavior makes it easy to optimize the TCD design for high-resolution capillary columns but still retain full compatibility with packed columns. Further, in such instances, the vent may be connected to another detector (for instance an FID) to collect data from two detectors simultaneously.

Referring to FIG. 47, the reference gas is now shown as mixing with the column effluent, which will provide a dilution effect that would degrade the detector response. This effect can be mitigated by judicious choice of the restrictors to provide the lowest flow rate possible. There can be a limit to the minimum flow rate into the detector because, even with vacuum, peak tailing and dispersion will start to occur at some point. For example, restrictors can be chosen to support 0.25 mm i.d. columns that provide ~1 mL/min with helium and nitrogen and ~2 mL/min with hydrogen. Narrower columns will experience a small amount of make-up gas—but this will already be much lower than with earlier TCD designs so there will still be a performance advantage.

Referring to FIG. 48, the carrier gas flow rate through the column 4615 is greater than that entering the detector 4642, 4644 through the restrictors. The excess column effluent exits via the vent 4630 to a second detector 3810.

Example 9—TCD Design

This approach described herein for a TCD works well with a conventional 4-cell bridged configuration. The 69.5 µL cell as used on the current Clarus GCs still shows some evidence of peak tailing when used to monitor peaks 1 or 2 seconds wide. A 20 µL cell TCD shows much improved performance. 10 µL and 5 µL cell detectors (as described in the Examples below) may mitigate the need for such a high vacuum and may even enable the use of the modulator for a single cell design.

Example 10—Pump Design

Initial work on vacuum operation used an Edwards RV3 roughing pump normally used with the Clarus quadrupole MS systems. This gave excellent performance for this application—a very stable and strong vacuum (less than 29 inches of mercury) when used to draw 2 mL/min (STP) of hydrogen gas.

With 20 µL TCD cells, good performance with 0.25 mm i.d. capillary columns was observed with a vacuum of 25 inches of mercury. The vacuum was adjusted by an in-line needle valve between the pump and the detector cells.

If desired a pump with speed control features may also be used. For example, the degree of vacuum inside the TCD cells, upstream of the pump, can be monitored using a differential pressure transducer. The output of such a transducer could potentially control the pump speed so regulate the vacuum to a defined set-point. This should help give better stability and consistent performance of the pump as it ages or is exchanged or when two different systems are compared. FIG. 49 shows an illustrative system. The system includes a carrier gas source 4905 fluidically coupled to an injector 4910, a column 4915, a vent 4930 and an analytical filament 4942. A make-up gas 4920 is fluidically coupled to a reference filament 4944 and to the vent 4930. An optional vacuum device 4950 can be fluidically coupled to the filaments 4942, 4944. A transducer 4960 and controller 4965 can be used to assist in controlling glow into the filaments 4942, 4944.

Example 11—Manifold Design

Figure 50:
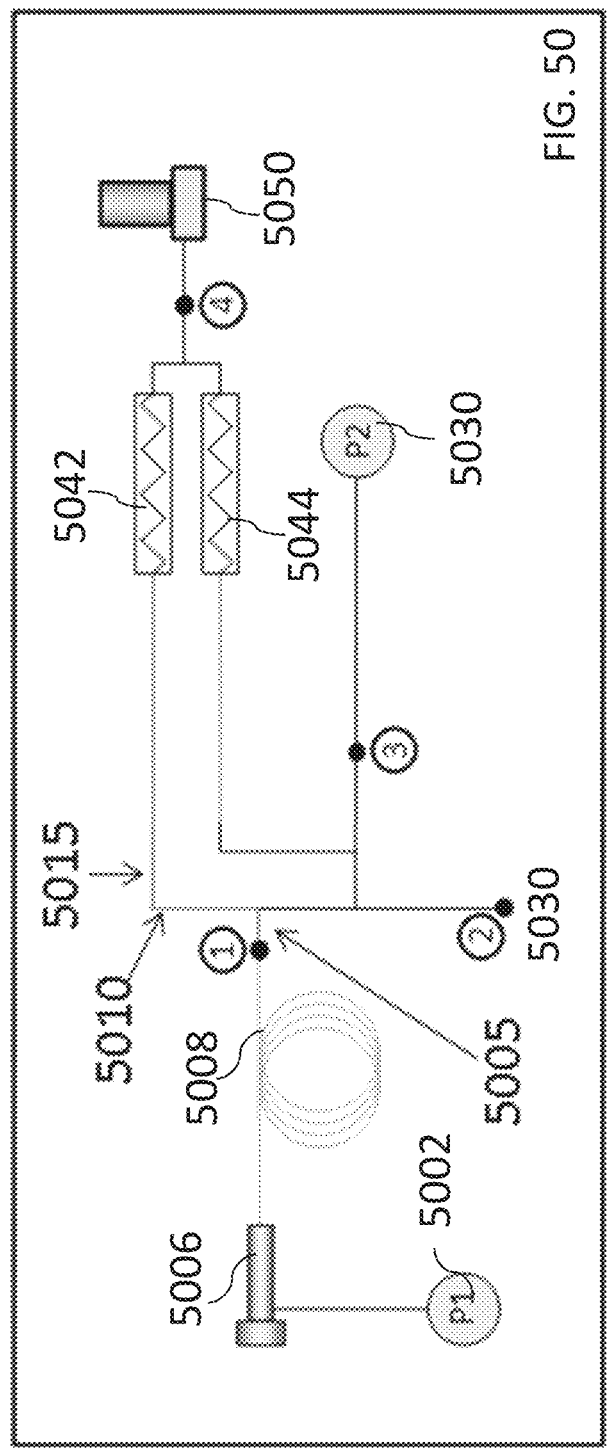
FIG. 50 is a diagram of an interface for a vacuum-operated TCD with ports indicated, in accordance with certain examples.

A micro-fluidic manifold can be used to interface the column to the detector. The manifold and restrictors can be fully integrated into the detector heated environment and attached to the cell block directly, if desired. In one design, there can be 4 external ports provided in the final design—these are labeled 1 to 4 in FIG. 50.

Port 1 is the column connection. This port is desirably accessible from inside the GC oven where the column 5008 will be mounted. The connector can be optimized for capillary columns and can be of low thermal mass. An adapter may be used to provide connections to both packed and micro-packed columns. This connector can be heated by the column oven and can be designed to not leak or allow air to ingress even when at the oven maximum temperature (450° C.). The column 5008 is fluidically coupled to a carrier gas source 5004 and an injector 5006.

Port 2 (reference 5030) is for venting excess gas. This port is desirably accessible to the user to check flow rates etc. It can also provide the sample flow stream to another detector, so it can be located inside the GC column oven—adjacent to Port 1, if desired. Some form of union can be used to either attach a barbed fitting for flow measurements or a connecting tube to another detector. The union can be exposed to the column oven side of the detector so that there are no cold spots. A tube can be connected to it leading to the outside of the oven for flow measurements and so that if hydrogen carrier gas is being used, it will not be vented inside the GC oven. It is exposed to ambient air and the inner diameter should be such that the venting gas velocity should be greater than air diffusion. The inner diameter is desirably not so narrow that a significant pressure drop is observed across it.

Port 3 is the connection to the reference/purge/make-up gas supply 5020. This may be just a simple union. It does not have to be heated but desirably does not leak or allow air ingress and is desirably readily accessible from the outside of the detector assembly.

Port 4 is the connection to an optional vacuum pump 5050. This port desirably can be accessed by the user in the event of pump failure and subsequent replacement. This connector is downstream of the detector and can sustain a vacuum. It is not heated and if there is slight outgassing from O-rings etc., this should not be a concern.

In one design, the manifold internal microchannels can be 0.3 to 0.5 mm in width. The exception being the sections immediately downstream of port 1 and pointed to by arrows 5005, 5010 and 5015. These sections 5005, 5010 and 5015 carry the sample to the detector cells 5042, 5044. They are not under vacuum and the flow rate will be low (1 to 2 mL/min), and so they are desirably sufficiently narrow (e.g. 0.25 mm or less) so that there is no dispersion or tailing induced as the sample vapor passes through them. The sections 5005, 5010 and 5015 also are desirably chemically inert (as is the restrictor feeding the analytical channel). Some form of silane deactivation can be used, e.g., a SilcoNert® 2000 coating from SilcoTek. Minimizing the length of these channels can also help reduce the risk of analyte breakdown or adsorption.

Example 12—Restrictor Design

In certain instances, there are two restrictors that feed the analytical and the reference cells, e.g., a restrictor is positioned between the column and the analytical cell and a restrictor is positioned between the make-up gas and the reference cell. They can be matched in impedance. Because impedance is highly dependent on temperature, the two restrictors are desirably located in the same thermal environment or even in the same thermostatted environment.

Figure 51:
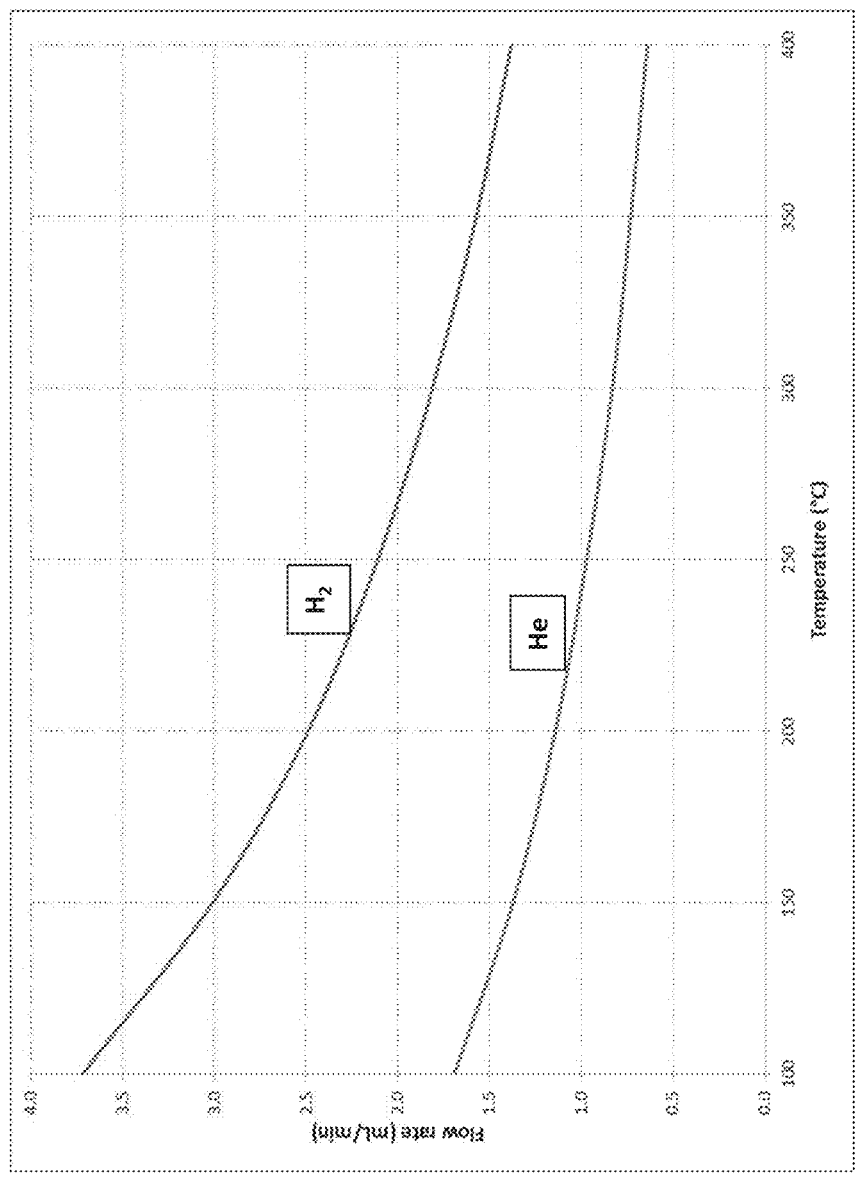
FIG. 51 is a graph of gas flow rates through a restrictor over a range of applied temperatures, in accordance with certain examples.

In one design, lengths of capillary tubing are used as restrictors. These can be brazed or soldered to the manifold and other components to aid assembly and replacement and help avoid issues with leaks and general reliability. There is a variety of commercially available stainless steel capillary tubing. A suggested geometry would be 150 mm long with a 0.10 mm internal diameter. Such restrictors should provide the flow rates plotted in FIG. 51 for different gases hydrogen and helium. Note that although these flow rates do vary significantly with temperature, they should remain matched between the analytical and reference restrictors and cells so the detector baseline should remain balanced. Also, the detector signal should be unaffected by the amount of sample vapor entering it. Finally as the temperature increases and the flow rate at STP (proportional to the mass flow rate), the volumetric flow rate will be increased by the temperature and so the two-effects will self-compensate to some degree.

Because the analytical restrictor carries the sample stream, the internal wall may be deactivated to make it inert to reactive or adsorptive compounds. The SilcoNert® 2000 coating mentioned earlier can be used for deactivation.

Example 13—Pneumatic Design

With this design approach, the column outlet (at the Port 1 connection in FIG. 50) is very close to atmospheric pressure even through the detector is not at atmospheric pressure. This means that the flow rate through the column is controlled by the inlet pressure, P1, in the same way as for conventional detectors. The same methods should apply without constraint. Thus any injector type should also be supported: split, splitless, packed, GSV, LSV, HS, ATD, etc. The vacuum will draw a low fixed flow through the restrictors. Any excess flow from the column will be vented.

An independent gas supply can feed the reference cell and this is provided by the P2 controller shown in the various figures. The flow rate of the gas into the reference cell can be precisely controlled. As with the sample flow, this control is achieved by the vacuum across a fixed restrictor feeding the detector cell. Because both the sample and reference cells are using the same vacuum, any variations in that vacuum should self-compensate.

Figure 52:
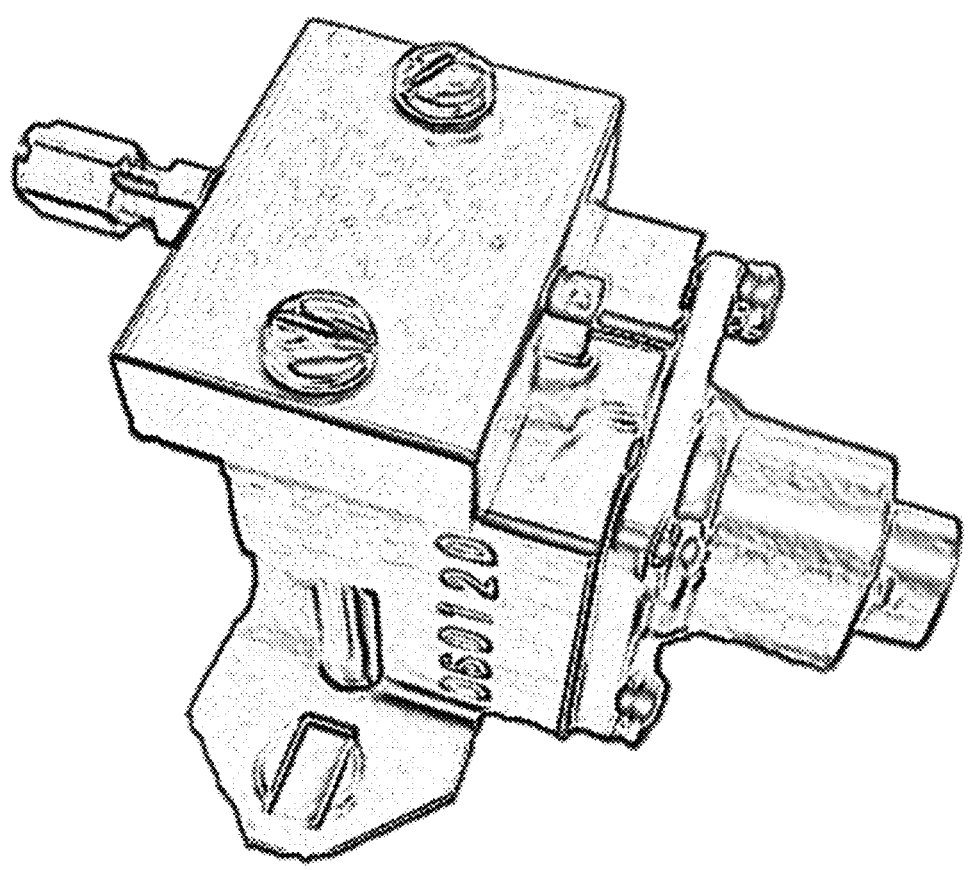
FIG. 52 is a line drawing produced from a photograph of a flow controller which can be used for P1 (or the other supplies), in accordance with certain examples.

Because the flow rate of reference gas is not dependent on the performance of the P1 controller, a simpler, lower cost device may be used for this purpose. The pressure of the supplied reference gas is very close to ambient pressure so a fixed pressure regulator with a fixed downstream frit can be sufficient to deliver a fixed flow rate of 5 to 10 mL/min. These devices are already used on the Clarus GCs for septum purge and PPC vent controllers. An example is shown in the line drawing produced from a photograph that is shown in FIG. 52.

Example 14—Safety Interlocks

Like all TCDs, the filaments should not be heated in the absence of carrier gas to prevent overheating and/or oxidation from air ingress. On existing Clarus TCDs, the detector is 'linked' (by the user) with a controller used to supply carrier gas to the GC column. If that supply is interrupted, the TCD filaments will be automatically turned off. Thus the safety of the TCD is dependent on a device external to the detector and relies on the user to correctly configure the system. With this new approach, the filaments can be turned off if the vacuum fails or if the reference gas supply fails.

Example 15—Temperature Control

The TCD signal is derived from the thermal flux from heated filaments to a surrounding metal block. The signal is highly dependent on not only the control of the filament temperature but also on the temperature of this metal cell block. On the Clarus TCD, the cell block is not heated directly but draws its heat by radiation or convection from a surrounding heated chamber. The cell block is suspended inside this heated chamber by the metal inlet and outlet tubing. The chamber is externally lined with insulation and is held inside a thin metal case.

Figure 53:
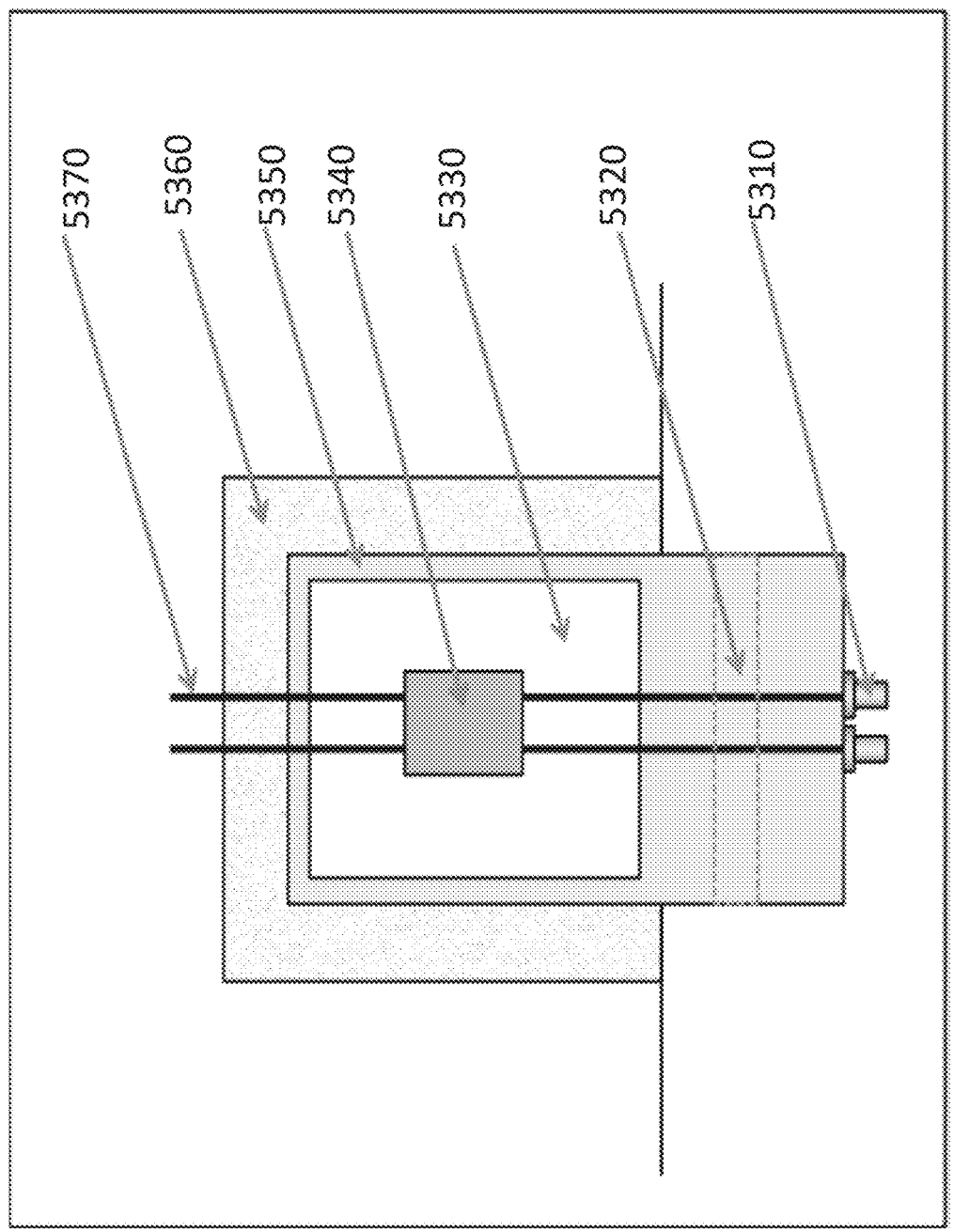
FIG. 53 is a diagram of a cell block heating arrangement, in accordance with certain examples.

FIG. 53 is a diagram of a TCD heating arrangement. The diagram includes column ports 5310, a cartridge heater 5320, an air gap 5330, a filament cell block 5340, a heated chamber 5350, insulation 5360 and exit vents 5370. This configuration uses the resultant air-gap 5330 between the cell block 5340 and chamber 5350 as a thermal buffer to minimize baseline artifacts resulting from ambient temperature changes. It also means that it may take many hours to finally thermally equilibrate. A reduction in the thermal equilibration time is achieved using the newer design described herein. The new TCD can be heated in the same way as the Clarus TCD so that the full benefits of the thermal isolation from the environment are fully realized. To reduce the thermal equilibration time, a small heater be mounted directly onto the cell block 5340. This 'roughing' heater would quickly heat the cell block 5340 to a temperature close to the set temperature and then it would be turned off and leave the temperature to stabilize from radiation and convection from the heated chamber.

Example 16—Electronics

The detector signal will be derived in a similar way to the current Clarus TCD. Because faster chromatography will be supported, the filtering time constants may need to be reduced. This may result in higher noise levels and so some consideration should be given to reduce this noise electronically. The current Clarus TCD supports a data collection rate of up to 50 Hz (on the 680), but with the new design the data collection rate can be increased to at least 100 Hz.

Example 17—Dual Channel Designs

Figure 54:
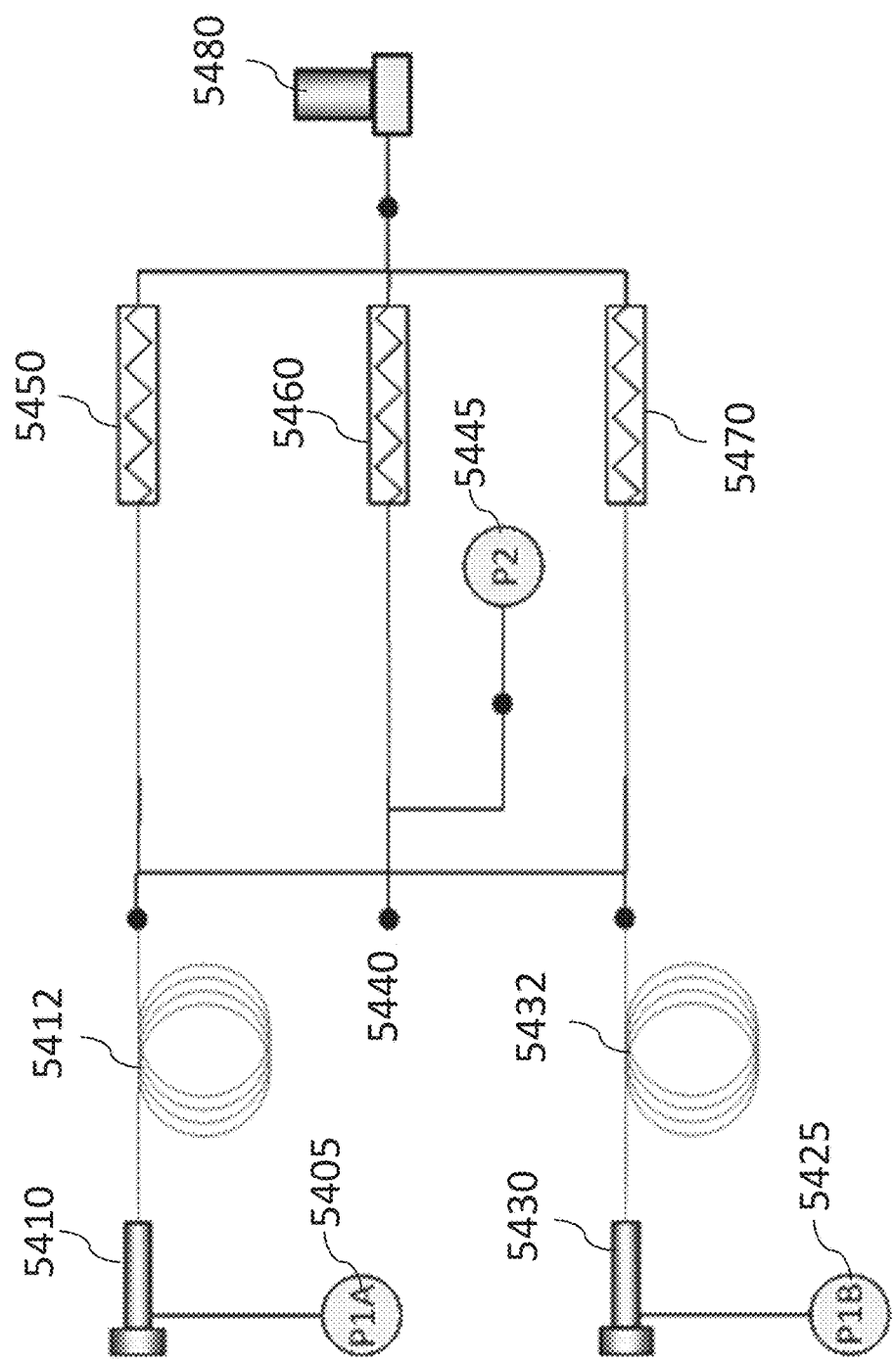
FIG. 54 is a diagram of a dual-column TCD configuration, in accordance with certain examples.

For dual column operation, rather than configure two independent detectors on the GC, it is possible to add a third channel of filaments and cells into a single block and manifold as shown in FIG. 54. Such an implementation only uses an optional single vacuum pump and a single reference/make-up gas supply. The system includes a first carrier gas source 5405 fluidically coupled to a first injector 5410 and a first column 5412. A second carrier gas source 5425 is fluidically coupled to a second injector 5430 and a second column 5432. The column 5412 is fluidically coupled to a first filament detector 5450, and the column 5432 is fluidically coupled to a second filament detector 5470. A reference filament detector 5460 is fluidically coupled to a reference gas 5445 and to a vent 5440. An optional vacuum device 5480 is fluidically coupled to the detectors 5450, 5460 and 5470. If desired, the vacuum device 5480 can be omitted and replaced with a vent. Matched impedance restrictors can be placed between the column/detectors 5412/5550 and 5432/5470.

Example 18—Flow Modulation

Figure 55:
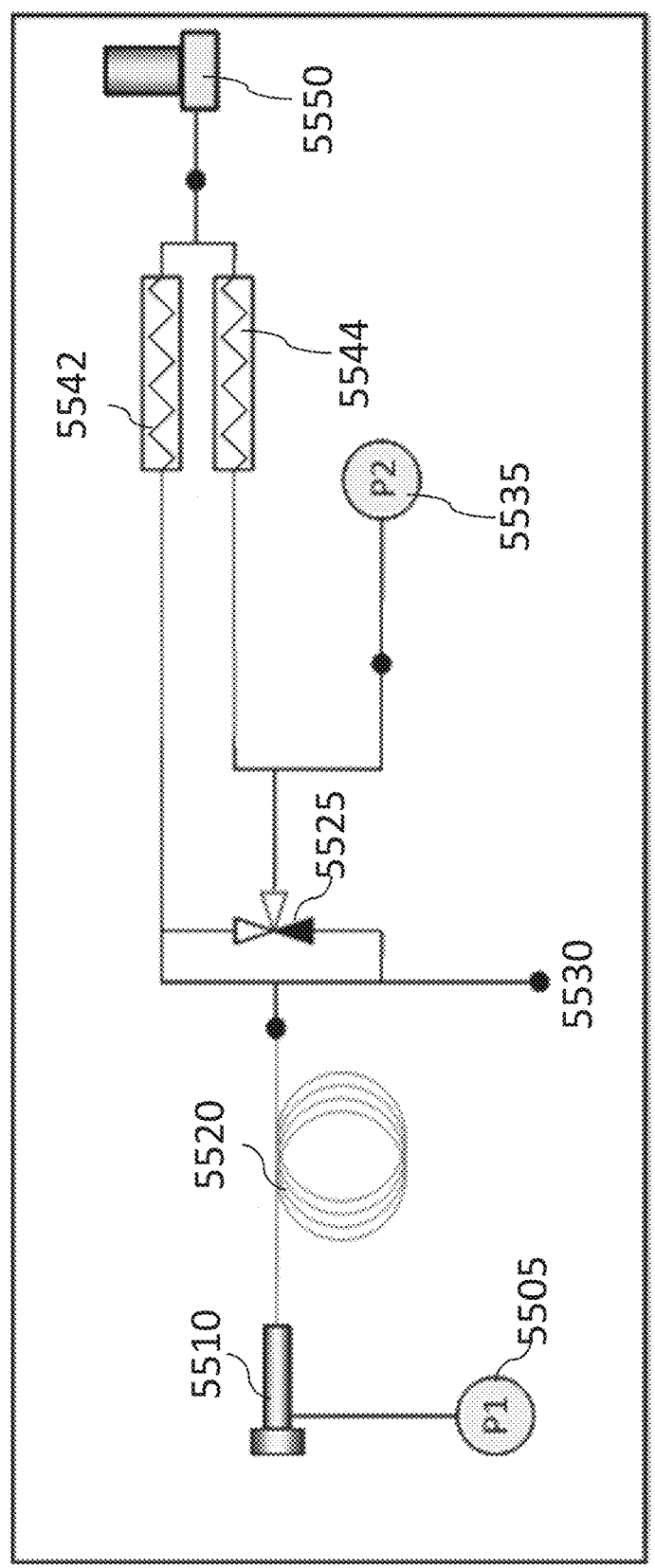
FIG. 55 is an illustration showing use of 3-way solenoid valve to affect modulation, in accordance with certain examples.

The availability of the 10 μL and 5 μL cells may make the modulation approach more appealing. FIG. 55 shows how the inclusion of a 3-way solenoid valve 5525 can provide the modulation function. In one position the solenoid valve 5525 directs the reference gas from a reference gas source 5535 to the vent 5530 and carrier gas from the carrier gas source 5505, injector 5510 and the column 5520 is able to enter the restrictor going into the TCD analytical channel 5542. With the solenoid valve 5525 switched to the other position, only reference gas from the reference gas source 5535 will enter the analytical cell 5542. The reference gas may also enter the reference channel 5544. An optional vacuum device 5550 can be present, or a vent may be present where the vacuum device 5550 is shown.

By applying a stream of electrical pulses to the solenoid valve 5525, the column effluent and the reference gas are alternately switched to the analytical channel filament. This can occur at least 5 Hz and preferably 10 Hz to be able to describe peaks that are ~1 second wide.

Example 19—Detector Specifications

The table below lists some illustrative TCD specifications that can be used.

TABLE 1

| Attribute | Specification |
| --- | --- |
| Detection limit | ≤400 pg/mL n-tridecane in hexane |
| Linear dynamic range | ≥$10^6$ |
| Baseline stability | TBD |
| Thermal equilibration | Baseline stability specification met within 30 minutes |
| Filament cell capacity | TBD |
| Carrier gas support | He, $H_2$, $N_2$, Ar |
| Flow rate through detector | Approximately 1 mL/min for He, 2 mL/min for $H_2$ |
| Column support | Any capillary column and 1/8 packed columns |
| Carrier gas flow rate | 0.2 to 20 mL/min |
| Reference gas flow rate | 5 mL/min He, 10 mL/min $H_2$ |
| Temperature range | 100 to 400° C. |
| Filament current | TBD |
| Minimum peak width without significant tailing | 1 second |
| Sample path | Deactivated with SilcoNert ® 2000 or equivalent |
| Data collection rate | ≥100 Hz |
| Size | TBD |
| Manufacturing cost | TBD |

Example 20

Figure 56:
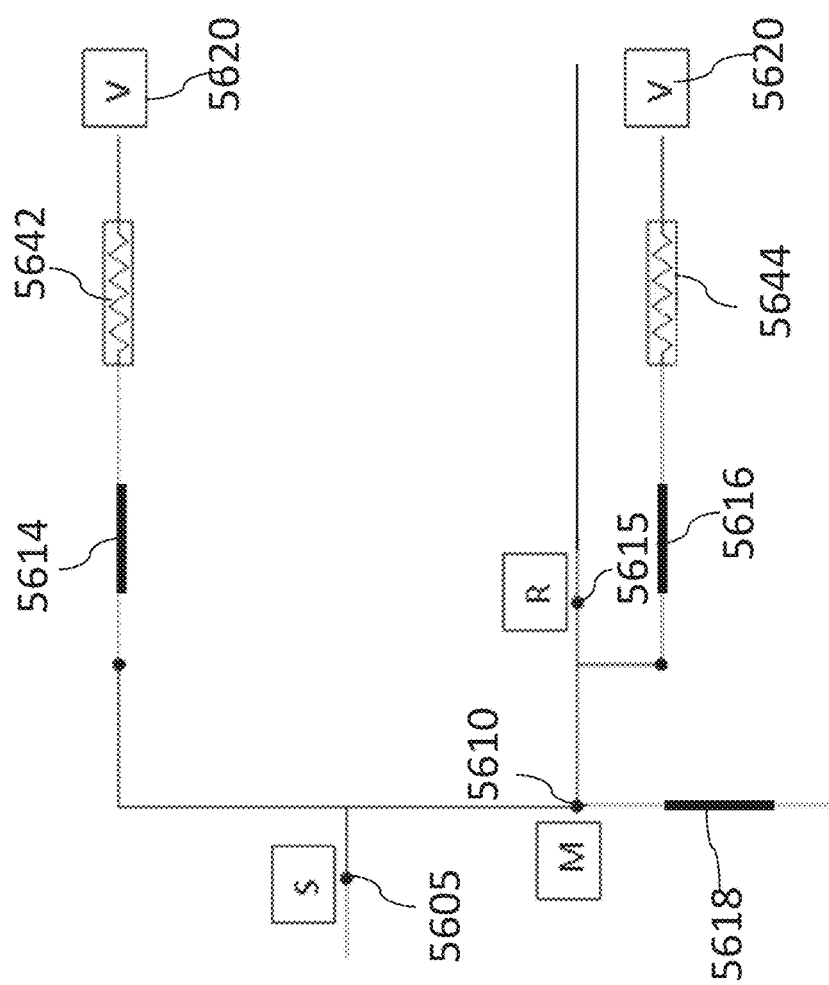
FIG. 56 is a schematic of a manifold that can be used to decouple column flow and detector flow, in accordance with certain examples.

A TCD with 10 microliter cells can include an integral manifold and restrictors as shown schematically in FIG. 56. The detector can be a drop-in replacement for the current Clarus 500 TCD and can be mounted and installed in the same way as the current detector. It can be mounted on a 110-volt Clarus 500 with a split/splitless injector and PPC. An autosampler will be available to perform sample injections. The standard TCD temperature control, amplifier and power supply will be used to test the new TCD. Reference/make-up gas can be provided to a port 5610. This port is located in the GC oven via a length (~20 cm) of 1/16" o.d. tubing, though this tubing can be moved externally if desired. The column connects to the manifold at port 5605 (Port S in FIG. 56) via a long (~20 cm) length of 1/16" o.d. tubing. A 0.25 mm i.d. column could be threaded through this tubing up into the heated cell box. The columns can be connected to the filament cells (analytical cell 5642 and reference cell 5644, respectively). The excess reference make-up gas is vented via port 5610 (Port M). In some configurations, this vent may need to be re-routed back into the GC oven for connection to a second detector. The effluent from both TCD cells are combined and vented via port 5620 (Port V). A first restrictor 5614 is present between the port 5605 and the analytical cell 5642, and a second restrictor 5616 is present between the reference make-up gas port 5615 and the reference cell 5644. An optional third restrictor 5618 may also be present to assist in controlling flow into the cells 5642, 5644.

Example 21

Figure 57:
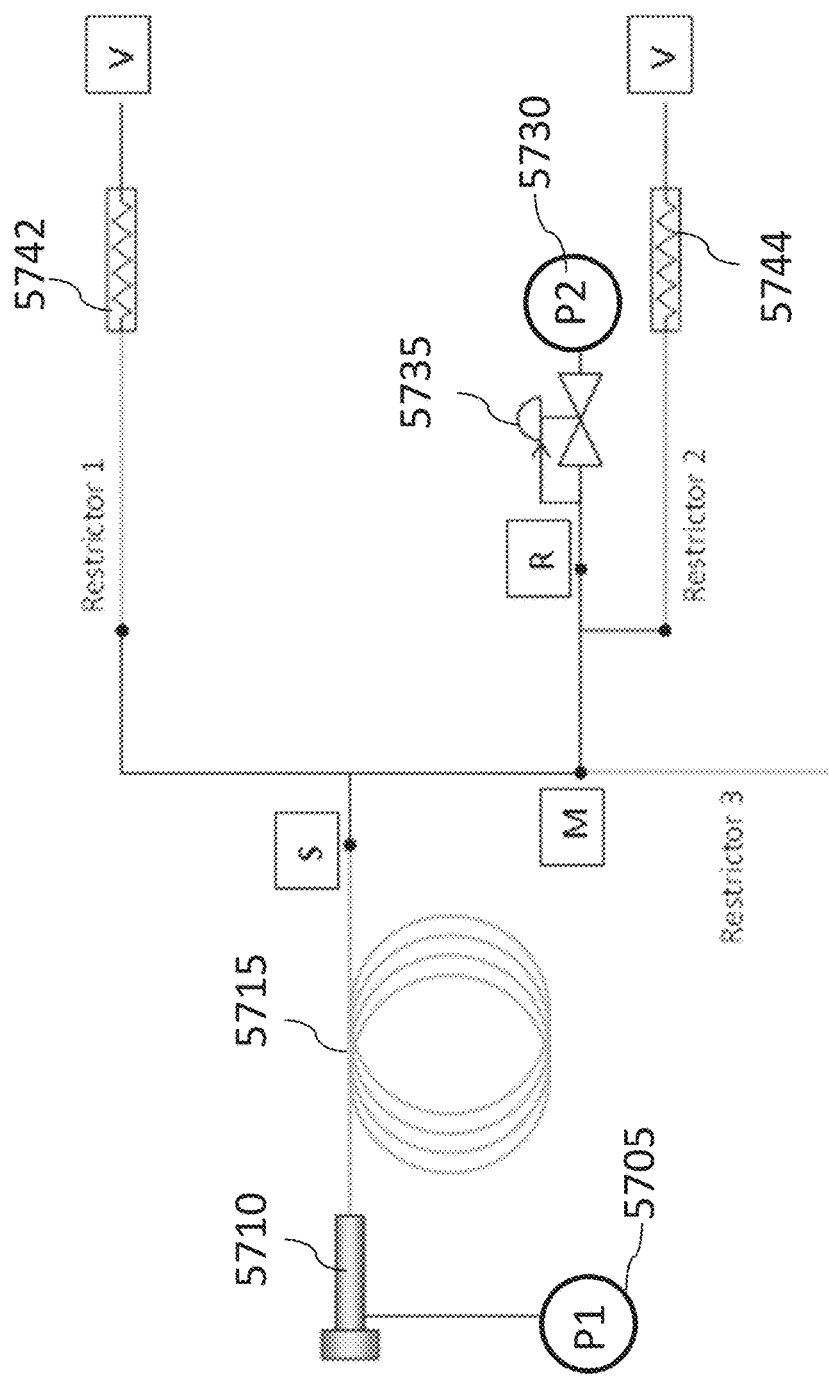
FIG. 57 is a schematic of a system that can include a 10 microliter TCD analytical cell and a 10 microliter TCD reference cell, in accordance with certain examples.

A system including a manifold based on the detector of Example 20 is shown schematically in FIG. 57. Port S is the sample inlet into the detector 5742 and is connected directly to the column 5715 and indirectly to the injector 5710 and carrier gas source 5705. A 25 cm length of 0.744 mm i.d. tubing represented an internal capacity of 109 μL. Port R is the reference/make-up gas input that is connected to a regulator 5735 and a gas source 5730. This will be supplied from an external mechanical pressure regulator 5735. Pressure inside the manifold can be constant/set at a set pressure using this regulator. This port is routed into the GC oven, though it can be positioned outside if desired. Port M is the vent for the manifold. The elution flow rate will be set by the reference/make-up supply regulator 5735 and Restrictor 3. This flow rate can be set to a fixed value sufficient to vent the maximum excess flow coming from the column that does not enter the analytical cell. To tolerate a packed column, this can be set, for example, to about 15 mL/min Restrictor 3 is not part of the detector and for evaluation, an external needle valve was connected to Port M. This provides additional scope for adjustment during evaluation. If desired, a fixed restrictor may be sufficient and this may be integrated into the cell block with Restrictors 1 and 2. Port V is a single port connected to the cell outlets. These outlets are connected together internally. If desired, separate outlets (as indicated in FIG. 57) for the analytical 5742 and reference 5744 cells can be used. While each of the detector cells 5742, 5744 is configured as a TCD cell, if desired the cells instead could be configured as flame ionization detectors or other filament based detectors.

Installation was straightforward on a 110-Volt Clarus 500 GC. Standard heaters for the Clarus TCD were inserted into the block of the new TCD and it was installed in the same way as a standard Clarus TCD using the same enclosure and insulation. The filament connector was the same as used for the Clarus TCD so it was just a case of plugging it into a standard Clarus TCD amplifier. The filament resistance was 23 ohms and so the values for the applied set currents can be adjusted to reflect the difference in resistance from the standard Clarus TCD cells. A Porter 0-60 psig regulator and gauge were connected to Port M. A 1/8" Swagelock union was used to make this connection inside the GC oven. This regulator was adjusted manually to get the required pressure inside the manifold. A 0.25 mm i.d. capillary column was connected to Port S by pushing it as far as it would go into the stainless steel tubing on this port. A 1/8" Swagelock union and graphite/Vespel ferrules were used to seal the connection. An external needle valve was connected to the stainless steel tubing connected to Port M. This was adjusted manually to get the required vent flow. Data collection and processing were performance using TotalChrom 6.3.2.

Example 22

The interface of Example 21 was tested under the conditions shown in the tables below.

TABLE 2

| | |
|---|---|
| GC | Clarus 500 |
| Oven | 80° C. isothermal |
| Column | 15 m × 0.25 mm × 1.0 μm Elite 1 |
| Carrier Gas | Helium |
| Injector | Split/Splitless at 250° C., 4-mm liner |
| Split flow | 50 mL/min |
| Detector | Prototype Manifold TCD with 10 μL Cells, 125° C. |

TABLE 3

| | |
|---|---|
| Column carrier gas pressure | 23.5 psig |
| Reference/Make-up Pressure | 14 psig |
| Flow Rate from Port V | 5 mL/min |
| Flow Rate from Port M | 3 mL/min |
| Oven | 80° C. for 10 min |
| Attenuation | ×2 |
| Range | See text |
| Time Constant | 200 ms |
| Data processing | TotalChrom 6.3.2 |
| Data Rate | 12.5 Hz |
| Sample | 0.5 μL of 1% v/v n-Octane and 10% v/v n-Nonane in Hexane |
| Injection | Fast, by autosampler |

Figure 58:
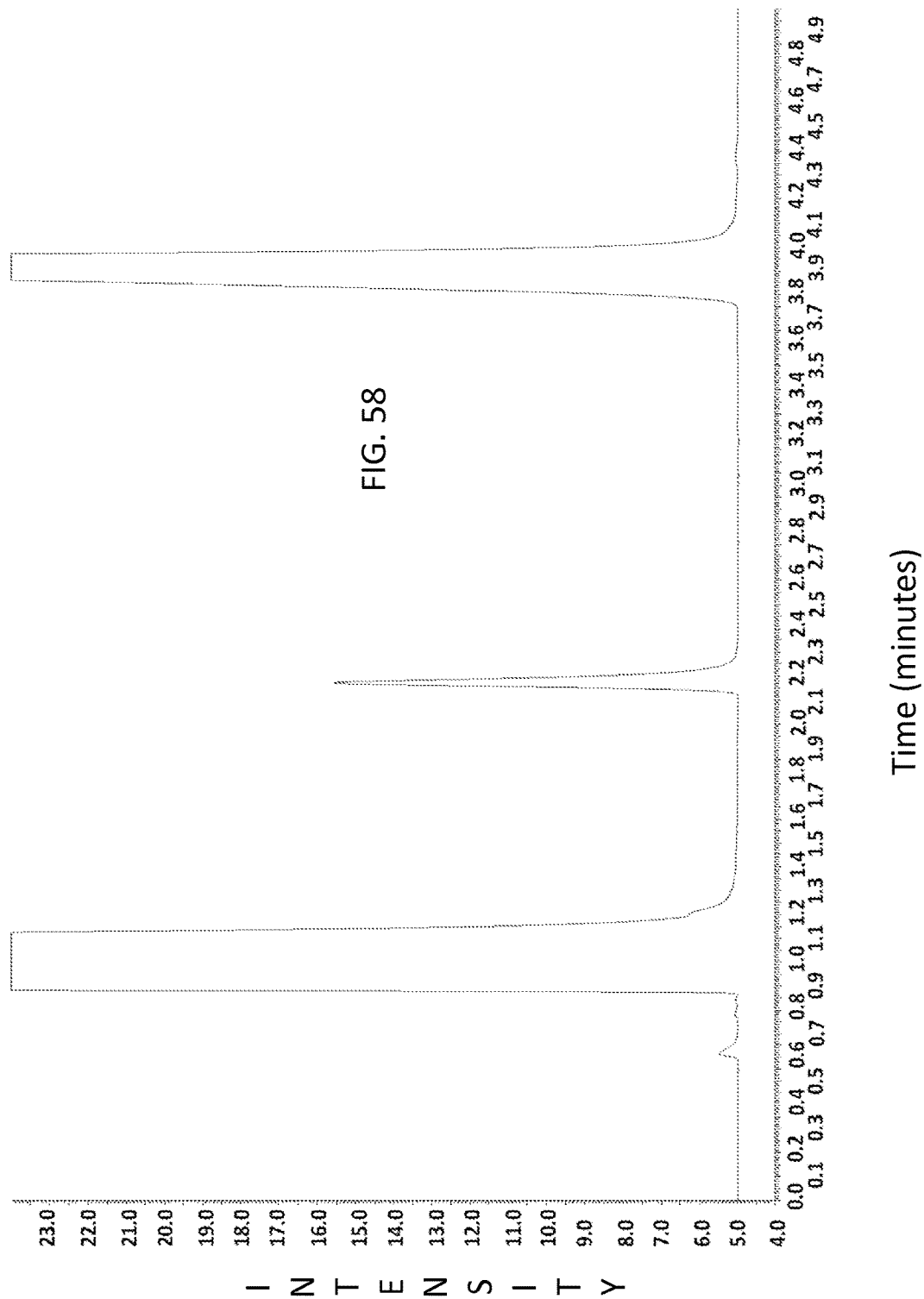
FIG. 58 is a chromatogram of n-octane detected with the 10 microliter TCD, in accordance with certain examples.

N-octane was detected (retention time of about 2.2 minutes). The results are shown in FIG. 58. The x-axis represents time (running from 0 minutes to 5 minutes in increments of 0.1 minutes), and the y-axis represents intensity (running from 4.0 to 24.0 in increments of 1.0). The peak shape of the n-octane peak with the restrictor manifold present was broader and exhibited some tailing compared to a conventionally configured detector.

Example 23

To determine the effect of cell flow rate on peak shape, adjustments were made to the pressure regulator supplying reference/make-up gas to Port R. In each case, the column inlet pressure and the needle vale on Port M had to be adjusted. Once the new pressure is applied to Port R to deliver the required flow rate at Port M, the needle valve is adjusted to vent half that flow rate plus 1 mL/min (to give just over the flow rate through each cell). Chromatograms were then run and the column inlet pressure was adjusted until a retention time of ~2.2 minutes was observed for n-octane.

The pressure and flow adjustments that were used are listed below. The corresponding figure for each analysis is also listed in the table.

TABLE 4

Figure 59:
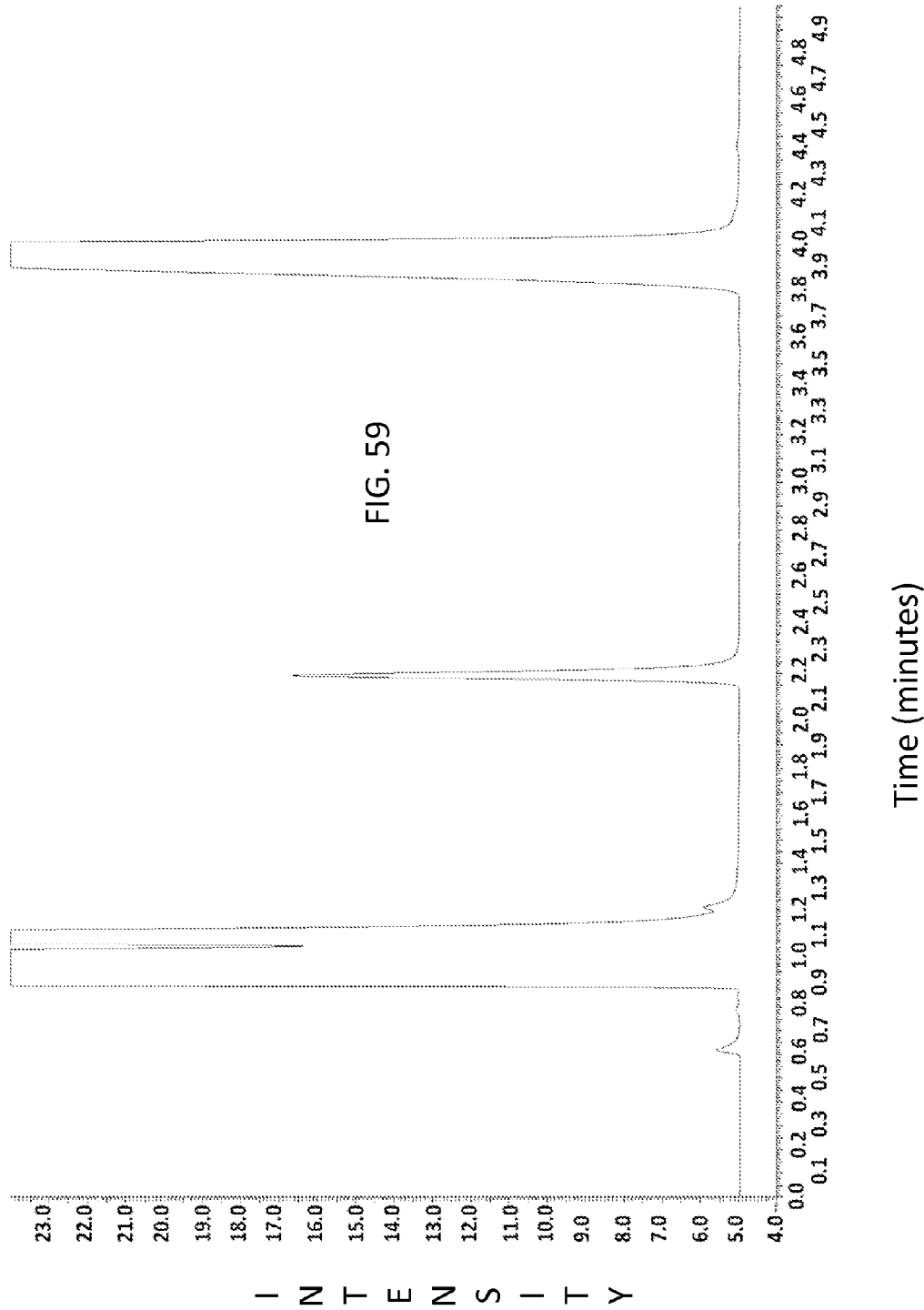
FIG. 59 is a chromatogram from the 10 microliter TCD with restrictor manifold and with 8 mL/min from Port V, in accordance with certain configurations.
Figure 60:
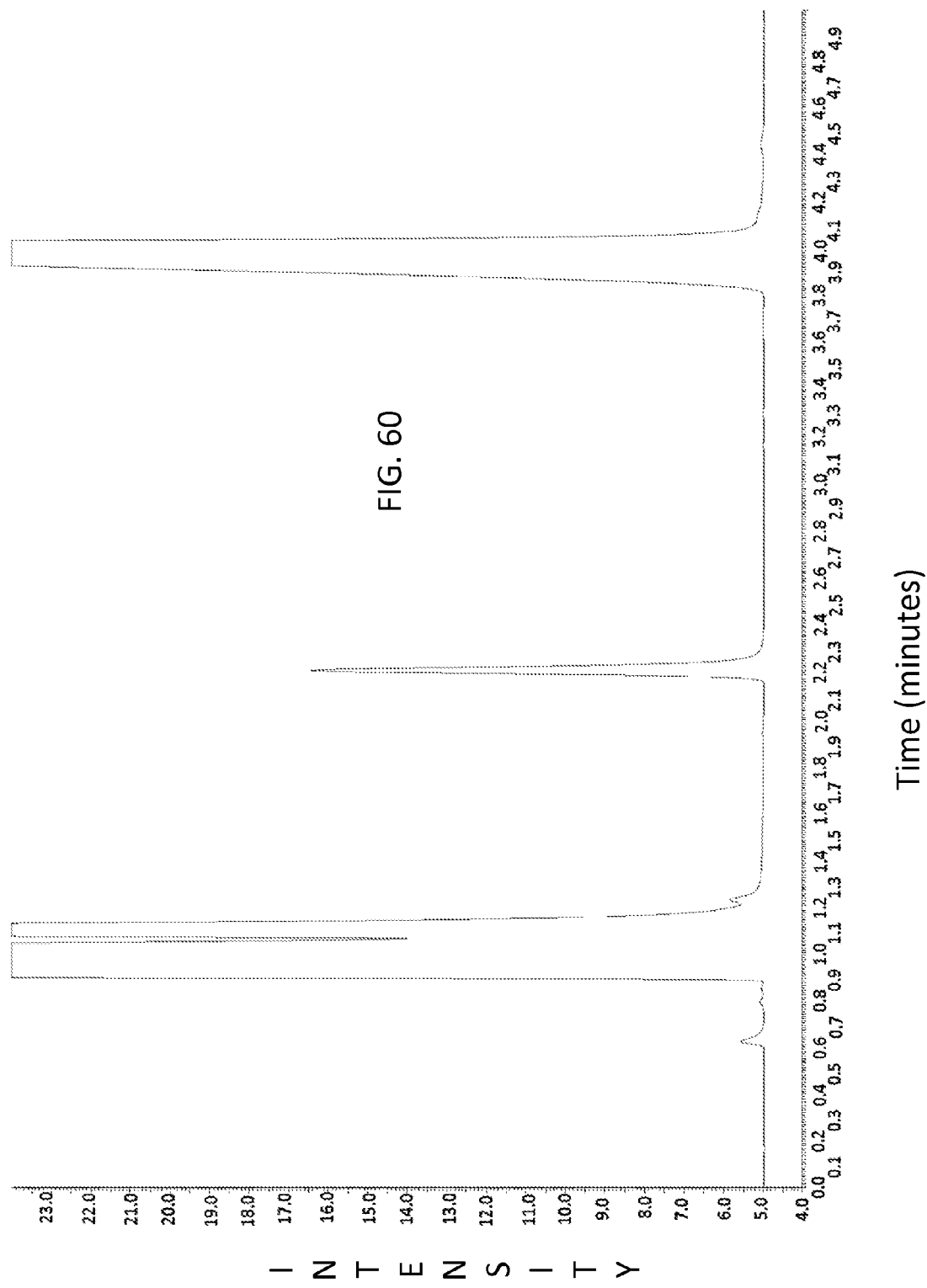
FIG. 60 is a chromatogram from the 10 microliter TCD with restrictor manifold and with 10 mL/min from Port V, in accordance with certain configurations.

| FIG. | Gas Pressure Applied to Port R (psig) | Cell Flow from Port V (mL/min) | Needle Valve Flow from Port M (mL/min) | Column Inlet Pressure (psig) | Calculated Column Flow Rate (mL/min) | Calculated Pressure at Column Outlet (psig) |
|---|---|---|---|---|---|---|
| FIG. 58 | 14 | 5 | 3 | 23.5 | 2.88 | 10.0 |
| FIG. 59 | 22 | 8 | 5 | 26.5 | 3.13 | 13.1 |
| FIG. 60 | 26 | 10 | 6 | 28.0 | 3.25 | 14.7 |

In comparing the peak shapes in FIGS. 58-60, peak shape improved slightly at higher cell flow settings. Reduction in peak tailing was also apparent. In FIGS. 59-60, the x-axis represents time (running from 0 minutes to 5 minutes in increments of 0.1 minutes), and the y-axis represents intensity (running from 4.0 to 24.0 in increments of 1.0).

Data for the n-octane peaks in the chromatograms was processed for comparison. The results are shown in the table below.

TABLE 5

| Filament Current setting, mA[1] | Cell flow rate, mL/min | Column Flow, mL/min[2] | Amt in Column, ng | Peak Area, μV · s | Peak Ht, μV | P-P Noise, μV | Assym Factor | Width at Half Ht, s | Sens uV/ppm | MDQ, ng | MDQ, ng/ml | MDQ, PPb v/v |
|---|---|---|---|---|---|---|---|---|---|---|---|---|
| 80 | 2.5 | 2.88 | 191.44 | 28520 | 10600 | 6.90 | 1.63 | 2.298 | 0.460 | 0.249 | 2.603 | 480.5 |
| 80 | 4.0 | 3.13 | 207.08 | 27730 | 11650 | 7.60 | 1.37 | 2.081 | 0.677 | 0.270 | 1.948 | 359.7 |
| 80 | 5.0 | 3.25 | 214.53 | 26550 | 11500 | 4.45 | 1.17 | 2.034 | 0.788 | 0.166 | 0.980 | 180.8 |

Performance did improve with increasing cell flow rate—the peaks were narrower and more symmetric, and noise levels decreased as well.

Example 24

To test the effect of filament current, the conditions (10 mL/min cell flow from port V) used to provide FIG. 60 were used along with different filament currents. The various filament currents are listed in the table below. The corresponding chromatograms are also listed in the table.

TABLE 6

Figure 61:
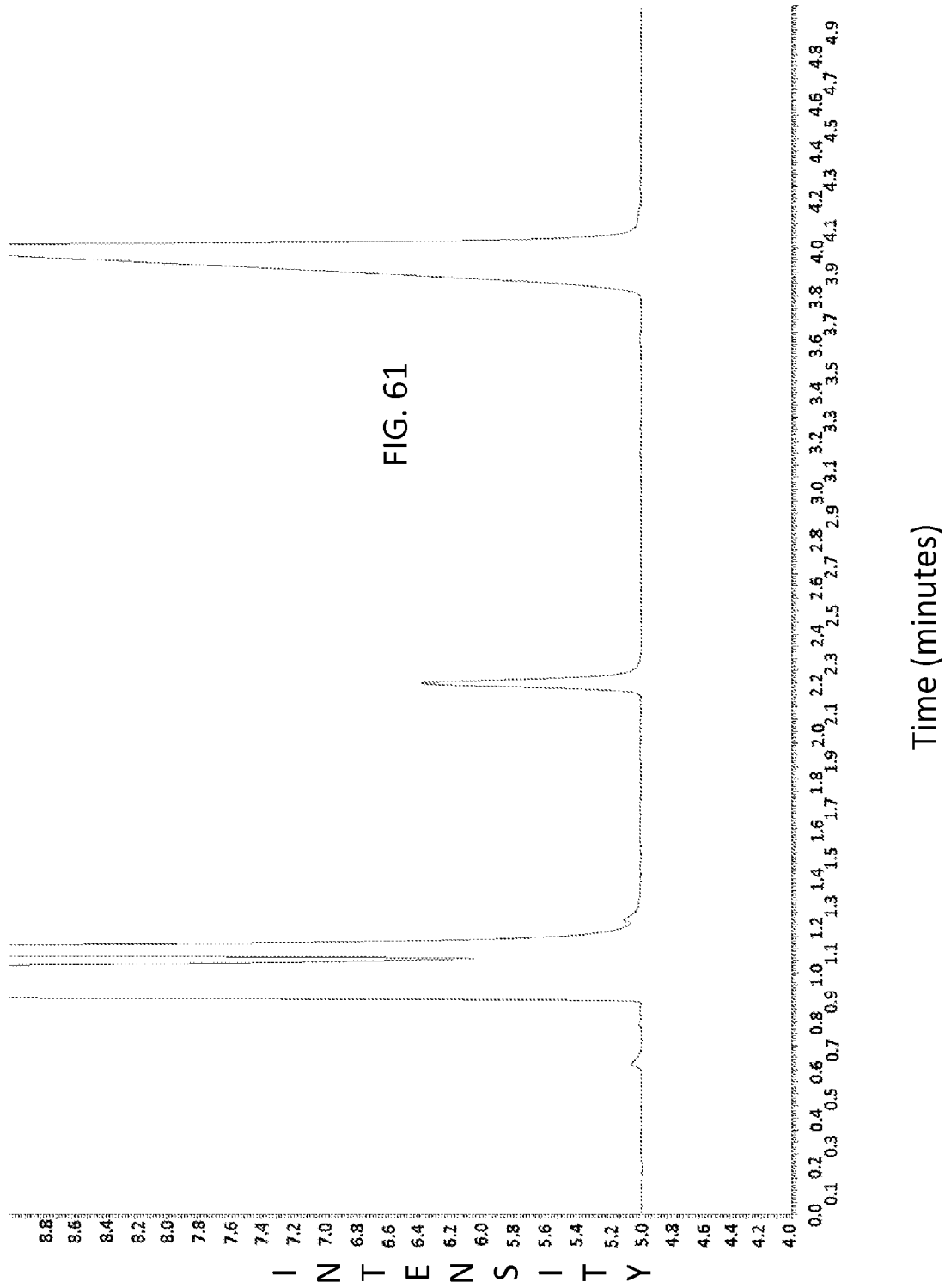
FIG. 61 is a chromatogram from the 10 microliter TCD with restrictor manifold and with 10 mL/min from Port V and a 40 mA cell current; in accordance with certain examples.
Figure 62:
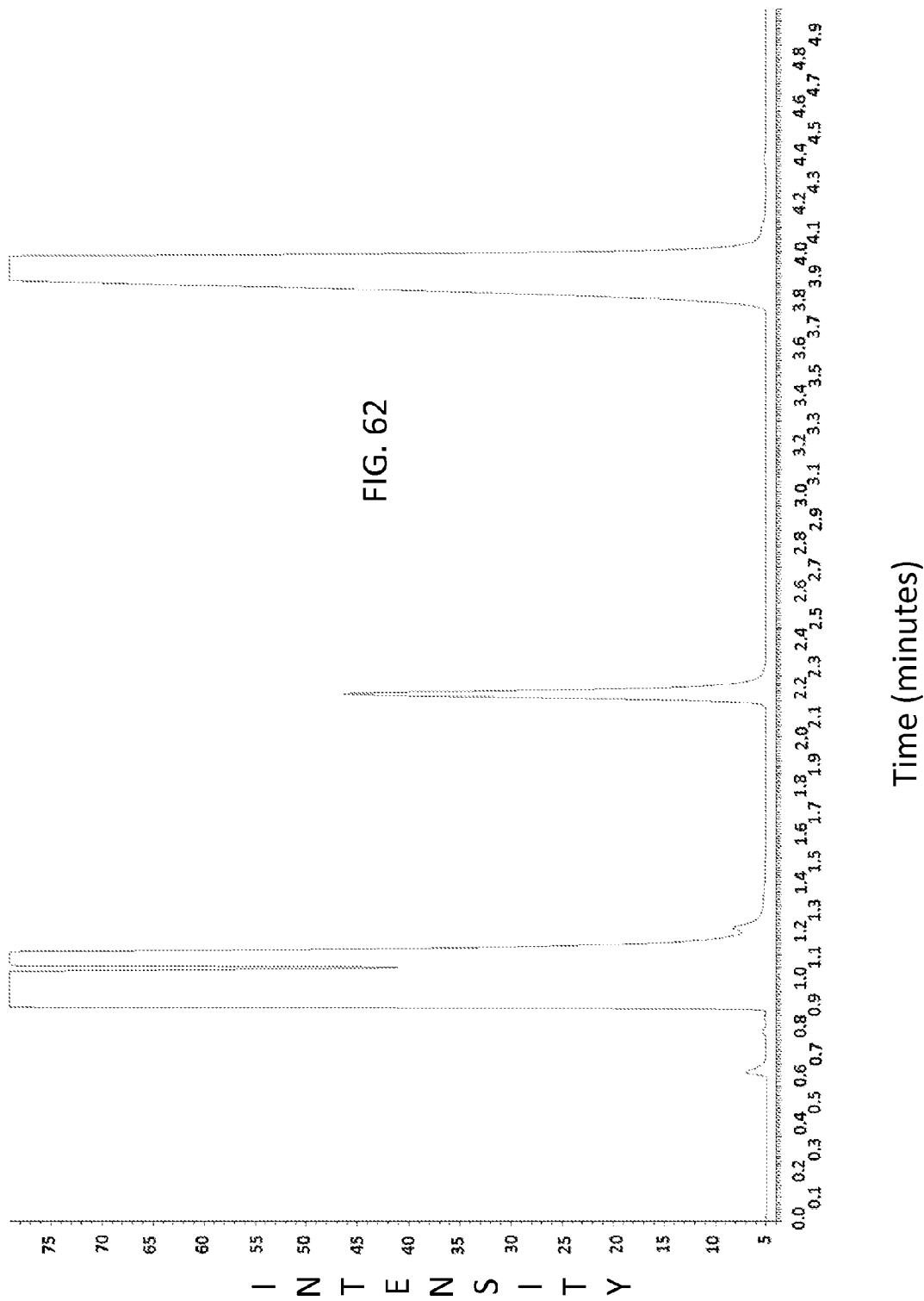
FIG. 62 is a chromatogram from the 10 microliter TCD with restrictor manifold and with 10 mL/min from Port V and a 120 mA cell current; in accordance with certain examples.
Figure 63:
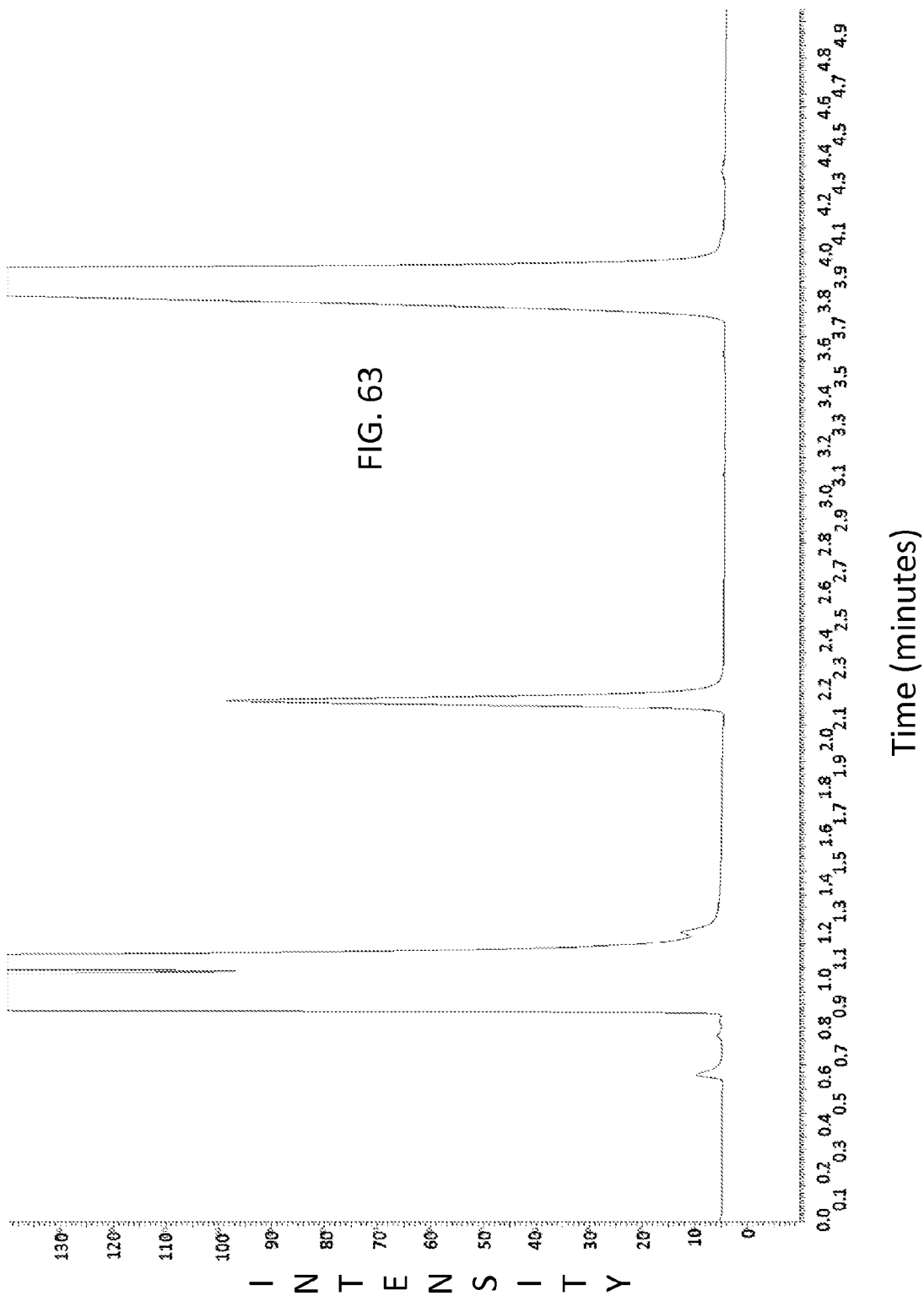
FIG. 63 is a chromatogram from the 10 microliter TCD with restrictor manifold and with 10 mL/min from Port V and a 160 mA cell current; in accordance with certain examples.

| FIG. | Set Cell Current (mA) |
|---|---|
| FIG. 61 | 40 |
| FIG. 60 | 80 |
| FIG. 62 | 120 |
| FIG. 63 | 160 |

In FIGS. 61-63, the x-axis represents time (running from 0 minutes to 5 minutes in increments of 0.1 minutes). In FIG. 61, the y-axis represents intensity (running from 4.0 to 9.0 in increments of 0.2). In FIG. 62, the y-axis represents intensity (running from 5 to 80 in increments of 5). In FIG. 63, the y-axis represents intensity (running from 0 to 140 in increments of 10). The corresponding metrics at different filament currents are shown in the table below.

TABLE 7

| Filament Current setting, mA | Cell flow rate, mL/min | Column Flow, mL/min | Amt in Column, ng | Peak Area μV·s | Peak Ht, μV | P-P Noise, μV | Assym Factor | Width at Half Ht, s | Sens uV/ppm | MDQ ng | MDQ, ng/ml | MDQ, ppb v/v |
|---|---|---|---|---|---|---|---|---|---|---|---|---|
| 40 | 5 | 3.25 | 214.53 | 3143 | 1398 | 5.22 | 1.21 | 2.011 | 0.095 | 1.601 | 9.556 | 1763.9 |
| 80 | 5 | 3.25 | 214.53 | 26550 | 11500 | 4.45 | 1.17 | 2.034 | 0.788 | 0.166 | 0.980 | 180.8 |
| 120 | 5 | 3.25 | 214.53 | 96520 | 41410 | 12.39 | 1.19 | 2.046 | 2.853 | 0.128 | 0.753 | 139.0 |
| 160 | 5 | 3.25 | 214.53 | 219800 | 93950 | 25.98 | 1.21 | 2.051 | 6.488 | 0.119 | 0.694 | 128.1 |

A 160 mA filament current provided the best performance.

Example 25

Figure 64:
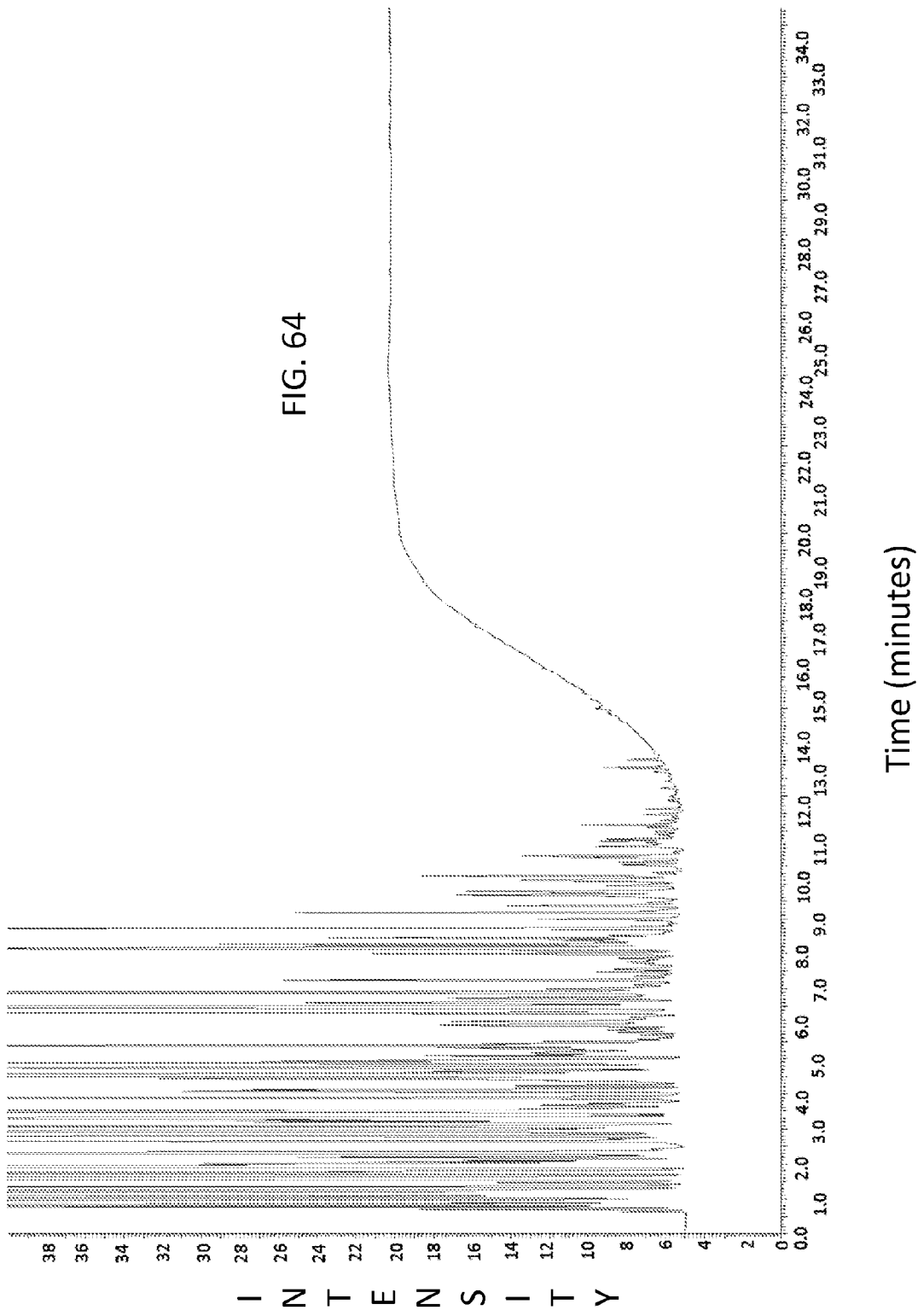
FIG. 64 is a temperature programmed chromatogram of gasoline from a conventional 20 microliter TCD, in accordance with certain examples.
Figure 65:
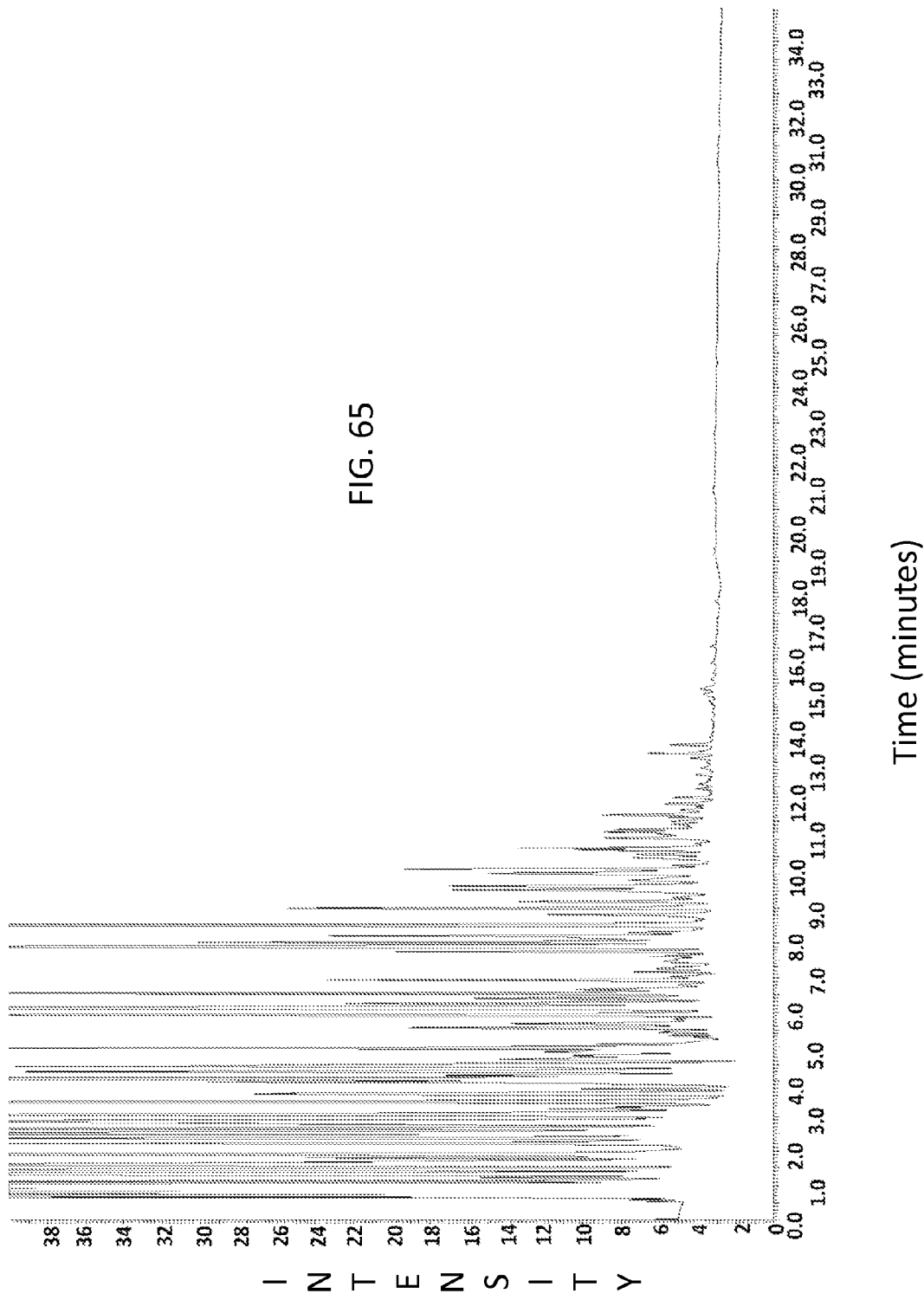
FIG. 65 is a temperature programmed chromatogram of gasoline from a restrictor manifold 10 microliter TCD, in accordance with certain configurations.

Temperature effects of the TCD cell were measured by altering the column oven temperature. A chromatogram of a sample of 87-octane gasoline (0.5 microliters) was analyzed using a conventional 20 microliters TCD design (FIG. 64) and using the microliters test TCD cell (FIG. 65). The chromatography parameters were as follows: Sample was 0.5 microliters of 87-octane gasoline, split flow rate was 100 mL/minute, the column was 15 m×0.250 mm×1 micron Elite-1, helium carrier gas at 2 mL/minute, the cell flow was 5 mL/minute, attenuation was 2×, the range was 160 mA and the detector temperature was 200 deg. Celsius. In FIGS. 64 and 65, the x-axis represents time (running from 0 minutes to 35 minutes in increments of 1 minute), and the y-axis represents intensity (running from 0 to 40 in increments of 2).

In comparing the two chromatograms shown in FIGS. 64 and 65, no temperature drifting of the baseline was observed with the test 10 microliters cell.

Example 26

It is believed that the stability of detector is due, in part, to integration of the restrictors into the cell block. This close thermal coupling between the two restrictors and the four cells shows real benefit. The restrictor temperatures are controlled by the detector set-temperature and can vary according to the applied conditions. The viscosity of the gases flowing through the restrictors can change with different detector temperature settings. TCD response is very flow-sensitive and changing flow rates can directly affect the dilution of the column effluent in the analytical cells.

To determine how changing the detector temperature affected performance, a series of experiments were conducted in which the conditions given in Example 22 were used to perform chromatography with different detector temperatures.

Figure 66:
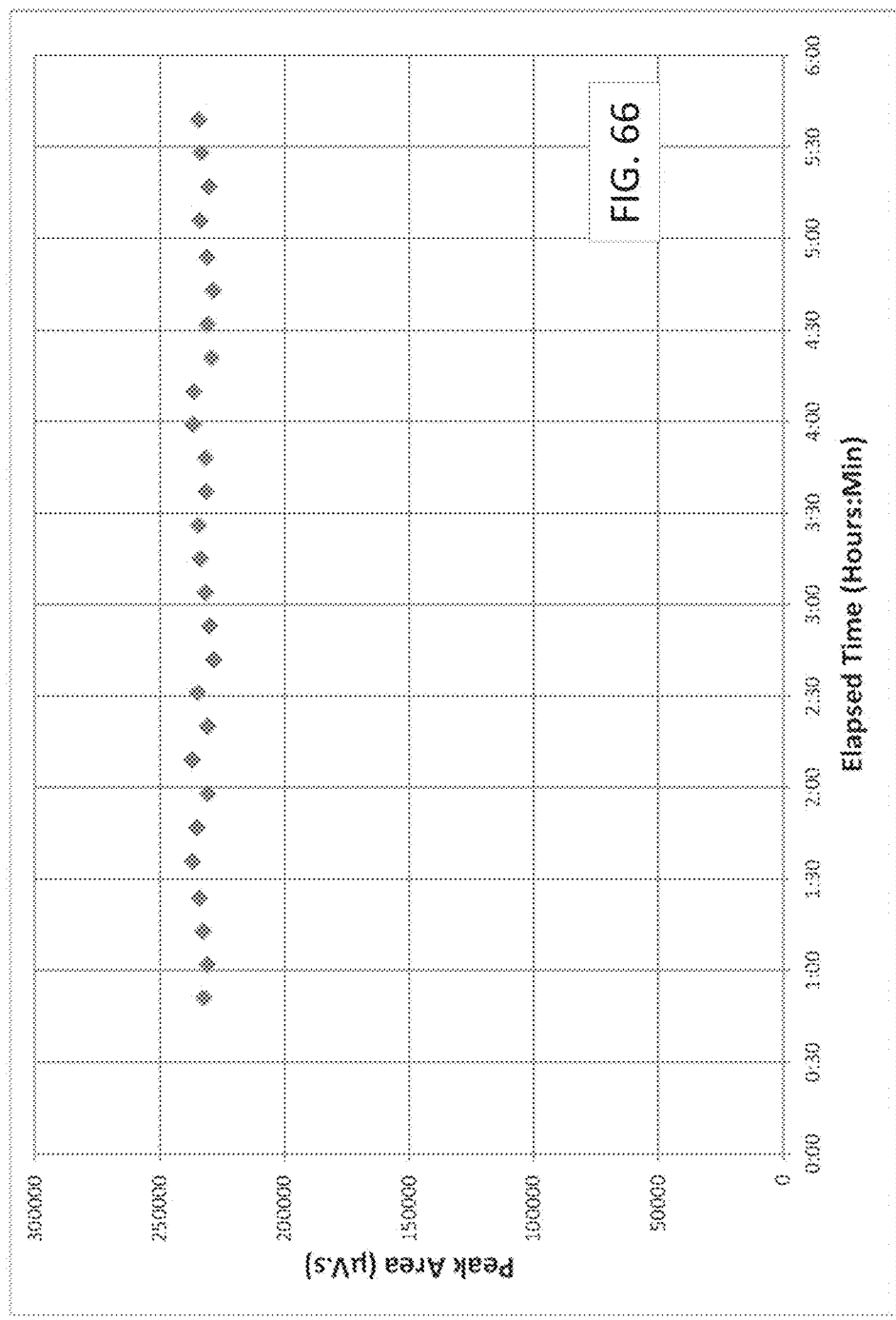
FIG. 66 is a graph showing peak areas vs. elapsed time from the 10 microliter TCD with restrictor manifold at 125 deg. Celsius and with a 160 mA cell current, in accordance with certain configurations.
Figure 67:
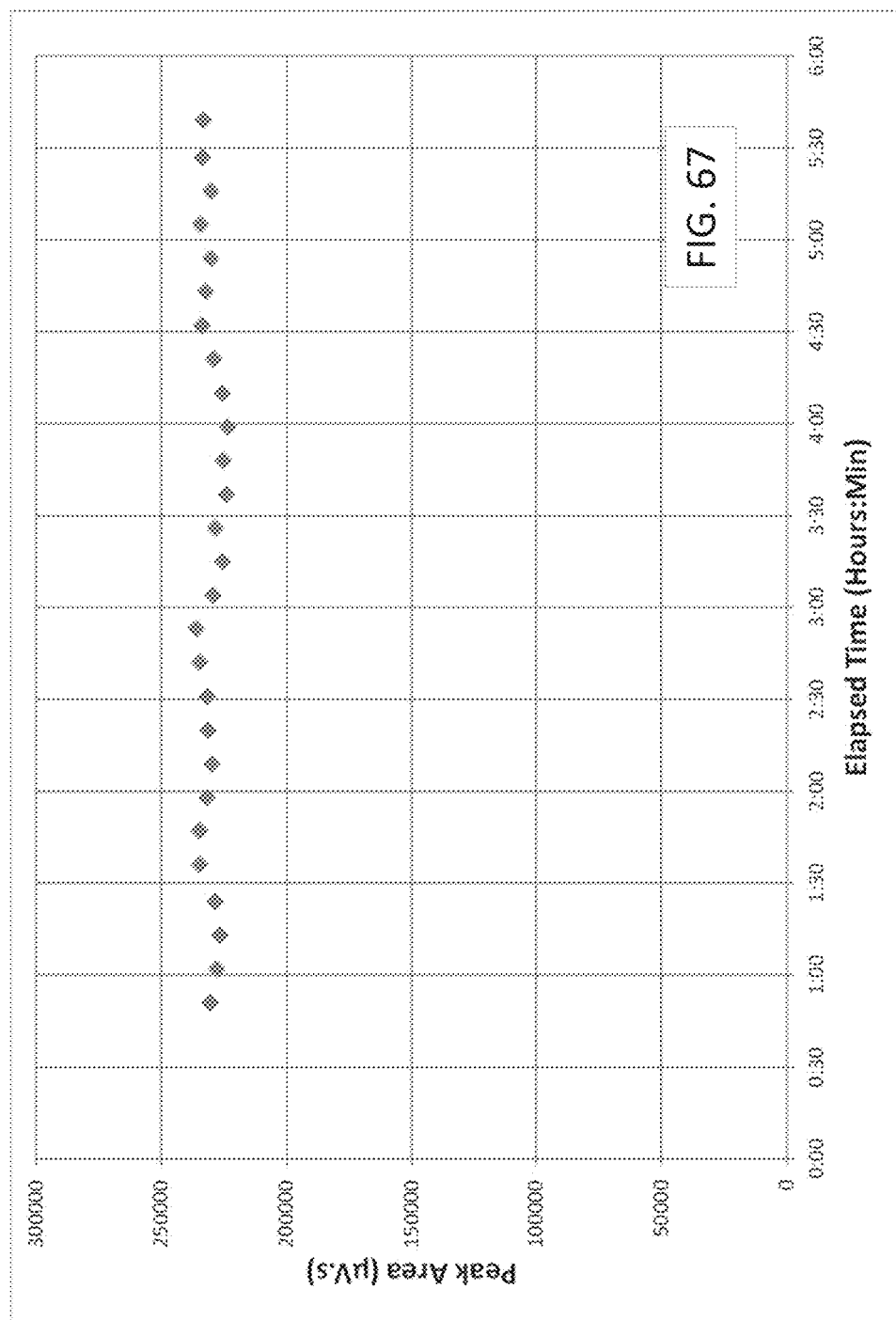
FIG. 67 is a graph showing peak areas vs. elapsed time from the 10 microliter TCD with restrictor manifold at 150 deg. Celsius and with 160 mA cell current, in accordance with certain configurations.
Figure 68:
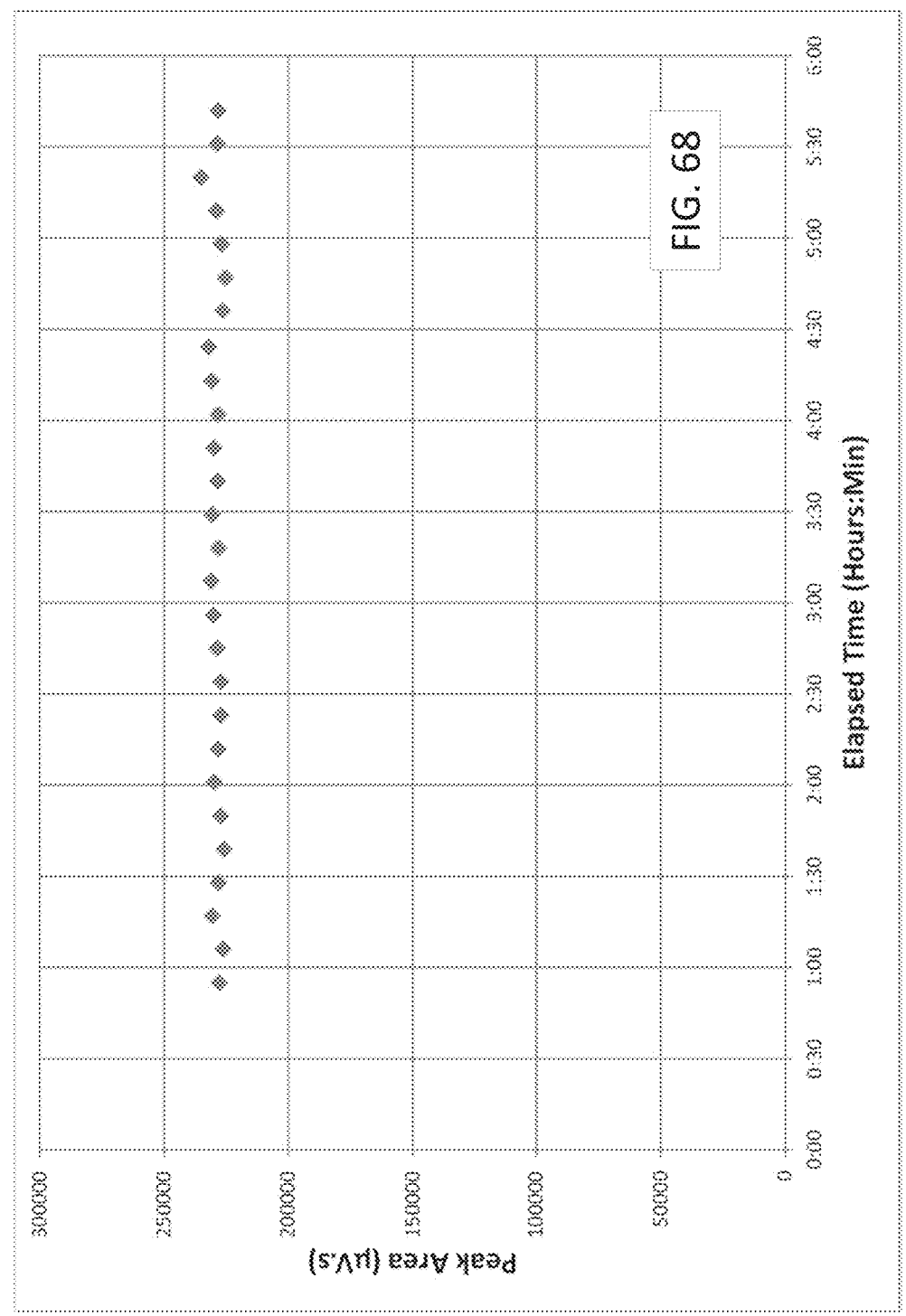
FIG. 68 is a graph showing peak areas vs. elapsed time from the 10 microliter TCD with restrictor manifold at 200 deg. Celsius and with 160 mA cell current, in accordance with certain configurations.
Figure 69:
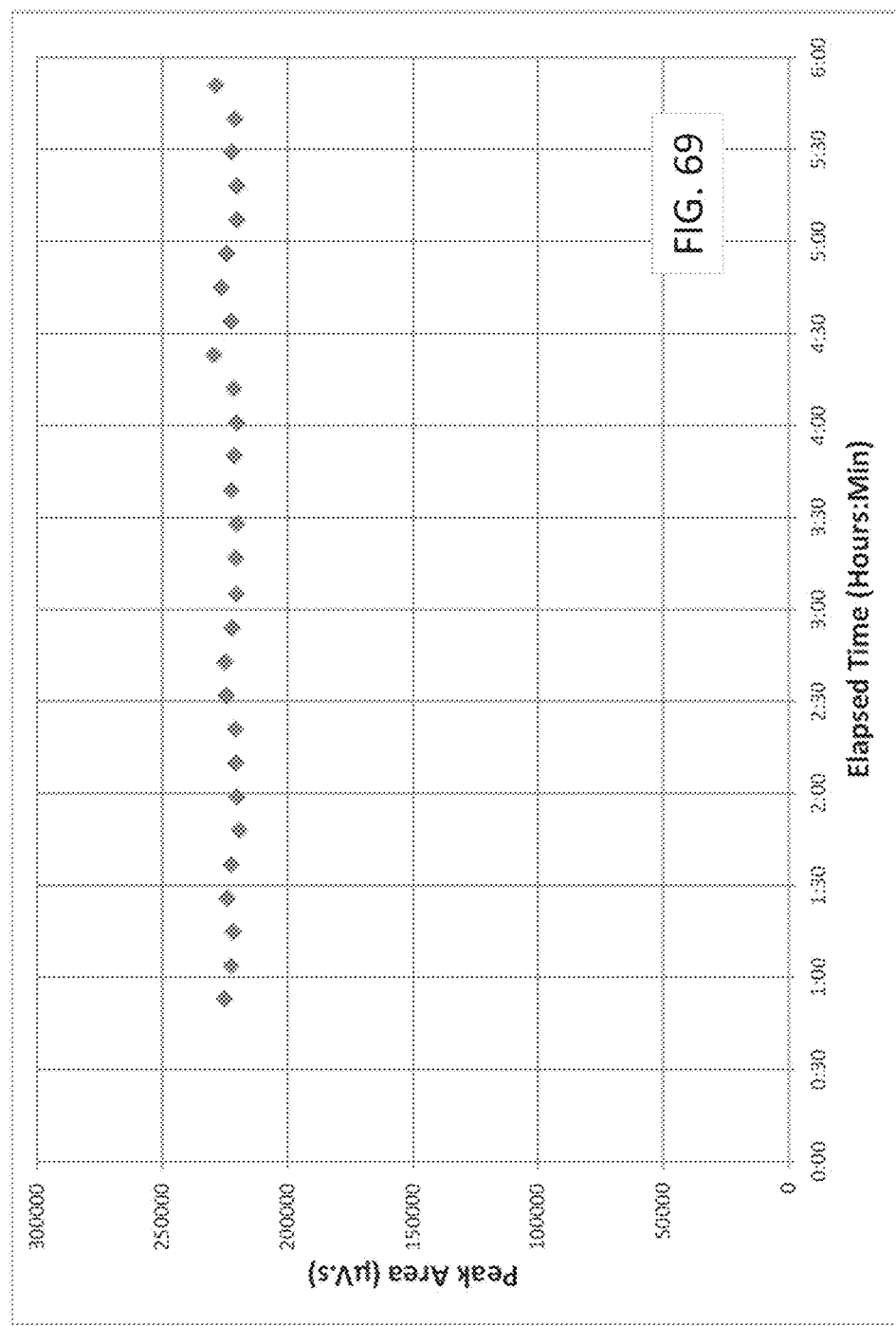
FIG. 69 is a graph showing peak areas vs. elapsed time from the 10 microliter TCD with restrictor manifold at 300 deg. Celsius and with 160 mA cell current, in accordance with certain configurations.

FIGS. 66-69 show the results for peak areas at each detector temperature. In FIG. 66, a restrictor manifold temperature of 125 deg. C. and a 160 mA cell current were used. In FIG. 67, a restrictor manifold temperature of 150 deg. C. and a 160 mA cell current were used. In FIG. 68, a restrictor manifold temperature of 200 deg. C. and a 160 mA cell current were used. In FIG. 69, a restrictor manifold temperature of 300 deg. C. and a 160 mA cell current were used. In all cases, the peak area for n-octane could be determined from the fourth chromatogram which started at about 40 minutes. In each fourth chromatogram, the baseline drifted off scale soon after the n-octane peak which eluted at just over 2 minutes. This prevented the noise value to be determined. However, the fifth chromatogram which started at about 50 minutes stayed on scale and allowed the noise to be determined. This information indicates that the settling time for this detector from cold should be accounted for prior to initiating analysis. The data from the various chromatograms of FIGS. 66-69 are shown in the table below.

TABLE 8

| Temp. (° C.) | n | RT (min) | Mean Peak Width (s) | Mean Assymetry Factor | Mean Area (μV·s) | Area RSD (%) | Mean Height (μV) | Mean Noise (μV) | Mean MDQ (ng) |
|---|---|---|---|---|---|---|---|---|---|
| 125 | 27 | 2.145 | 2.09 | 1.29 | 232625 | 1.08 | 96065 | 25.9 | 0.11 |
| 150 | 27 | 2.112 | 2.09 | 1.30 | 230108 | 1.56 | 95234 | 22.2 | 0.10 |
| 200 | 27 | 2.064 | 2.13 | 1.35 | 228694 | 0.93 | 92978 | 22.2 | 0.10 |
| 300 | 28 | 1.999 | 2.21 | 1.51 | 222527 | 1.15 | 86384 | 41.2 | 0.20 |

Figure 70:
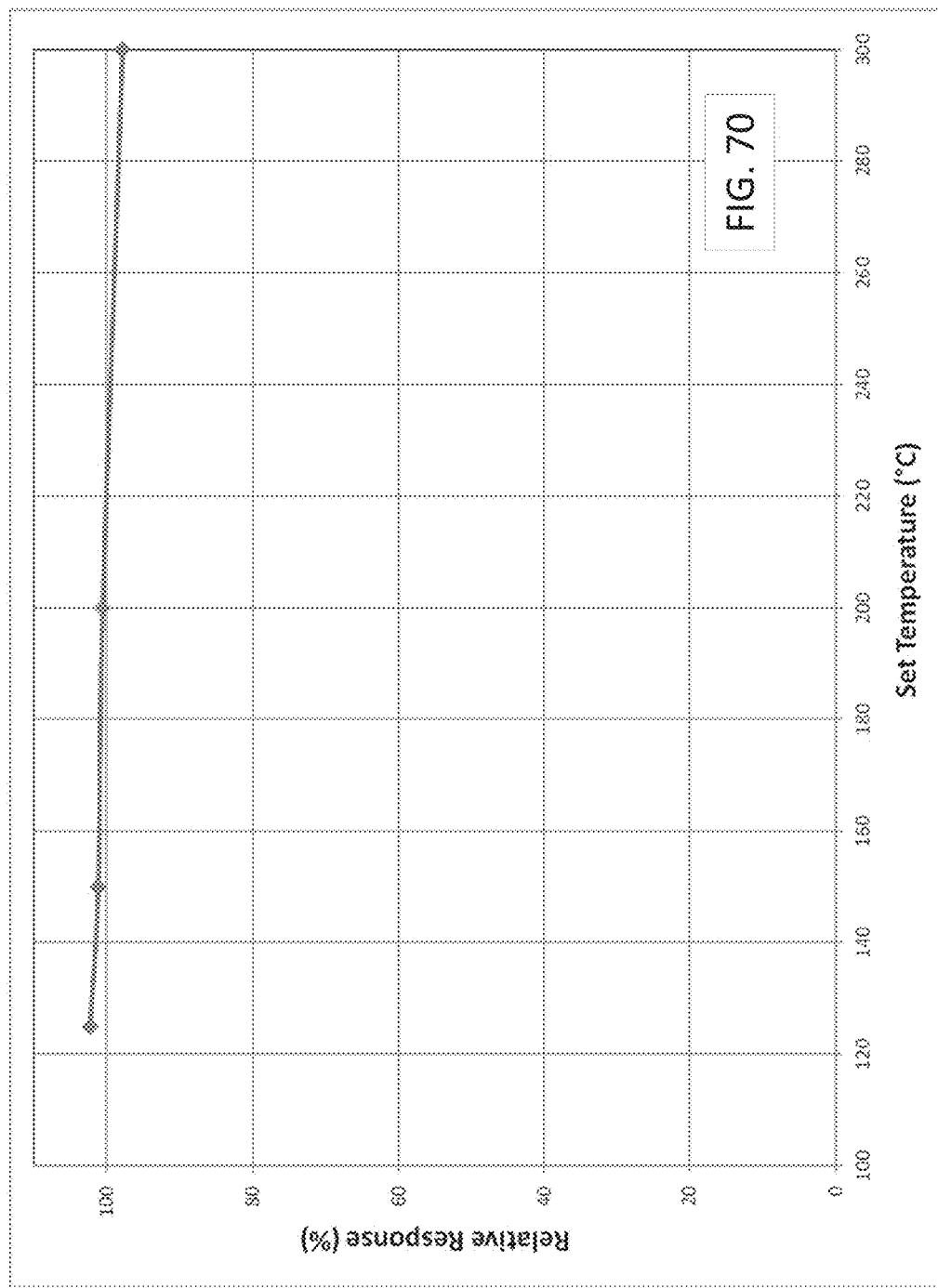
FIG. 70 is a graph showing mean peak areas vs. detector temperature from the 10 microliter TCD with restrictor manifold and with 160 mA cell current, in accordance with certain configurations.
Figure 71:
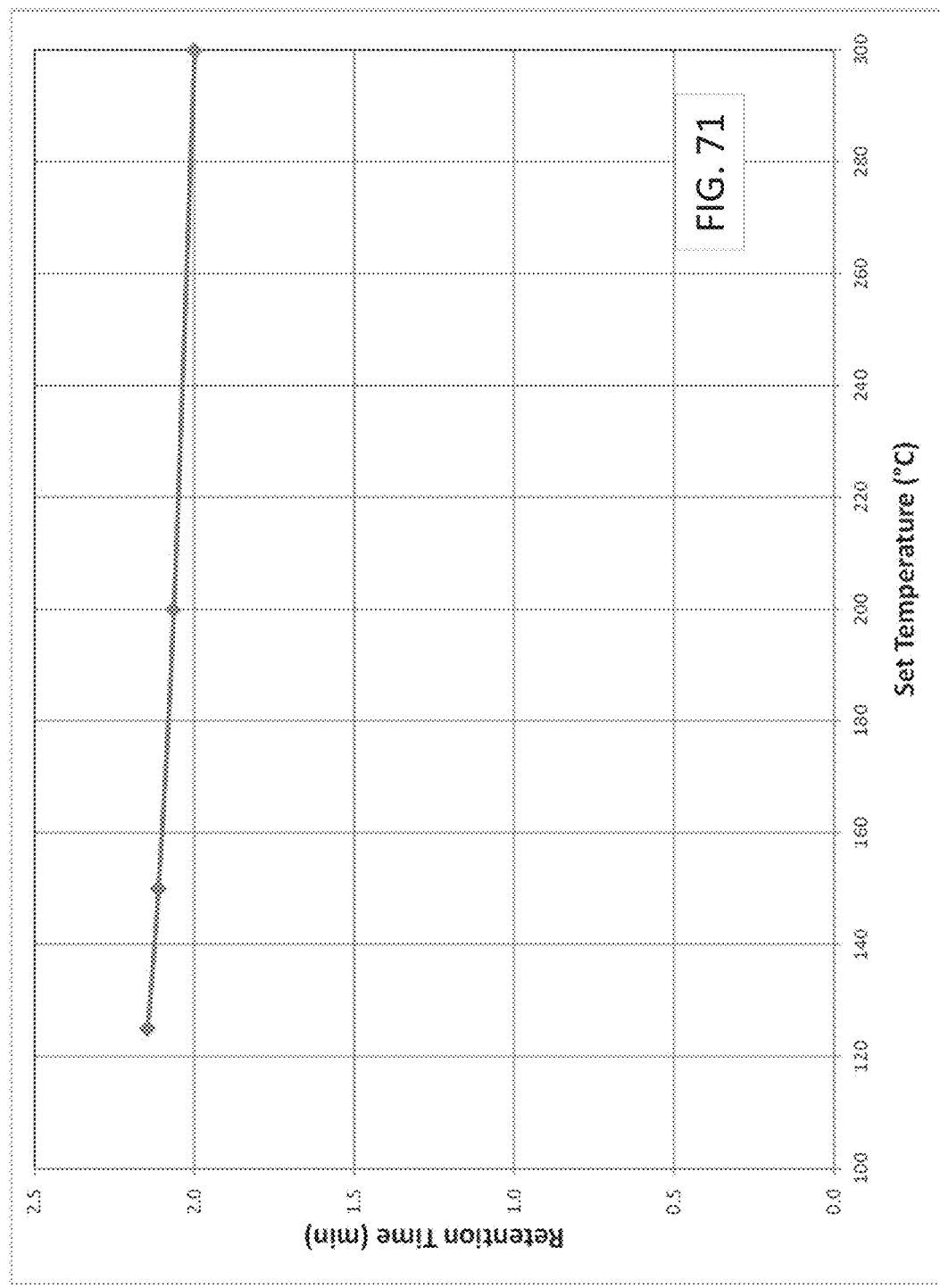
FIG. 71 is a graph showing mean retention times vs. detector temperature from the 10 microliter TCD with restrictor manifold and with 160 mA cell current, in accordance with certain configurations.
Figure 72:
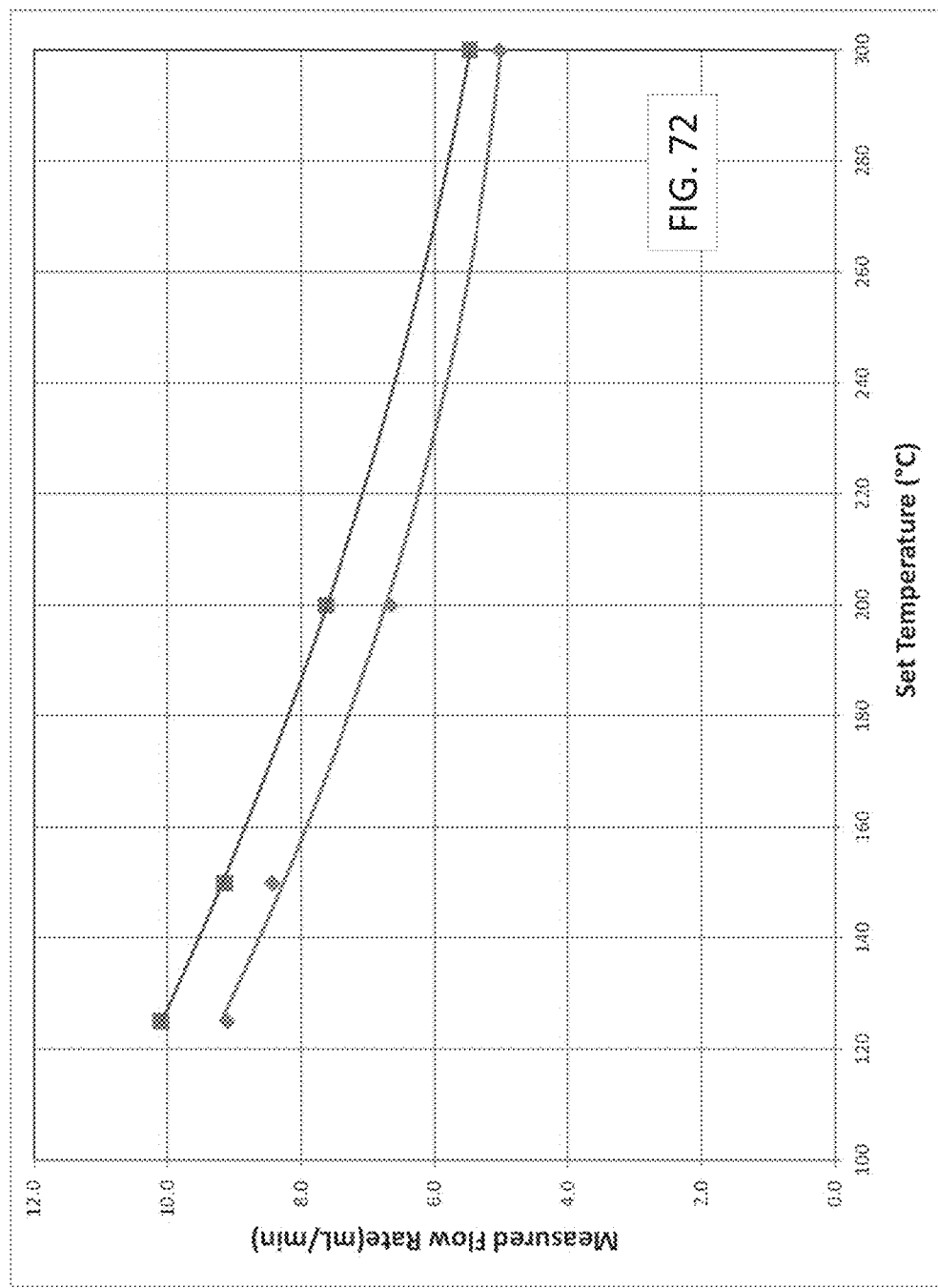
FIG. 72 is a graph showing flow rate vs. detector temperature for the 10 microliter TCD, in accordance with certain examples.

Firstly, the minimum detectable quantity (MDQ) are, in all cases, well within the 0.40 ng target specification. As the detector temperature rises and the flow rate through the cells drops because of increasing gas viscosity, the peak width and the asymmetry increase indicating increasing dispersion and peak tailing. However given the predicted decrease in gas flow rate (~2×—see FIG. 72) as the temperature is increased, this degradation is considered to be quite minor. The peak areas do not seem to be affected much by detector temperature. It is believed that as the temperature rises, the TCD sensitivity may drop, but this effect is offset by the lower flow rate causing less dilution of the sample vapor entering from the GC column. These two effects look like they are self-compensating to some degree. The effect of detector temperature on retention times is plotted graphically in FIG. 70. Retention time appears to be affected by the detector temperature. With close-coupling of the supply pressure regulator to the restrictors, the retention time should not be affected by detector temperature. This information is plotted graphically in FIG. 71.

Example 27

The flow rate of gas through the cells was measured with a flowmeter over the same temperature range as used for the chromatography with the filaments both on and off. Sufficient time (~1 hour) was left between measurements to let the block temperature settle. These data are plotted in FIG. 72. There is significant change in the observed flow rate as the detector set temperature is changed. What also is very evident is the effect of switching the filament current on and off—this can make a 10% difference in the observed flow rate. One would expect this effect of temperature to cause a big disruption in the TCD signal yet, as previously shown in FIG. 70, such changes in flow rate can have a positive effect in compensating for the lower differential temperature between the filaments and the cell block.

Example 28

Following initial power-up to 300° C. and 160 mA, FIG. 73 shows that although the displayed temperature reaches the 300° C. set-point in about 18 minutes, the flow rate (square boxes) doesn't stabilize until later at about 40 minutes. This value is very close to the equilibration times of 40 to 50 minutes established by chromatography.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

The invention claimed is:

1. A manifold comprising first and second internal filament detectors cells within an integral housing, the manifold comprising a sample inlet port fluidically coupled to the first internal filament detector cell through a first restrictor between the sample inlet port and a first filament detector of the first internal filament detector cell, the manifold further comprising a make-up gas port fluidically coupled to the second internal filament detector cell through a second restrictor between the make-up gas port and a second filament detector of the second internal filament detector cell, wherein the second internal filament detector cell is separate from the first internal filament detector cell, and wherein the manifold further comprises an exit port fluidically coupled to each of the first and second filament detector cells, wherein each of the first and second filament detectors comprises two filaments, and wherein the first restrictor and the second restrictor comprise different internal dimensions.

2. The manifold of claim 1, further comprising a vent port fluidically coupled to the make-up gas port.

3. The manifold of claim 1, wherein each of the first filament detector and the second filament detector is configured as a thermal conductivity detector.

4. The manifold of claim 3, further comprising a third internal restrictor between the vent port and the make-up gas port, in which the third internal restrictor is fluidically coupled to each of the vent port and the make-up gas port.

5. The manifold of claim 1, further comprising a flow controller fluidically coupled to the make-up gas port.

6. The manifold of claim 1, further comprising at least one restrictor between the exit port and the first internal filament detector cell or at least one restrictor between the exit port and the second internal filament detector cell.

7. The manifold of claim 1, in which each of the first internal filament detector cell and the second internal filament detector cell comprises a total volume of at least 20 microliters.

8. The manifold of claim 1, further comprising at least one electrical connector configured to electrically couple the first internal filament detector cell and the second internal filament detector cell to a processor.

9. The manifold of claim 1, further comprising a vacuum device fluidically coupled to the exit port.

10. The manifold of claim 1, in which an impedance of the first restrictor is matched to an impedance of the second restrictor.

* * * * *